United States Patent
Chun et al.

(10) Patent No.: US 9,526,782 B2
(45) Date of Patent: Dec. 27, 2016

(54) PHARMACEUTICAL COMPOSITIONS COMPRISING INHIBITORS OF ZINC-ZIP8-MTF1 AS ACTIVE INGREDIENTS FOR PREVENTING OR TREATING A JOINT DISEASE

(71) Applicant: GWANGJU INSTITUTE OF SCIENCE AND TECHNOLOGY, Gwangju (KR)

(72) Inventors: Jang-Soo Chun, Gwangju (KR); Jin-Hong Kim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/595,150

(22) Filed: Jan. 12, 2015

(65) Prior Publication Data
US 2015/0323528 A1 Nov. 12, 2015

(30) Foreign Application Priority Data

Apr. 2, 2014 (KR) .................... 10-2014-003954002

(51) Int. Cl.
| | | |
|---|---|---|
| *C12N 15/11* | (2006.01) | |
| *A61K 48/00* | (2006.01) | |
| *A61K 39/00* | (2006.01) | |
| *A61K 39/395* | (2006.01) | |
| *G01N 33/564* | (2006.01) | |
| *C12Q 1/68* | (2006.01) | |
| *G01N 33/50* | (2006.01) | |
| *C07K 16/28* | (2006.01) | |

(52) U.S. Cl.
CPC ......... *A61K 39/395* (2013.01); *A61K 39/3955* (2013.01); *A61K 48/00* (2013.01); *C07K 16/28* (2013.01); *C12Q 1/6883* (2013.01); *G01N 33/5023* (2013.01); *G01N 33/564* (2013.01); *C12Q 2600/106* (2013.01); *C12Q 2600/158* (2013.01); *G01N 2800/102* (2013.01)

(58) Field of Classification Search
None
See application file for complete search history.

(56) References Cited

PUBLICATIONS

Fernandes et al. 1999. Am. J. Pathol. 154:1159-1169.*
NHS 2014. www.nhs.uk, downloaded Nov. 18, 2015.*
www.niams.nih.gov/health_info/Osteonecrosis/osteonecrosis_ff.pdf, 2014, downloaded Nov. 18, 2015.*
http://www.scleroderma.org/site/PageNavigator/patients_whatis.html#.Vkz66k2FOFU. Downloaded Nov. 18, 2015.*
www.nlm.nih.gov/medlineplus/ency/article/001242.htm, downloaded Nov. 18, 2015.*
Song et al. J. Biomed. Sci. 20:1-6.*
Ryu et al. 2008. J. Nutrition 138:2076-2083.*
J Kim et al., Regulation of the catabolic cascade in osteoarthritis by the zinc-ZIP8-MTF1 axis, 37th KSCB (Korean Society for Cell Biology) Winter Conference 2014, p. 39.
J Kim et al., Regulation of the catabolic cascade in osteoarthritis by the zinc-ZIP8-MTF1 axis, Cell (Manuscript Draft) Manuscript No. CELL-D-13-01520R1.
Chia-Yu Wang et al., ZIP8 Is an Iron and Zinc Transporter Whose Cell-surface Expression Is Up-regulated by Cellular Iron Loading, The Journal of Biological Chemistry vol. 287, No. 41, pp. 34032-34043, Oct. 5, 2012.
John H. Laity et al., Understanding the mechanisms of zinc-sensing by metal-response element binding transcription factor-1 (MTF-1),Archives of Biochemistry and Biophysics 463 (2007) 201-210.
Sonya S. Glasson et al., Deletion of active ADAMTS5 prevents cartilage degradation in a murine model of osteoarthritis, Nature, vol. 434, 31, p. 644-648, Mar. 2005.
Jang-Soo Chun, a government grant proposal dated Jun. 12, 2013, Abstract only.

* cited by examiner

*Primary Examiner* — Shulamith H Shafer
(74) *Attorney, Agent, or Firm* — Harness, Dickey & Pierce, P.L.C.

(57) ABSTRACT

The present invention relates to identification of Zinc-ZIP8-MTF1 axis that plays an important role to OA (osteoarthritis) pathogenesis process and a novel use thereof. According to the present invention, ZIP8 and MTF1 of the present invention increase in the expression in joint disease induced cells or cartilage tissue, and induce the expression of various matrix-degrading enzymes (e.g., MMP-3, MMP-9, MMP-12, MMP-13 and ADAMTS-5 etc.). In addition, when the expression of ZIP8 or MTF1 is inhibited in cells or tissues of animals (e.g., human, mouse), OA pathogenesis is inhibited. Therefore, the ZIP8 and MTF1 of the present invention may be applied to the diagnosis or prognosis of joint diseases, and may be used for the development of therapeutics for joint diseases using these.

6 Claims, 39 Drawing Sheets

SEQUENCE LISTING

<160> NUMBER OF SEQ ID NOS: 4

<210> SEQ ID NO 1
<211> LENGTH: 3383
<212> TYPE: DNA
<213> ORGANISM: Mus musculus

<400> SEQUENCE: 1

```
agagtttctt agagaaagga gagagaaaga cagacagaga gagagagaga gagagagaga        60
gagagagaga gagagagaga gagagagaga gagagaagta ttttgaatat atttgaacct       120
```

-continued

```
cagggctga catagacagt agaggctccg caggaggctc cgagaggcca cactgcctat      180 cgccttctg gctgttctac ctcttcaatg ccccgaaggt ctgagactgc agagcggggg      240
cacggagtgt ctcgctaact gggccaggca gtgacgcggg accggcgcac cctcccaccc    300
ccaccctaac ggcactgaca ccggggcacc ggcgcgggtc cctgcatcag ctagctccgg    360
agctgcgcgc tccacgatgg ctccgggccg ggcagtggcc gggctgctgc tgctggcggc    420
caccagcctg ggacacccct cggagggacc ggagctcgcc ttcagtgagg atgtgctgag    480
cgtgttcggc gccaaccgga gcctgtcggc cgcgcagctg gggcgcctgc tggagcgtct    540
gggggctgca tcccagcagg gagcgctgga cctgggccag ctgcacttca accagtgttt    600
gtcagcagaa gacatctttt ctcttcatgg tttctcaaat gtcacccaga taaccagctc    660
gaacttctct gccatctgcc ccgcgatctt acagcagctg aacttccatc cctgcgagga    720
tctaagaaag cacaacgcaa agcccagtct ttccgaagtc tggggctatg gattcctgtc    780
agtgacaatt atcaatctgg cctctctcct gggattgatt ttaaccccct tgataaagaa    840
gtcttatttc cccaagattt taacttattt cgtgggactg ctattggga ctcttttctc     900 aaacgccatt ttccagctta ttccagaggc atttggattt aatcccaaaa ttgacaatta    960
cgttgagaaa gcagttgctg tgtttggtgg attttacatg cttttctttg tcgagagaac    1020
acttaagatg ctactgaaaa catatggcca gaatgaccat actcacttca ggaatgatga    1080
ctttggttct aaagaaaaaa cccaccaacc caaaacgtta ccattgcctg cagtcaacgg    1140
tgtgacttgc tatgccaacc ccgctgtcac tgagcctaac ggacacatcc acttcgacac    1200
tgtcagcgtt gtatccctcc aggatggaaa aacagagcca agctcatgta cctgtctgaa    1260
ggggcccaaa ctgtcagaaa taggaacaat tgcctggatg atcacgcttt gtgatgccct    1320
ccacaatttc atcgacggct ggcgattgg ggcatcttgt actttgtctc ttcttcaggg    1380
gctcagtacg tccatagcga tcctgtgtga ggagtttcct catgagttag gggactttgt    1440
gatcttgctc aatgcaggaa tgagcacccg gcaagccttg ctgttcaact tcctctccgc    1500
gtgttcctgc tacgtgggac tagctttcgg catttggtg ggcaacaatt ttgctcccaa     1560
tattatattt gcactcgctg gaggcatgtt cctctacatt tctctggcag atatgttcc     1620 agagatgaac gacatgctga gagaaaaagt aactggaaga caaacggatt tcaccttctt    1680
catgatccag aatgcaggga tgttaaccgg cttcactgcc atcctgctca tcaccttgta    1740
cgcaggagac atcgaattgc agtagccgga agtggagtat aacgtcaacg cgggaaggca    1800
tttaataaca acacagaaac atctccatag ggattttgt ttttttaaaa gtatatccta     1860
tttagttaaa agagattttt tttttattat tttcaactaa aggctaagga atctaatgac    1920
tggtttcaga tatgtagaat aggtgaaatt tgttgttaaa attttccctt aaaaggtttt    1980
cggtttcaga ctgcaaaggc tggtgtatgg ggcctttggt aaatacctgg ttttcaatat    2040
tttatgcata ttagaaaatt atcatgaagc aaacacgtgc attcacaagc agacatacag    2100
atccagagaa aaacacaatc tgggtcatgt aaggtttcag aacttgcttg ggtaaacaac    2160
aacaacaaca acaacaacaa caacaacaac aaaaacctca gcgttttca gagtggtttt     2220 cttccaatta atgtgtttga ctgcttttaa aggcaggtgc atcaaatgag gaagaaaatc    2280
aagacagaca gctccagtgc atgcaggacc gatcccagtg ccttaacgaa ccccagaaag    2340
atagcgcaca gcgtttgttc agctttatgt ctcagttggc gacctgtagg attgttttga    2400
aagctaatac aaagtaacat gaattaggaa aggatgaaag gcttgctagc ccagcaaggc    2460
ttgggctcag ggcttggtcc ctgagttata agcttgaaca caccctgcag aagaccagaa    2520
```

```
ttgctttgct atgatttatg ctgtggttcc agccaacaga aatgcctgag gagtatgcga    2580
gactggttag aactcagtct tgccatgctc tgggattgct ttgtcatggt ggagaatatg    2640
ttgggtggga gagagaaatt gaatgtaatt gtgagcaatt tacttttttaa aagatgagca    2700 taattattta gcaggggggaa tttcaataaa tgcaaaaatc acagctgggc tgggctgtgt    2760
cagagactga tggtggagga ggcatgtgct cattaggggt gattgacagt cagcagagac    2820
ggcttctttt atgtgcagtg tgctttgttc ccatatggta taccgttgga tggaaaacct    2880
cagcatactc tttctacctt tcgtaaaaca cacagctcac tgagtgtttg agcacgttgt    2940
agacgatcag tctgaattga acatcctaat ttcaattcac actcccaagt aacttaaaaa    3000
aaagatgatt tgacagtgat gagaattagt aatagaagcc aagttatctc aggaattatg    3060
ttttcctata agcccaaaca catttttcatg taataacagt gcagatttga taaactttaa    3120
catatatgtt tatgtgtatt ctcactttat gactgacaat taaaaaatat tatttgacca    3180
aacagtaaaa gcttttgaaa ccatgtaccg tgtcagttat ttttctctta atatgtcttt    3240
attttgagtg acatcatgtg gctggtgtta tgagaagaga ggcaagtaga gaactgatgt    3300
tgtattattt taaaaatatc tagcaaaaaa atcctacaaa gactaattttt tcatttcaat    3360 aaacacaatc tatattagta taa                                           3383
```

<210> SEQ ID NO 2
<211> LENGTH: 462
<212> TYPE: PRT
<213> ORGANISM: Mus musculus

<400> SEQUENCE: 2

```
Met Ala Pro Gly Arg Ala Val Ala Gly Leu Leu Leu Ala Ala Thr
1               5                   10                  15

Ser Leu Gly His Pro Ser Glu Gly Pro Glu Leu Ala Phe Ser Glu Asp
            20                  25                  30

Val Leu Ser Val Phe Gly Ala Asn Arg Ser Leu Ser Ala Ala Gln Leu
        35                  40                  45

Gly Arg Leu Leu Glu Arg Leu Gly Ala Ala Ser Gln Gln Gly Ala Leu
    50                  55                  60

Asp Leu Gly Gln Leu His Phe Asn Gln Cys Leu Ser Ala Glu Asp Ile
65                  70                  75                  80

Phe Ser Leu His Gly Phe Ser Asn Val Thr Gln Ile Thr Ser Ser Asn
                85                  90                  95

Phe Ser Ala Ile Cys Pro Ala Ile Leu Gln Gln Leu Asn Phe His Pro
            100                 105                 110

Cys Glu Asp Leu Arg Lys His Asn Ala Lys Pro Ser Leu Ser Glu Val
        115                 120                 125

Trp Gly Tyr Gly Phe Leu Ser Val Thr Ile Ile Asn Leu Ala Ser Leu
    130                 135                 140

Leu Gly Leu Ile Leu Thr Pro Leu Ile Lys Ser Tyr Phe Pro Lys
145                 150                 155                 160

Ile Leu Thr Tyr Phe Val Gly Leu Ala Ile Gly Thr Leu Phe Ser Asn
                165                 170                 175

Ala Ile Phe Gln Leu Ile Pro Glu Ala Phe Gly Phe Asn Pro Lys Ile
            180                 185                 190

Asp Asn Tyr Val Glu Lys Ala Val Ala Val Phe Gly Gly Phe Tyr Met
        195                 200                 205

Leu Phe Phe Val Glu Arg Thr Leu Lys Met Leu Leu Lys Thr Tyr Gly
```

```
                    210                 215                 220
Gln Asn Asp His Thr His Phe Arg Asn Asp Phe Gly Ser Lys Glu
225                 230                 235                 240

Lys Thr His Gln Pro Lys Thr Leu Pro Leu Pro Ala Val Asn Gly Val
                    245                 250                 255

Thr Cys Tyr Ala Asn Pro Ala Val Thr Glu Pro Asn Gly His Ile His
                260                 265                 270

Phe Asp Thr Val Ser Val Val Ser Leu Gln Asp Gly Lys Thr Glu Pro
                275                 280                 285

Ser Ser Cys Thr Cys Leu Lys Gly Pro Lys Leu Ser Glu Ile Gly Thr
290                 295                 300

Ile Ala Trp Met Ile Thr Leu Cys Asp Ala Leu His Asn Phe Ile Asp
305                 310                 315                 320

Gly Leu Ala Ile Gly Ala Ser Cys Thr Leu Ser Leu Leu Gln Gly Leu
                325                 330                 335

Ser Thr Ser Ile Ala Ile Leu Cys Glu Glu Phe Pro His Glu Leu Gly
                340                 345                 350

Asp Phe Val Ile Leu Leu Asn Ala Gly Met Ser Thr Arg Gln Ala Leu
                355                 360                 365

Leu Phe Asn Phe Leu Ser Ala Cys Ser Cys Tyr Val Gly Leu Ala Phe
370                 375                 380

Gly Ile Leu Val Gly Asn Asn Phe Ala Pro Asn Ile Ile Phe Ala Leu
385                 390                 395                 400

Ala Gly Gly Met Phe Leu Tyr Ile Ser Leu Ala Asp Met Phe Pro Glu
                405                 410                 415

Met Asn Asp Met Leu Arg Glu Lys Val Thr Gly Arg Gln Thr Asp Phe
                420                 425                 430

Thr Phe Phe Met Ile Gln Asn Ala Gly Met Leu Thr Gly Phe Thr Ala
                435                 440                 445

Ile Leu Leu Ile Thr Leu Tyr Ala Gly Asp Ile Glu Leu Gln
450                 455                 460

<210> SEQ ID NO 3
<211> LENGTH: 7631
<212> TYPE: DNA
<213> ORGANISM: Mus musculus

<400> SEQUENCE: 3
gaagcggaag tgacgctagg gacaggtggg ggcaatcatg gtgccgcttg ggaggggaga      60
agctgctgct gccgccgttg ccgggagccg cggagaaagg ccgttacctt tccatttctc     120
acaattgggc tgagcacacg tgagccatgg gggaacacag tccagacgac aatatcatct     180
tctttaaggg agaggaggat gacctaaccc cgcatgacaa gatgctcagg tttgtggatg     240
acaacggact ggtgccttcc tcatctggaa ctgtttatga taggaccact gttctcatag     300
aacaggaccc tggcactttg gaggatgatg aagacgatgg acagtgtgga gaacccttgc     360
cttttctggt ggaaggtgaa gagggcttct taatagatca ggaagcaatg tcccagggtt     420
acgtacaaca cattatctca ccagatcaga ttcatttgac tataaaccct ggttccacac     480
ccatgccaag aaacattgaa ggtgcaactc ttactctgca gtcggaatgt ccagaaacga     540
aacggaaaga agtaaagcgg taccagtgca cctttgaggg atgccctcgc acctacagca     600
cagcaggcaa cctgcgcacc caccagaaga ctcaccgagg agagtacacc ttcgtctgta     660
atcaggaggg ctgtggcaag gccttcctca cctcctacag cctcaggatc catgtgcgag     720
```

```
tgcacacaaa ggagaagcca tttgagtgtg acgtgcaggg ctgtgagaag gcgttcaaca      780
cactgtacag gttgaaagca catcagaggc ttcacacagg gaaaacgttt aactgtgaat      840
ctcaaggctg cagcaaatac ttcaccacac tcagtgacct gcggaagcac attcggaccc      900
atacaggaga aaagccattt cgatgtgatc acgacggctg tgggaaagcg tttgcagcga      960
gccaccacct taaaactcac gtccggacgc acactggtga agacccttc ttctgcccca     1020 gcaacggctg tgagaagacg tttagcactc agtacagtct caaaagtcac atgaaaggtc     1080
atgataacaa aggcactgca tacagtgcac ttccacagca caatggatca gaggatacaa     1140
atcactcact ttatctgagt gagctgggcc ttctgtccac agattctgaa ctgcaagaaa     1200
attccagttc gacacaggac caggacctca gcacaatttc accagcaatc atctttgaat     1260
caatgttcca gaattccgac gaccctggga ttcaggacga ccctctgcag acagctgcct     1320
tgattgacag ttttaatggt gatgcagagt ccgtcattga tgtcccaccg cctgcaggaa     1380
attcggcgtc tttatctctt ccactcgtac tgcagtctgg catctccgag ccaccccagc     1440
ctctgctacc agcaacagct ccgtccgctc ctccacctgc tccctcccta ggacctggtt     1500
cccagccagc tgcatttggc agccccctg ctctcttaca acctccagaa gtgcctgttc      1560
cccacagcac acagtttgct gctaatcatc aagagtttct tccgcacccc caggcgccac     1620
cccagaccat cgtaccagga cttctgttg ttgctggggc tcctgcatca gcagcaacag      1680
tggcgtcagc cgtggcagca ccagcccac cacaaagtac tactgagccc ctgcctgcta      1740
tggtccagac tctgcccctg ggtgccaact ctgtcctaac taataatccc accataacca     1800
tcaccccaac tcctaacacg gcaatcctgc agtccagcct agtcatggga gaacagaact     1860
tacagtggat attgaacggt gccaccagtt caccacaaaa ccaagaacaa attcagcaag     1920
catcgaaagt ggagcaggtg tacttcgcca ccgctgtacc agtggccagt ggcacaggga     1980
gctctgttca gcagattggc ctcagtgttc ctgtgatcat catcaaacaa gaggaggcct     2040
gtcagtgtca gtgcgcgtgc cgggactctg cgaaggagcg ggcggccggc cggagaaagg     2100
gatgttcttc cccaccccct ccagagccga accccagcc tcctgatggg cccagcctgc      2160
agctgccacc ctagacttct ccctcatccc tgcccccccc cccccctcc gctggacccc      2220 cttcctgtga gcacagcaga caggctgagg ctcctcagac cctccgaaac gttaagtgcc     2280
atggatgtgt cagagttcct gtccctccag agcctggaca ccccgtccaa tccggttcac     2340
agtgaagcac tactgcaggg gtagaggaaa gagcctggcc ggcagcttct ccaggggaag     2400
ggcctgtgcg cacacccctc caggaacagg gtgagcagga agtaccggct gtgatgctgc     2460
cgtcatgggg tcagaaattg aaggatgaa gaaatctgcc atctgaaagc tcacctttca      2520
gacgtatttt ctttactcgt atcccaggaa catccatttt aaggaactga tctttggagg     2580
aaaaaacaaa aacaaaaac aaaaaaagaa aaaaaaagc taagttataa gtgaactgtc       2640
tggctgcact gtgtgtcact tttgcttatt gttatgtgaa cttggaaact aaggttacgt     2700
gtatgcataa aagttctaaa tgaaagggtg tggtttccat cactttggta ctgcccatca     2760
tttgcactgg ggtcactgtg gattgggcag gagaggccac tgtgcctgcc gggtgttgct     2820
tctcttctgt gtctgtttaa tccgaggcag tacctggagg ccagaccac cgctctatga      2880 aagcggggag tggcaagggc aggcgtgagt tagactgggt gagttgcttt gttgttggca     2940
cttggtttct gtggagcttg gggtagatgc agagggggct gccctgtgtc ctgcttagtc     3000
ctagcgggca gctgcaggcc tcctggccag agggaagatg tggttctgca gggccccgag     3060
gcagttgttg acagctctgt tgataatgtg ctagacccta gagctatcta gcacagccac     3120
```

```
agtcttgcct tcttggctct ttccatctct cagtgcttgt tagtgcttga ggcttgaagt    3180
tcatctctcc tacggaagcg ccctgtttta tcctaaagtg aatgagaggc ttctggccag    3240
tggctgccag ggtcttcctg ccttcgatga tgtttgcttc ctcagagcag aagggctgct    3300
tttccagaga aagtgcagag ctaaaggagt tagatggtga ggcagcaggt ggtcggcagg    3360
cattctggta cccagttgta gccaggcttt ggttatcctc tcccagctgc atgtctcatg    3420
tctcttagat ttgcatacag cctcatacag tgcaaaggaa gatgtgatct ctaaacaaaa    3480
aggaataaaa acctaaaatg atgatattct actcagggta aaacaaacaa acaaacccct    3540
tccaccaaaa agcctgaagc ttgcagtcag tttacctcat ttggaatgtt ttgttgagtt    3600
gtgttacagg aatttttttt tattagtgta taaaattata cccatctcct tgcctttggc    3660
tcctggttat tgcctcttca aacataagta caatctatag gagaatgggg gtgtggctgt    3720
ccttcggctg tttactgtag ccatcagtgc ttggcaaggt cagaaggtag ctgggtctgg    3780
gactggagga ggcgtctgtc tccagcaaag agcagggtct ggtgcccaa caggacaacc     3840 agagagctgt gtaggttgcc ctcctgcagt ctggaccttt cctcagagcc agctaggatg    3900
gtgacccttg tctttaggca aggtatttag ggacaattgg ccaagagggt catggcagca    3960
ctattgagaa atggcacagg tacaagcagc tgatctccca ttccaggatt ggaccaggag    4020
tatgaatttc tgatgttcta caccccccaca ccccacacac acccaaaaaa ggttgatgga   4080
tttgggcaac catagacctc agcaggaatc tgcacggtgt gaggagcccc ctgttggcgc    4140
cgtggttagt ccttctggga accagctgct tgggtgtaga ttgtcctcag ctgtctctag    4200
gacttgcact cacaggaagc tttgcactcg ggccctcact cgtttctctt ctctgaggag    4260
agcagtgaat gggaccccca aagtgagctt gtaacaaggg gtagtaatgg ccctcccact    4320
cactctgcct atgacaccct gggagctgac ataggaaaca ggagcctagg gaggatgtat    4380
ggaaggtttc aatggtttaa atatggcttc ttggtttgct agggctgtgc tcttaatggt    4440
ccattcctag gttattggct tttcaccctc cacagttggc atggtgaaga aacatttgag    4500
cagtgttgag gctgaagtgt tgctaggtga aggagctaag tgattttaga acacaagaga    4560
ctctcagaac ctaagaggtt ttggaaagtg aggactctgc ttgcagttgg tggttgtgga    4620
gagccaatgt gtgaaacagg gtagacagag gcttcggcca tgcttgtacc agtggtcctt    4680 ccccccatctt tccacaagcc cagcctctaa tgctaaggac cttggagaag agggaacctc    4740
ctggctaaac tagaaccacg aagacccttc atggagtggt ttcgccaggg aatgaccttta   4800 gggtaaggcc aagaagagtg aattctggca agtcgattaa gcctttcctt ccacgacagc    4860
catcaccact gtcaccctgt agacgagact tgggttacca ctagcatctc cagtttagcc    4920
tcttccaaga gactagttgg cagcagggct gatggaccta ggaggtggtc aggtgatctt    4980
ggtcccaccc aattgcctta taaatgtggt ccttcccagg caggagggta aggctgagag    5040
aagagagctc agtgcccttg ggcagcacta gtttggccac aggagtactg tcctctgttg    5100
actttggttc ataagatgat ggtacaatgc caaggagagg cttggggtgt ggagagccct    5160
ctaggtagaa ggcaatggga ctcccccttcc cttcagagt cagtggatgg gaaaaggttg     5220
ttttccggat caaggcagtg ggctgatggg gtaatggagg tgcctgagtt ttgcctgagg    5280
ctttgtatta tgctgaatgt gtccagaggg acaaatttgc agaacctcat attgatattt    5340
taaataataa aataaaaagc acttttaggtt acttttatct ttaacccaat tgctgcaatt    5400
tctgttgtgt atgtatatat acatatatat actttcccca aagtttttatt ttttgctcag   5460
```

```
aataaaagtt aagttgaggt gtaaaaagag cacttacttg ggtgcaatat atgcgtagct    5520
tgacagtcgc tatcccacgt ggccctggcc tggccttctg ctccatcagc cctgtgctga    5580
agctggccac agggaaccac tatcagcatc tcagcagctg ctcaatctat gcaagccttc    5640
ctgtgtgtcc ggggcgcccc cctcaggccc tccaaggaac tgctgcagct gttttcttct    5700
gactgttgag gccccttttc aactgcttct ccgccgtccc ctgctctttc ccctcttccc    5760
cagaacaaaa tgattcctga aggaagggt cggttgttcc taggtagaaa cctggcacct    5820
ttagactttc atatttgtaa acacatccat gaagggaag cgtctccagt gtcactgaga    5880
ctgttggtgt gtggaagtgc actactgtcg cgaatttaca gcttttttcac agccccaatc    5940 agaaatatgt cggaaggctc tctgcaccac ctctgttggc tcaaaagcag aatgacttcc    6000
acgcttcatc aaatccattt aggaagccgt taatgacctc cctcaccggc tcccacttac    6060
tcttaaattc ccaactgtag aggcatttta aatatactcc agccagtgca agattttcac    6120
agatgaagtt tgcaagtggt tgtgctgtga cacagatggg aaattgtcca tctctcctct    6180
gaggcagaag gggatgagcc ataaaactgg atcatacata tttctgattg gtctgtttct    6240
tgcatattct tggatcttgt ttcttatgcc cctgctcttg gggaggttgg tcattagccc    6300
aggcatctct cactgttctg gcggcttgag ggcttctcag tctgcgttga aaatgcaagt    6360
ttaattggat ctgtcaaatt atattatagt acaacctttt tctagaactg gcgtgtaaaa    6420
accatacact gctccttggt ggtggctcac tgggacaaaa ataggtgata atgtcatgtc    6480
actttctcaa ttcaatgcaa tttctacttt tttttttttt aaacaggtaa tgttttcata    6540
aaactttttt ccaccaaaat ctgggtgtt tattgtagta tccccgtgtc cctcgaggtg    6600
ccaagtcagg ggcttgcccg cccttgccgc gggtgttctc aggcttccca agggctgtgt    6660
gagtcaacag cctgcatctt tggttgtgct ttggagaaaa tgtcactgag gttggagtcc    6720
caggtagcta gtccctttc ctgggaattc cctgttgcag tttggggaag gtggctggaa    6780
aacgggcttt tctggttgcc tggctcagat ctagccagaa aaggccacaa actcttttct    6840
aacacaaact aatcattggc cagtggtctt ggtgacaagt ttttaagtcc caaatagttt    6900
tatttgaatt atgtaaaagt accaagttta ttttaaatgt aaaacatggg aacaacggac    6960
ttccactgag cgatatgaaa acgttacagg ttcagtactt ccaaaggaag aaacctccaa    7020
cccctaaaaa gaataaatac gaatttgtat ttttgaagaa tgtgaaataa tagtgtttgc    7080
ttaattgctc attttgtata aacttaatat tgtactttaa aatatctgct atgaagtgaa    7140
aatttaactt tttggaattg aaaaagcaat attaaatact aatgaaatct taattaaatg    7200
cttatttaaa tctggtagta catgtggcat tacttcccat ccctgtccct ggttgacact    7260
ctcttcccac tcccagccat caagtcttgg agggacagaa aagaaaggtc agtcaccagg    7320
gtctgcagat ttccttttaa tcaagactct gctcaagtgt tttgtggggc tgagagcccc    7380
caaagcatga aatgaacatg taataccacc tggaaccccc aaagcaggcc agaccactct    7440
ggccagcact gctggcttcc tgaatccgag tactcaagac tggatgtttg ttggctccat    7500
ttcaaagcac agtactgcct tcagccagga cgacgtggga gtgaacccag ctgctagtag    7560
agttgccatc ccaggctgag ggccaagtac cagcaactgc ccgtgaagac tggccccttt    7620
tagtgaaggg a                                                          7631
```

<210> SEQ ID NO 4
<211> LENGTH: 675
<212> TYPE: PRT
<213> ORGANISM: Mus musculus

<400> SEQUENCE: 4

```
Met Gly Glu His Ser Pro Asp Asp Asn Ile Ile Phe Phe Lys Gly Glu
1               5                   10                  15

Glu Asp Asp Leu Thr Pro His Asp Lys Met Leu Arg Phe Val Asp Asp
            20                  25                  30

Asn Gly Leu Val Pro Ser Ser Gly Thr Val Tyr Asp Arg Thr Thr
        35                  40                  45

Val Leu Ile Glu Gln Asp Pro Gly Thr Leu Glu Asp Asp Glu Asp Asp
    50                  55                  60

Gly Gln Cys Gly Glu Pro Leu Pro Phe Leu Val Glu Gly Glu Gly
65                  70                  75                  80

Phe Leu Ile Asp Gln Glu Ala Met Ser Gln Gly Tyr Val Gln His Ile
                85                  90                  95

Ile Ser Pro Asp Gln Ile His Leu Thr Ile Asn Pro Gly Ser Thr Pro
            100                 105                 110

Met Pro Arg Asn Ile Glu Gly Ala Thr Leu Thr Leu Gln Ser Glu Cys
            115                 120                 125

Pro Glu Thr Lys Arg Lys Glu Val Lys Arg Tyr Gln Cys Thr Phe Glu
130                 135                 140

Gly Cys Pro Arg Thr Tyr Ser Thr Ala Gly Asn Leu Arg Thr His Gln
145                 150                 155                 160

Lys Thr His Arg Gly Glu Tyr Thr Phe Val Cys Asn Gln Glu Gly Cys
                165                 170                 175

Gly Lys Ala Phe Leu Thr Ser Tyr Ser Leu Arg Ile His Val Arg Val
            180                 185                 190

His Thr Lys Glu Lys Pro Phe Glu Cys Asp Val Gln Gly Cys Glu Lys
        195                 200                 205

Ala Phe Asn Thr Leu Tyr Arg Leu Lys Ala His Gln Arg Leu His Thr
    210                 215                 220

Gly Lys Thr Phe Asn Cys Glu Ser Gln Gly Cys Ser Lys Tyr Phe Thr
225                 230                 235                 240

Thr Leu Ser Asp Leu Arg Lys His Ile Arg Thr His Thr Gly Glu Lys
                245                 250                 255

Pro Phe Arg Cys Asp His Asp Gly Cys Gly Lys Ala Phe Ala Ala Ser
            260                 265                 270

His His Leu Lys Thr His Val Arg Thr His Thr Gly Glu Arg Pro Phe
        275                 280                 285

Phe Cys Pro Ser Asn Gly Cys Glu Lys Thr Phe Ser Thr Gln Tyr Ser
    290                 295                 300

Leu Lys Ser His Met Lys Gly His Asp Asn Lys Gly Thr Ala Tyr Ser
305                 310                 315                 320

Ala Leu Pro Gln His Asn Gly Ser Glu Asp Thr Asn His Ser Leu Tyr
                325                 330                 335

Leu Ser Glu Leu Gly Leu Leu Ser Thr Asp Ser Glu Leu Gln Glu Asn
            340                 345                 350

Ser Ser Ser Thr Gln Asp Gln Asp Leu Ser Thr Ile Ser Pro Ala Ile
        355                 360                 365

Ile Phe Glu Ser Met Phe Gln Asn Ser Asp Pro Gly Ile Gln Asp
    370                 375                 380

Asp Pro Leu Gln Thr Ala Ala Leu Ile Asp Ser Phe Asn Gly Asp Ala
385                 390                 395                 400

Glu Ser Val Ile Asp Val Pro Pro Pro Ala Gly Asn Ser Ala Ser Leu
```

```
                        405                 410                 415
Ser Leu Pro Leu Val Leu Gln Ser Gly Ile Ser Glu Pro Pro Gln Pro
            420                 425                 430

Leu Leu Pro Ala Thr Ala Pro Ser Ala Pro Pro Pro Ala Pro Ser Leu
            435                 440                 445

Gly Pro Gly Ser Gln Pro Ala Ala Phe Gly Ser Pro Pro Ala Leu Leu
            450                 455                 460

Gln Pro Pro Glu Val Pro Val Pro His Ser Thr Gln Phe Ala Ala Asn
465                 470                 475                 480

His Gln Glu Phe Leu Pro His Pro Gln Ala Pro Pro Gln Thr Ile Val
            485                 490                 495

Pro Gly Leu Ser Val Val Ala Gly Ala Pro Ala Ser Ala Ala Thr Val
            500                 505                 510

Ala Ser Ala Val Ala Ala Pro Ala Pro Pro Gln Ser Thr Thr Glu Pro
            515                 520                 525

Leu Pro Ala Met Val Gln Thr Leu Pro Leu Gly Ala Asn Ser Val Leu
            530                 535                 540

Thr Asn Asn Pro Thr Ile Thr Ile Thr Pro Thr Pro Asn Thr Ala Ile
545                 550                 555                 560

Leu Gln Ser Ser Leu Val Met Gly Glu Gln Asn Leu Gln Trp Ile Leu
            565                 570                 575

Asn Gly Ala Thr Ser Ser Pro Gln Asn Gln Glu Gln Ile Gln Gln Ala
            580                 585                 590

Ser Lys Val Glu Gln Val Tyr Phe Ala Thr Ala Val Pro Val Ala Ser
            595                 600                 605

Gly Thr Gly Ser Ser Val Gln Gln Ile Gly Leu Ser Val Pro Val Ile
            610                 615                 620

Ile Ile Lys Gln Glu Glu Ala Cys Gln Cys Gln Cys Ala Cys Arg Asp
625                 630                 635                 640

Ser Ala Lys Glu Arg Ala Ala Gly Arg Arg Lys Gly Cys Ser Ser Pro
            645                 650                 655

Pro Pro Pro Glu Pro Asn Pro Gln Pro Pro Asp Gly Pro Ser Leu Gln
            660                 665                 670

Leu Pro Pro
        675
```

PHARMACEUTICAL COMPOSITIONS COMPRISING INHIBITORS OF ZINC-ZIP8-MTF1 AS ACTIVE INGREDIENTS FOR PREVENTING OR TREATING A JOINT DISEASE

CROSS-REFERENCE TO RELATED APPLICATIONS

This application claims priority from Korean Patent Application No. 2014-0039540, filed on Apr. 2, 2014, in the Korean Intellectual Property Office, the disclosure of which is incorporated herein by reference.

FIELD OF THE INVENTION

The present invention relates to a novel use of ZIP8 or MTF1 as OA (osteoarthritis) pathogenesis factors.

DESCRIPTION OF THE RELATED ART

Osteoarthritis (OA) is the most common of all arthropathies and is a leading cause of disability with a large socioeconomic cost. To date, however, no effective disease-modifying therapies for OA have been developed. OA is primarily characterized by cartilage destruction, but also involves other pathological changes, including synovial inflammation, osteophyte formation, and subchondral bone sclerosis, in all tissues of joints (Bian et al., 2012; Loeser et al., 2012; Little and Hunter, 2013). OA pathogenesis is caused by an imbalance between anabolic and catabolic factors. A variety of etiologic risk factors and pathophysiological processes contribute to the progressive nature of the disease. Important among potential OA-causing mechanisms are mechanical stresses, including joint instability and injury, and factors that predispose toward OA, such as aging. These factors lead to the activation of biochemical pathways in chondrocytes that result in degradation of the extracellular matrix (ECM) by matrix metalloproteinases (MMPs) and aggrecanases (ADAMTSs). Among matrix-degrading enzymes, MMP3, MMP13, and ADAMTS5 are known to play crucial roles in OA cartilage destruction (Blom et al., 2007; Glasson et al., 2005; Little et al., 2009).

Matrix-degrading enzymes require zinc ($Zn^{2+}$) as a structural component (Page-McCaw et al. 2007). Indeed, $Zn^{2+}$ acts as an activator or co-activator of a variety of proteins by providing a structural scaffold, for example in the form of zinc fingers and zinc clusters (Prasad, 1995). $Zn^{2+}$ may also be overtly toxic when accumulated in excess in cells. Therefore, normal cell functioning requires tight regulation of $Zn^{2+}$ homeostasis. $Zn^{2+}$ homeostasis is primarily regulated by membrane $Zn^{2+}$ transporters of the Slc30a family (ZNT) of exporters and Slc39a family (ZIP) of importers (Cousins et al., 2006). The ZNT family, consisting of 10 members in mammals (ZNT1-ZNT10), mediates $Zn^{2+}$ efflux from cells or influx into intracellular vesicles from the cytosol. There are 14 members of the ZIP family of $Zn^{2+}$ importers in mammals (ZIP1-ZIP14) that promote $Zn^{2+}$ influx from the extracellular fluid or intracellular vesicles into the cytoplasm. $Zn^{2+}$ transporters exhibit tissue specific functions (Liuzzi et al., 2005; Kitamura et al., 2006), and abnormalities in the function of certain $Zn^{2+}$ transporters are associated with human diseases, such as acrodermatitis enteropathica (Kury et al., 2002). $Zn^{2+}$ influx modulates a number of transcription factors in various cell types. Among them, metal-regulatory transcription factor-1 (MTF1) regulates expression of a variety of target genes and thereby regulates cellular adaptation to various stress conditions, primarily exposure to heavy metals, but also hypoxia and oxidative stress (Laity and Andrews, 2007; Gunther et al., 2012). $Zn^{2+}$ homeostasis is additionally regulated by metal-dependent transcriptional control of storage proteins. For instance, metallothioneins (MTs), whose genes are well-known targets of MTF1, act as $Zn^{2+}$-storage proteins and thereby regulate cellular $Zn^{2+}$ homeostasis. MTs also act as antioxidants and protect cells from oxidative stress (Laity and Andrews, 2007; Colvin et al., 2010; Gunther et al., 2012).

There has been a growing interest in the potential role of $Zn^{2+}$ in the pathogenesis of OA. Clinical studies indicate highly elevated serum $Zn^{2+}$ levels in OA patients (Ovesen et al., 2009) and specific accumulation of $Zn^{2+}$ in the tidemark region of articular cartilage in aged populations (Roschger et al., 2013). The association of $Zn^{2+}$ with OA pathogenesis is broadly appreciated in the context of its role as a structural component of matrix-degrading enzymes required for the maturation and activation of these enzymes. However, how $Zn^{2+}$ homeostasis is regulated during the onset and progression of OA, and how it contributes to the pathological transition of articular chondrocytes remain unknown. Here, we investigated the roles of $Zn^{2+}$ homeostasis, homeostasis-regulating $Zn^{2+}$ transporters, and downstream transcription factors and their target genes in OA pathogenesis. We report here that the zinc-ZIPS-MTF1 axis regulates OA pathogenesis.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THIS INVENTION

Technical Purposes of this Invention

The present inventors have made intensive studies to develop pathogenesis molecular factor and therapeutic target of osteoarthritis (OA), which is a representative example of joint disease, particularly degenerative arthritis. As a result, they found out that ZIP 8 playing critical role for homeostasis of cellular $Zn^{2+}$ and MTF1 related to the ZIP 8 are closely relationship with development of OA, and joint disease may be prevented or treated through the inhibitory thereof in animal (e.g., human, mouse) cells or tissues.

Accordingly, it is an object of the present invention to provide a pharmaceutical composition for preventing or treating a joint disease.

It is another object of the present invention to provide a method for a method for preventing or treating a joint disease.

It is still another object of the present invention to provide a method for screening a therapeutic agent for treating a joint disease.

It is another object of the present invention to provide a method for detecting a joint disease in a subject.

It is still another object of the present invention to provide a non-human transgenic animal model for a joint disease.

Other objects and advantages of the present invention will become apparent from the detailed description to follow taken in conjugation with the appended claims and drawings.

Technical Solutions of this Invention

In one aspect of the present invention, there is provided a pharmaceutical composition for preventing or treating joint disease, comprising an inhibitor of the expression of a ZIP8 or MTF1 (metal-regulatory transcription factor-1) gene or protein, or an inhibitor of the activity of the ZIP8 or MTF1 protein as an active ingredient.

In another aspect of the present invention, there is provided a method for preventing or treating a joint disease, comprising administering to an subject in need thereof an inhibitor of the expression of the ZIP8 gene or the activity of the ZIP8 protein, or an inhibitor of the expression of the metal-regulatory transcription factor-1 (MTF1) gene or the activity of the MTF1 protein.

The present inventors have made intensive studies to develop pathogenesis molecular factor and therapeutic target of osteoarthritis (OA), which is a representative example of joint disease, particularly degenerative arthritis. As a result, they found out that ZIP 8 playing critical role for homeostasis of cellular $Zn^{2+}$ and MTF1 related to the ZIP 8 are closely relationship with development of OA, and joint disease may be prevented or treated through the inhibitory thereof in animal (e.g., human, mouse) cells or tissues.

ZIP is one of membrane transporters that mediate metal ions, such as $Zn^{2+}$ an influx from extracellular into cytosol as members of Slc39a (Solute-linked carrier 39a) family. There are 14 members of the ZIP family of $Zn^{2+}$ importers in mammals. $Zn^{2+}$ transporters exhibit tissue-specific functions. Abnormalities in the function of certain $Zn^{2+}$ transporters are associated with human diseases. ZIP8 as a member of this ZIP family was observed that ZIP8 protein and mRNA levels were markedly elevated in OA cartilage of human and mouse models (see: FIG. 1f).

MTF1 (metal-regulatory transcription factor-1) is well-known that induces expression of metallothioneins and other genes associated with regulating metal homeostasis in response to heavy metals, such as calcium, zinc, copper or silver, etc., as a transcription factor. When cells were exposed to heavy metals, MTF1 is accumulated in nuclear and acts to bind to promoter comprising a metal-responsive element (MRE).

The present invention primarily identifies that a zinc-ZIP8-MTF1 axis is an important regulation factor consisting of $Zn^{2+}$ influx, $Zn^{2+}$ influx factor ZIP8 and $Zn^{2+}$ dependent transcription factor MTF1, and elucidates that the joint diseases may be prevented and treated using it.

According to particular embodiment, the ZIP8 and MTF1 increases the expression of matrix-degrading enzymes in mRNA level or protein level, more specifically, increases mRNA level or protein level of MMP (matrix metalloproteinase)-3, MMP-9, MMP-12, MMP-13 and ADAMTS-5 (see: FIGS. 2a and f, FIGS. 5i and j).

According to particular embodiment, the inhibitor as an active ingredient decreases the expression of matrix-degrading enzyme in mRNA level or protein level, more particularly, the matrix-degrading enzyme is MMP (matrix metalloproteinase)-3, MMP-9, MMP-12, MMP-13 or ADAMTS (a disintegrin and metalloproteinase with thrombospondin motifs)-5.

Among the matrix-degrading enzymes, MMP-3, MMP-13 and ADAMTS-5 are known as crucial effectors of OA cartilage destruction, which exert a function by virtue of its role in degrading the extracellular matrix (ECM) of chondrocytes.

MMPs (matrix metalloproteinases) are a $Zn^{2+}$-dependent endopeptidase. These may degrade all kinds of ECM, play a critical role in cell proliferation, differentiation, migration, angiogenesis and apoptosis.

MMP-3 functions degrading collagen type II, III, IV, IX and X, proteoglycans, fibronectin, laminin and elastin, and also activates other MMP, such as MMP-1, MMP-7 and MMP-9. Therefore, MMP-3 is considered as most main factor in reconstitution of connective tissues.

MMP-9 exerts a function by virtue of its role in degrading other ECM different from collagen type IV and V, and MMP-12 in degrading elastin.

MMP-13 as collagen-degrading enzyme known as collagenase-3 in human, highly expressed in skeleton mainly, due to requirement for reconstitution of collagen matrix in fetal development stage. It was observed that the MMP-13 is highly expressed in pathological condition, in which occur carcinoma, rheumatoid arthritis and osteoarthritis.

ADAMTS-5 has two C-terminal TS motifs as a member of ADAMTS (a disintegrin and metalloproteinase with thrombospondin motifs) protein family and acts as an aggrecanase degrading an aggrecan which is main proteoglycan in cartilage.

According to particular embodiment, the composition of the present invention may include siRNA (small interference RNA), shRNA (short hairpin RNA), miRNA (microRNA), ribozyme, DNAzyme, PNA (peptide nucleic acids), anti-sense oligonucleotides, peptides, antibodies, aptamers, extracts of natural sources and chemical substances. More preferably, the composition of the present invention may include a nucleotide sequence coding ZIP8 or MTF1 protein, a sequence complementary to the nucleotide sequence, or siRNA, shRNA, miRNA, ribozyme, DNAzyme or anti-sense oligonucleotides for a fragment of the nucleotide sequence as an active ingredient.

ZIP8-encoding nucleotide sequence and MTF1-encoding nucleotide sequence used in the present invention are illustrated in SEQ ID NO:1 (GenBank Accession NO. NM_001135149) and SEQ ID NO:3 (GenBank Accession NO. NM_008636), respectively, and the sequences of amino acid of proteins expressed from each nucleotide sequence are set forth in SEQ ID NO:2 (GenBank Accession NO. NP_001128622) and SEQ ID NO:4 (GenBank Accession NO. NP_032662).

The pharmaceutical composition of the present invention comprises siRNA having sequences complementary to the nucleotide sequences as set forth in SEQ ID NO:1 (ZIP8) and SEQ ID NO:3 (MTF1) as an active ingredient.

The term used herein "siRNA" refers to a nucleic acid molecule that enables to mediate RNA interference or gene silencing (see: WO 00/44895, WO 01/36646, WO 99/32619, WO 01/29058, WO 99/07409 and WO 00/44914). The siRNA to inhibit expression of a target gene provides effective gene knock-down method or gene therapy method. The siRNA was first discovered in plant, insect, fruit fly and parasite, but recently the siRNA was applied to the study of mammalian cells (Degot S, et al. 2002; Degot S, et al. 2004; Ballut L, et al. 2005).

The siRNA molecule of the present invention may has double strand structure that the sense strand (sequence corresponding to ZIP8 or MTF1 mRNA sequence) and the antisense strand (sequence corresponding to ZIP8 or MTF1 mRNA sequence) are located on the opposite side each other to form. In addition, according to another embodiment, the siRNA molecule of the present invention may have single strand structure in which has self-complementary sense strand and antisense strand.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably 15-80 nucleotides, more preferably, 20-70 nucleotides and most preferably 20-30 nucleotides.

The siRNA may comprise either blunt or cohesive end so long as it enables to inhibit the ZIP8 or MTF1 gene expression via RNAi effect. The cohesive end may be prepared in 3'-end overhanging structure or 5'-end overhanging structure.

The siRNA molecule of the present invention may include the form that short nucleotide sequences (approximately 5-15 nt) is inserted between self-complementary sense and antisense strands. In this case, the siRNA molecule formed by the expression of the nucleotide sequence is formed hairpin structure by intramolecular hybridization, and overall stem-and-loop structure. The stem-and-loop structure is processed in vivo or in vitro to produce siRNA molecule of activity which may mediate RNAi.

The inhibition of ZIP8 or MTF1 protein in this invention, in particular the inhibitor used in inhibiting activity of the protein is preferably, an antibody or peptide binding specifically to ZIP8 or MTF1, chemicals or extracts of natural sources having small molecular weights.

The antibody inhibiting activity by binding specifically to ZIP8 or MTF1 protein used in the present invention is polyclonal or monoclonal antibody, preferably monoclonal antibody. Antibody against ZIP8 or MTF1 proteins may be prepared by a method widely known in the art, such as a hybridoma method (Kohler and Milstein, European Journal of Immunology, 6:511-519(1976)), a recombinant DNA methods (U.S. Pat. No. 4,816,56) or a phage antibody library technique (Clackson et al, Nature, 352:624-628(1991) and Marks et al, J. Mol. Biol., 222:58, 1-597(1991)). General process for antibody production is described in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; Coligan, CURRENT PROTOCOLS IN IMMUNOLOGY, Wiley/Greene, NY, 1991, and the literatures are inserted as reference in the present invention. For example, the preparation of the hybridoma cells producing monoclonal antibody is accomplished by fusing immortalized cell line with antibody-producing lymphocytes. The technology required for this process is widely known in the art and may be easily carried out using techniques. Polyclonal antibodies may be produced by injecting the ZIP8 or MTF1 protein antigen into an appropriate animal and collecting blood samples from the animal to obtain sera containing antibodies using affinity technology known in the art.

Peptide that enables to inhibit activity of ZIP8 or MTF1 by specific binding to ZIP8 or MTF1 may be obtained by a method widely known in the art, such as a display method (Smith G P, "Filamentous fusion phage: novel expression vectors that display cloned antigens on the virion surface". *Science* 228 (4705):13151317(1985); Smith G P, Petrenko V A, "Phage display". *Chem. Rev.* 97(2):391410(1997)).

Chemicals of small molecular weights inhibiting activity of ZIP8 or MTF1 may be obtained easily through screening methods described hereinafter.

The pharmaceutical composition of the present disclosure may comprise a pharmaceutically acceptable carrier. The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in *Remington's Pharmaceutical Sciences* (19th ed., 1995).

The composition of the present invention may be administered orally or parenterally. Preferably, it may be administered parenterally. When the composition of the present disclosure is administered parenterally, the pharmaceutical composition of the present disclosure may administer with intravenous injection, subcutaneous injection, local injection, intramuscular injection and intraosseous injection. More preferably, the pharmaceutical composition of the present disclosure may administer with cartilage injection.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.0001-100 mg/kg (weight).

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

A joint is the location at which bones connect. There are typically three classifications of joints: fibrous joint, cartilagenous joint and synoval joint. As joint disease, any of the diseases or injuries that affect mammal (e.g., human) joints, arthritis is no doubt the best-known joint disease, but there are also many others. Diseases of the joints may be variously short-lived or exceedingly chronic, agonizingly painful or merely nagging and uncomfortable; they may be confined to one joint or may affect many parts of the skeleton.

The term used herein "joint disease" refers to progressive deterioration or destruction of cartilage tissue surrounding joint. Arthritis is a form of joint disorder that involves inflammation of one or more joints. Particularly, osteoarthritis (OA) is the oldest and most common disease among arthritis, non-inflammatory disease showing chronic conditions characterized by destruction of joints cartilage, and also has known as degenerative joint disease, ostoarthrosis, hypertrophic arthritis or degenerative arthritis. Thus osteoarthritis referring herein may be used each other changing with other name of osteoarthritis the above-described.

Degenerative joint disease is a non-infectious progressive disorder of the weight bearing joints. The normal articular joint cartilage is smooth, white and translucent. It is composed of cartilage cells (chondrocyte) imbedded in a sponge-like middle, or matrix, made of collagen, protein polysaccharides and water. With early, primary degenerative arthritis, the cartilage becomes yellow and opaque with localized areas of softening and roughening of the surfaces.

As the degeneration progresses, the soft areas become cracked and worn exposing bone under the cartilage, which begins to remodel and increase in density while any remaining cartilage begins to fray. Eventually, osteophytes (spurs of new bone), covered by cartilage, form at the edge of the joint. Also, as mechanical wear increases, the cartilage needs repairing. The cartilage cells are unable to produce enough of the sponge-like matrix and therefore the damaged cartilage cannot repair itself. In fact, it has no blood supply to enhance healing. The majority of degenerative joint disease is the result of mechanical instabilities or aging changes within the joint. This includes old age degenerative arthritis and, in youngers, may be the result of injuries, bruises, abnormal joint configuration, (i.e. hip dysplasia), or mechanical wear from anterior cruciate ligament rupture, patellar luxation, or osteochondritis dissecans. Degenerative joint disease may be occurred in any joint of body including knees, hips, shoulders, hands and a spine.

Cartilage is the part of the joint that cushions the ends of the bones and allows easy movement of joints. The breakdown of cartilage causes the bones to rub against each other, causing stiffness, pain and loss of movement in the joint. The frequency of arthritis is a high disease to be estimated that among the Koreans adults, nearly 2 million have clinical arthritis, among US adults, nearly 27-35 million (Helmick, C., et al., Estimates of the Prevalence of Arthritis and Other Rheumatic conditions in the United States. *Arthritis & Rheumatism,* 58(1): 15-25(2008)). Unfortunately, because the cause of arthritis is not yet known, there is also no therapy. In fact, because arthritis is caused by certain factors (e.g., aging, overweight, injury, repeated overuse of certain joints, heredity, etc.), the therapy is various according to condition of developing arthritis.

Osteoarthritis is divided into various stages as follows: (a) Cartilage loses elasticity and is more easily damaged by injury or use; (b) Wear of cartilage causes changes to underlying bone. The bone thickens and cysts may occur under the cartilage. Bony growths, called spurs or osteophytes, develop near the end of the bone at the affected joint. A pruritus and pain is caused; (c) Bits of bone or cartilage float loosely in the joint space; and (d) The joint lining, or the synovium, becomes inflamed due to cartilage breakdown causing cytokines and enzymes that damage cartilage further.

In another aspect of the present invention, there is provided a method for screening a therapeutic agent for treating a joint disease, comprising: (a) contacting a test substance of interest for analysis to cells comprising (i) a ZIP8 protein or a MTF1 (metal-regulatory transcription factor-1) protein, or (ii) a nucleotide sequence encoding the ZIP8 protein or the MTF1 protein; and (b) analyzing the expression level of the ZIP8 gene, the MTF1 gene, the ZIP8 protein or the MTF1 protein, or the activity of the ZIP8 protein or the MTF1 protein, wherein where the test substance inhibits the expression level of the ZIP8 gene, the MTF1 gene, the ZIP8 protein or the MTF1 protein, or the activity of the ZIP8 protein or the MTF1 protein, it is determined as the therapeutic agent for treating joint disease.

According to the method of the present invention, first the method comprise contacting a test substance of interest for analysis to cells comprising (i) a ZIP8 protein or a MTF1 (metal-regulatory transcription factor-1) protein, or (ii) a nucleotide sequence encoding the ZIP8 protein or the MTF1 protein.

The term used herein "treatment" refers to an administration process which is possible to analyze efficacy of test substance inducing contact the test substance with cells or tissues by administrating the test substance in cells or tissues, the term enables to be used to being compatible with "administration" or "contact".

Cells including nucleotide sequences of this invention are not limited specially, specifically comprise mammal cells, more specifically joint-derived cells, but are not limited thereto. According to particular embodiment, the cells that enable to be used in the present invention are joint-derived cells, more preferably articulating joints-derived cells. According to particular embodiment, the articulating joint tissue that enables to be used in the present invention includes wrists, elbows, shoulders, ankles, knees, hips, spine, temporomandibular and Carpometacarpal joints, but not limited to. More preferably, joint tissue is derived from femoral heads, femoral condyles, tibial plateaus, acetabulofemoral joint, acromioclavicular joint, femoropatellar joint, femorotibial joint, glenohumeral joint, humeroradial joint, humeroulnar joint, interphalangeal joint, metacarpal joint, radioulnar joint and talocrural joint, but is not limited to.

The method of the present invention further comprises (pre-a) causing joint diseases to the cells. For example, analysis of stage described below is enabled to perform more clearly by causing joint diseases condition to cells through mechanical stress like DMM surgery or injection of pro-inflammatory cytokine like IL-1 or virus. According to certain embodiment, the adenovirus of the present invention carries out through intraarticular (IA) injection or intraperitoneal (IP) injection.

The term "test substance" used herein in conjunction with the present screening method refers to a material tested in the present method for analyzing the influence on the activity of ZIP8 or MTF1 protein. The test substance includes chemical substances, siRNA (small interference RNA), shRNA (small hairpin RNA or short hairpin RNA), miRNA (microRNA), ribozyme, DNAzyme, PNA (peptide nucleic acids), antisense oligonucleotides, peptides, antibodies, aptamers and extracts of natural sources, but not limited to. The test material analyzed by the screening method of the present invention is a single compound or a mixture of compounds (e.g., a natural extract or a cell or tissue culture). The test material may be obtained from synthetic or natural compound libraries. These compound libraries are obtained by methods known in the art. The synthetic compound libraries are commercially available from Maybridge Chemical Co. (UK), Comgenex (USA), Brandon Associates (USA), Microsource (USA) and Sigma-Aldrich (USA), and the natural compound libraries are commercially available from Pan Laboratories (USA) and MycoSearch (USA). The test material may be obtained from various combinational library methods known in the art, for example, from a biological library method, a spatially addressable parallel solid phase or solution phase library method, a synthetic library method requiring deconvolution, a "one-bead one-compound" library method, and a synthetic library method using affinity chromatography selection. The synthetic methods of molecular libraries are disclosed in DeWitt et al., *Proc. Natl. Acad. Sci. U.S.A.* 90: 6909 (1993); Erb et al. *Proc. Natl. Acad. Sci. U.S.A.* 91: 11422 (1994); Zuckermann et al., *J. Med. Chem.* 37: 2678 (1994); Cho et al., *Science* 261: 1303 (1993); Carell et al., *Angew. Chem. Int. Ed. Engl.* 33: 2059 (1994); Carell et al., *Angew. Chem. Int. Ed. Engl.* 33: 2061; and Gallop et al., *J. Med. Chem.* 37: 1233 (1994).

Then, the measurement of the expression level of ZIP8 or MTF1 gene or protein, or activity of their proteins is conducted in cells treated the test substance. As a result, where the test substance down-regulates the expression of their gene or protein, or the activity of their proteins, it is determined as the therapeutic agent for preventing or treating joint disease.

According to particular embodiment, the substance for preventing or treating of joint disease discovered by the above described screening method may be used in treatment or prevention of ostarthritis, degenerative arthritis, osteochondritis dissecans, arthroses or arthritis after articular crescent meniscus injury, malalignment of joint, avascular necrosis, arthroses, isolated chondral defect, chondromalacia patellae, synovitis, bursitis, traumatic effusion, ligamentous deficiency arthroses, osteochondritis dissecans (OCD), patellar instability, rheumatoid arthritis, juvenile idiopathic arthritis, juvenile arthritis, post-traumatic arthritis, inflammatory arthritis, septic arthritis, lupus, scleroderma, tendinitis, fibrositis, fibromyositis or polymyositis, but not limited thereto.

In the case of performing the screening method of this invention by analyzing expression of ZIP or MTF1, the measurement of change in the expression level of ZIP8 or MTF1 afore-mentioned may be carried out through a variety of methods known in the art, for example, RT-PCR (Sambrook et al, *Molecular Cloning. A Laboratory Manual*, 3rd ed. Cold Spring Harbor Press (2001)), Northern blot (Peter B. Kaufma et al., *Molecular and Cellular Methods in Biology and Medicine*, 102-108, CRC press) or hybridization using cDNA microarray (Sambrook et al, *Molecular Cloning. A Laboratory Manual*, 3rd ed. Cold Spring Harbor Press (2001)).

According to RT-PCR protocol, total RNA is extracted from the test substance-treated cells, and first strand cDNA is prepared using oligo dT primer and reverse transcriptase. Then, PCR reaction is carried out using first strand cDNA as a template and a gene encoding the ZIP8 or MTF1 protein-specific primer set. The resulting products are separated by electrophoresis and the band patterns are analyzed to measure the expression level of the gene of ZIP8 or MTF1 protein.

The change of level of ZIP8 or MTF1 protein may be performed by a variety of quantitative or qualitative immunoassay protocols. The immunoassay format includes, but is not limited to, immunohistochemical staining, radioimmunoassay analysis, radioactive immunoprecipitation, western blotting, immunoprecipitation, ELISA (enzyme-linked immunosorbant assay), Capture-ELISA, sandwich assay, flow cytometry, immunofluorescence and immune affinity purified.

The immunoassay or the immuno staining method is described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Laboratory Press, 1999 and the literatures are inserted as reference in herein.

When the method of the present disclosure is performed using the ELISA, certain examples of the present invention comprise the steps of: (i) coating unknown cell cytolysate samples of interest for analysis on the surface of a solid substrate; (ii) contacting the cell cytolysate with antibody for the marker as the primary antibody; (iii) contacting the resultant of step (ii) with the secondary antibody conjugated enzyme; and (iv) detecting the enzyme activity.

The appropriate solid substrate is hydrocarbon polymers (e.g., polystyrene and polypropylene), glass, metal, or gel, and most preferably a micro-titer plate.

The appropriate secondary antibody conjugated enzyme includes, but is not limited to, color-developing reaction, fluorescent reaction, luminescent reaction or infrared reaction, for example, alkaline phosphatase, β-galactosidase, horseradish peroxidase, luciferase and cytochrome P450. Where alkaline phosphatase is used for the enzyme binding to the secondary antibody, bromochloroindolylphosphate (BCIP), nitro blue tetrazolium (NBT), naphthol-AS-B1-phosphate and ECF (enhanced chemifluorescence) may be used as a substrate for color-developing reactions. In the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphtol/pyronine may be used as a substrate; and in the case of using glucose oxidase, t-NBT (nitroblue tetrazolium) or m-PMS (phenzaine methosulfate) may be used as a substrate.

When the method of the present disclosure is performed using the Capture-ELISA, certain examples of the present invention comprise the steps of: (i) coating the antibody for the target (e.g., ZIP8 or MTF1 protein) of the present invention as capturing antibody on the surface of a solid substrate; (ii) contacting the cell sample with the capturing antibody; (iii) contacting the resultant of step (ii) with the detecting antibody which is combined with label generating signal and react specifically to the ZIP8 or MTF1 protein; and (iv) detecting the signal from the label. The detecting antibody has the label generating detectable a signal. The label includes, but is not limited to, chemical (e.g., biotin), enzyme (alkaline phosphatase, β-galactosidase, horseradish peroxidase and cytochrome P450), radioactive material (e.g., $C^{14}$, $I^{125}$, $P^{32}$ and $S^{35}$), fluorescent material (e.g., fluorescein), luminescent material, chemiluminescent material and FRET (fluorescence resonance energy transfer). A variety of labels and labeling methods are described in Ed. Harlow and David Lane, Using Antibodies: A Laboratory Manual, Cold Spring Harbor Laboratory Press, 1999.

The final measurement of enzyme activity or measurement of the signal in the ELISA and Capture-ELISA may be carried out in accordance with a variety of methods known in the art. The detection of this signal permits to qualitative or quantitative analysis of the target of the present invention. In the case of using biotin as label, the signal is easily detected using streptavidin. In the case of using luciferase as label, the signal is easily detected using luciferin.

When the screening method of the present invention is performed analyzing the activity of ZIP8 or MTF1, the activity of ZIP8 may be analyzed by measuring cellular $Zn^{2+}$ level. According to a certain embodiment, when IL-1 is treated in chondrocyte, cellular $Zn^{2+}$ level increases along with increasing of expression level of ZIP8 at the same time. However, when Zip-siRNA is treated in chondrocyte, increasing effect of $Zn^{2+}$ level is blocked. Thus, if some test substance inhibits the activity of ZIP8 protein, it may be predicted to be unlikely to increase cellular $Zn^{2+}$ level by being blocked cellular $Zn^{2+}$ influx.

In addition, the activity of MTF1 protein may be analyzed by measuring a transcription activity of MTF1 using commercially available transcription factor activity analysis kit. According to a certain embodiment, when chondrocyte is infected with Ad-Zip8, it presents that transcription activity of MTF1 increase more than three fold.

In still another aspect of the present invention, there is provided a method for detecting a joint disease in a subject, comprising: (a) providing a biological sample from the subject; and (b) measuring the expression level of the ZIP8 gene, the MTF1 gene, the ZIP8 protein or the MTF1 protein, relative to the expression level of the ZIP8 gene, the MTF1 gene, the ZIP8 protein or the MTF1 protein in a control sample from a normal subject, wherein an increased level of the ZIP8 gene, the MTF1 gene, the ZIP8 protein or the MTF1 protein in the biological sample compared to the control sample indicates that the subject has the joint disease.

The molecular marker of this invention may be indicative of a joint disease, and also used in diagnosis of the joint disease development or progression, or prognosis.

The term used herein "Biosample or biological sample" is a human body or mammal-originated sample of material to be tested. The biosample refers to any cell or tissue from a cartilage (particularly, articular cartilage), urine, saliva, blood, plasma, or serum, but is not limited thereto. Preferably, ZIP8 or MTF1 of the present invention is comprised in a cartilage, particularly, articular cartilage. Accordingly, because ZIP8 or MTF1 of the present invention may be an indicator for pathogenesis or development of arthritis, ZIP8 or MTF1 can be used to diagnosis of pathogenesis or development of arthritis.

According to an embodiment, ZIP8 or MTF1 of the present invention may be used to prediction or diagnosis of osteoarthritis, degenerative joint disease, osteochondritis dissecans, ligamentinjuries, meniscus injuries, malalignment of joint, osteonecrosis, rheumatoid arthritis, juvenile idiopathicarthritis, trauma, inflammatory arthritis or septic arthritis by infection, more particulalry, osteoarthritis or degenerative joint disease, most preferably, very accurate prediction or diagnosis of osteoarthritis.

The term used herein "detecting a joint disease" includes the following matters: (a) to determine susceptibility of a subject to a particular disease or disorder; (b) to evaluate whether a subject has a particular disease or disorder; (c) to assess a prognosis of a subject suffering from a specific disease or disorder (e.g., identification of arthritis conditions, determination of arthritis stage, or investigation of arthritis response to treatment); or (d) therametrics (e.g., monitoring conditions of a subject to provide an information to treatment efficacy).

The term as used herein "prognosis" includes prediction in terms of the progression possibility process of the disease, in particular, the improvement of the disease, the regeneration of the disease and arthritis recurrence. Preferably, the prognosis of the present invention refers to completely cured possibility for the disease of arthritis patients.

Following preparation of biological samples, the ZIP8 gene, the MTF1 gene, the ZIP8 protein or the MTF1 protein in the biological sample is detected, relative to the expression level of the ZIP8 gene, the MTF1 gene, the ZIP8 protein or the MTF1 protein in a control sample from a normal subject, wherein an increased level of the ZIP8 gene, the MTF1 gene, the ZIP8 protein or the MTF1 protein in the biological sample compared to the control sample indicates that the subject has the joint disease.

A "control sample" refers to a sample of biological material representative of healthy, joint disease-free animals, and/or cells or tissues. The level of ZIP8 or MTF1 in a control sample is desirably typical of the general population of normal, joint disease-free animals or of a particular individual, or in a particular tissue. A control sample can also refer to an established level of ZIP8 or MTF1, representative of the joint disease-free population, that has been previously established based on measurements from normal, joint disease-free animals.

An "increased level of ZIP8 or MTF1" means a level of ZIP8 or MTF1 that, in comparison with a control level of ZIP8 or MTF1, is detectably higher. The method of comparison can be statistical, using quantified values for the level of ZIP8 or MTF1, or can be compared using non-statistical means, such as by visual assessment by a human.

The biomarkers of the present invention are biomolecules expressed highly in arthritis. The high expression of biomarkers may be measured at mRNA or protein level. The term "high expression" means that the nucleotide sequence of interest in a sample to be analyzed is much more highly expressed than that in the normal sample, for instance, a case analyzed as high expression according to analysis methods known to those skilled in the art, e.g., RT-PCR method or ELISA method (See, Sambrook, J., et al., *Molecular Cloning. A Laboratory Manual,* 3rd ed. Cold Spring Harbor Press (2001)). Using analysis methods as described above, where the biomarkers of the present invention are much more highly expressed at a range of 2-5 folds than in normal cells tissues, this case is determined as "high expression" and identified as development of arthritis in the present invention.

According to particular embodiment, the measurement of the expression level is performed by RT-PCR (reverse transcription-polymerase chain reaction) or an immunoassay.

Since the method of the present invention comprises the process of analyzing the expression levels of ZIP8 or MTF1 gene or protein described above, the common descriptions between the screening methods of the present invention described above are omitted in order to avoid undue redundancy leading to the complexity of this specification.

In the diagnosis or prognosis analysis using the present invention, when the expression of nucleotide sequence encoding ZIP8 or MTF1 protein is detected, probes or primers used in the present invention have a complementary sequence to the nucleotide sequence of ZIP8 or MTF1.

The nucleic acid sample to be analyzed may be prepared using mRNA from various biosamples. Preferably, the biosample is articular cartilage tissue cells.

The present kit for diagnosing joint disease may be used in accordance with hybridization. For such analysis, probes, which have a complementary sequence to the nucleotide sequence of the biomarkers of this invention as set forth, are used. Using probes hybridizable with the nucleotide sequence of the biomarkers of this invention, arthritis may be determined by hybridization-based assay.

Labels linking to the probes may generate a signal to detect hybridization and bound to oligonucleotide. Suitable labels include fluorophores (e.g., fluorescein, phycoerythrin, rhodamine, lissamine, Cy3 and Cy5 (Pharmacia)), chromophores, chemiluminescents, magnetic particles, radioisotopes (e.g., $P^{32}$ and $S^{35}$), mass labels, electron dense particles, enzymes (e.g., alkaline phosphatase or horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation, random priming (Multiprime DNA labeling systems booklet, "Amersham" (1989)) and kination (Maxam & Gilbert, *Methods in Enzymology,* 65: 499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

Probes are hybridized with cDNA molecules under stringent conditions. Suitable hybridization conditions may be routinely determined by optimization procedures. To establish a protocol for use of laboratory, these procedures may be carried out by various methods known to those ordinarily skilled in the art. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999). For example, the high stringent condition includes hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Following hybridization reactions, a hybridization signal indicative of the occurrence of hybridization is then measured. The hybridization signal may be analyzed by a variety of methods depending on labels. For example, where probes are labeled with enzymes, the occurrence of hybridization may be detected by reacting substrates for enzymes with hybridization resultants. The enzyme/substrate pair useful in this invention includes, but is not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphtol/pyronine; a pair of alkaline phosphatase and bromochloroindolylphosphate (BCIP), nitro blue tetrazolium (NBT), naphthol-AS-B1-phosphate and ECF substrate; and a pair of glucose oxidase and t-NBT (nitroblue tetrazolium) or m-PMS (phenzaine methosulfate). Where probes are labeled with gold particles, the occurrence of hybridization may be detected by silver staining method using silver nitrate. In these connections, where the present method for determining joint disease makers is carried out by hybridization, it comprises the steps of: (i) hybridizing a nucleic acid sample to a probe having a nucleotide sequence complementary to the nucleotide sequence of the biomarker of this invention as set forth; and (ii) detecting the occurrence of hybridization. The signal intensity from hybridization is indicative of joint disease. When the hybridization signal to the biomarker of this invention from a sample to be diagnosed is measured to be stronger than normal samples (e.g., normal tissues or cells from articular cartilage), the sample can be determined to have joint disease.

According to particular embodiment, the kit for diagnosing joint disease of human of this invention may be a kit for gene amplification. According to particular embodiment, the kit of the present invention is carried out using a real-time PCR. The real-time PCR is a technique which analyzes monitoring an increasing of PCR product in real time (Levak K J, et al., *PCR Methods Appl.*, 4(6): 357-62(1995)).

In still another aspect of the present invention, there is provided a non-human transgenic animal model for joint disease comprising an expression construct comprising (a) a nucleotide sequence encoding ZIP8 or MTF1; and (b) a transcription-regulating sequence operatively linked to the nucleotide sequence.

According to the present invention, after a transformed fertilized egg obtains micro-injecting the recombinant expression vector of the present invention in a fertilized egg, the transformed fertilized egg implants in uterus of surrogate mother (e.g., mouse), followed by preparing a transformed animal through PCR genetic test obtaining a next generation animal (e.g., mouse).

The present invention prepares the transformed animal (specifically, mouse) using recombinant expression vector (expression construct) comprising ZIP8 or MTF1, which is a target factor for inducing of joint diseases, and the transformed animal is provided with an animal model system for studying of joint diseases.

The recombinant expression vector of the present invention comprises the nucleotide sequence as set forth in SEQ ID NO:1 (ZIP8) or SEQ ID NO:3 (MTF1). More detailed, the recombinant expression vector comprises (a) a construct comprising an expression substance of interest-encoding nucleotide sequence; (b) a promoter which is operatively linked to the construct and act in animal cells to form RNA molecule, more preferably (a) a construct comprising a nucleotide sequence encoding amino acid sequence as set forth in SEQ ID NO:2 (ZIP8) or SEQ ID NO:4 (MTF1); (b) a transcription-regulating sequence which is operatively linked to the construct, still more preferably (a) a construct comprising a nucleotide sequence encoding amino acid sequence as set forth in SEQ ID NO:2 (ZIP8) or SEQ ID NO:4 (MTF1); (b) a transcription-regulating sequence which is operatively linked to the construct; and (c) a poly A signal causing polyadenylation at the 3'-end of a RNA molecule which act in animal cells, most preferably (a) a construct comprising a nucleotide sequence encoding the nucleotide sequence as set forth in SEQ ID NO:1 (ZIP8) or SEQ ID NO:3 (MTF1); (b) a Col2a1 promoter and enhancer sequence which is operatively linked to the construct; and (c) a poly A signal causing polyadenylation at the 3'-end of a RNA molecule which act in animal cells.

The mRNA level or the protein level of the expression of the nucleotide sequence as set forth in SEQ ID NO:1 (ZIP8) or SEQ ID NO:3 (MTF1) which is included the recombinant vector of the present invention is increased in cells (e.g., chondrocytes) or tissues (e.g., the transgenic mouse cartilage tissue in the present invention) so that researches associated with arthritis have usability in animals (preferably mouse). In addition, it may become apparent to those skilled in this art that variants of nucleotide sequence encoding ZIP8 or MTF1 belong to the present invention. In other words, it may become apparent to those skilled in this art that variants fused with marker for detecting target protein belong to the present invention. For example, the protein which may be fused to target protein for detecting target protein includes, but not limited to, GFP (green fluorescent protein), RFP (red fluorescent protein), CFP (cyan fluorescent protein) and YFP (yellow fluorescent protein), BFP (bluefluorescent protein), luciferase or its variants (e.g., EGFP, ECFP, EYFP, ERFP, EBFP).

The term used herein "transcription-regulating sequence or promoter" means a DNA sequence that regulates the expression of a coding sequence or a functional RNA. In the recombinant expression vector of the present invention, the expression substance of interest-encoding nucleotide sequence is operatively linked to the promoter. The term "operatively linked" refers to functional linkage between a nucleic acid expression control sequence (such as a promoter, signal sequence, or array of transcription-regulating factor binding sites) and a second nucleic acid sequence, wherein the expression control sequence affects transcription and/or translation of the nucleic acid corresponding to the second sequence.

According to particular embodiment, the transcription-regulating sequence further comprises an enhancer.

According to the present invention, transcription-regulating sequence operatively linked to nucleotide sequence encoding ZIP8 or MTF1 gene is operable in, preferably, animal cells, more preferably, mammalian cells, to control transcription of the ZIP8 or MTF1 gene, including the promoters derived from the genome of mammalian cells or from mammalian viruses, for example, Col2a1 promoter, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, tumor cell specific promoter (e.g., TERT promoter, PSA promoter, PSMA promoter, CEA promoter, E2F promoter and AFP promoter) and tissue specific promoter (e.g., albumin promoter). Most preferably, the promoter is Col2a1 promoter.

According to particular embodiment, the promoter of present invention is a chondrocyte-specific promoter and more preferably, the present invention further comprise the enhancer, most preferably the chondrocyte-specific enhancer of Col2a1.

According to particular embodiment, the expression construct of the present invention further comprises an intron sequence between the promoter and the nucleotide sequence encoding ZIP8 or MTF1. Preferably, the expression constructs used in the present invention comprises polyadenylated sequence (e.g., bovine growth hormone terminator and polyadenylated sequence derived from SV40).

According to particular embodiment, the construct comprising ZIP8 or MTF1-encoding nucleotide sequence used in the present invention has the structure of "transcription-regulating sequence-ZIP8 or MTF1-encoding nucleotide sequence-polyadenylated sequence".

Effects of this Invention

The features and advantages of the present invention will be summarized as follows:

(a) The present invention relates to identification of Zinc-ZIP8-MTF1 axis that plays an important role to OA (osteoarthritis) pathogenesis process and a novel use thereof.

(b) According to the present invention, ZIP8 and MTF1 of the present invention increase in the expression in joint disease induced cells or cartilage tissue, and induce the expression of various matrix-degrading enzymes (e.g., MMP-3, MMP-9, MMP-12, MMP-13 and ADAMTS-5 etc.).

(c) In addition, when the expression of ZIP8 or MTF1 is inhibited in cells or tissues of animals (e.g., human, mouse), OA pathogenesis is inhibited.

(d) Therefore, the ZIP8 and MTF1 of the present invention may be applied to the diagnosis or prognosis of joint diseases, and may be used for the development of therapeutics for joint diseases using these.

BRIEF DESCRIPTION OF THE DRAWINGS

FIG. 1a represents mRNA levels of metal ion transporters determined by qRT-PCR in articular chondrocytes treated with IL1β (n=10). Insert is Western blotting of ZIP8 in chondrocytes treated with IL1β.

FIG. 1b shows that cellular levels of $Zn^{2+}$, $Fe^{2+}/Fe^{3+}$, $Mn^{2+}$, and $Cd^{2+}$ were measured in chondrocytes infected with Ad-C or Ad-Zip8 following treatment with indicated concentrations of $ZnCl_2$, $FeCl_2$, $MnCl_2$, or $CdCl_2$.

FIG. 1c shows that cellular $Zn^{2+}$ levels were imaged and quantified in chondrocytes treated with ZnCl2 or IL1β, with or without control or Zip8 siRNA, or in chondrocytes infected with Ad-Zip8, with or without the metal chelator, CaEDTA or TPEN (n=5-12).

FIG. 1d represents that cellular $Zn^{2+}$ levels were quantified in chondrocytes infected with Ad-Zip8, with or without therapeutic ZIP8 antibodies.

FIGS. 1e and 1f represent staining of cartilage with alcian blue or safranin-O, imaging and quantification of $Zn^{2+}$ levels with fluorophore, detection of ZIP8 by immunostaining, and quantification of ZIP8 mRNA levels by qRT-PCR in human OA cartilage (FIG. 1e) or mouse OA cartilage induced by DMM surgery (FIG. 1f) (n≥8).

Scale bar: 50 μm. Values are presented as means±SEM (*P<0.05, P<0.01, *P<0.001). NS, not significant.

FIGS. 2a to 2f represent that ZIP8-mediated $Zn^{2+}$ influx induces upregulation of matrix-degrading enzymes in chondrocytes.

Figure 2A:
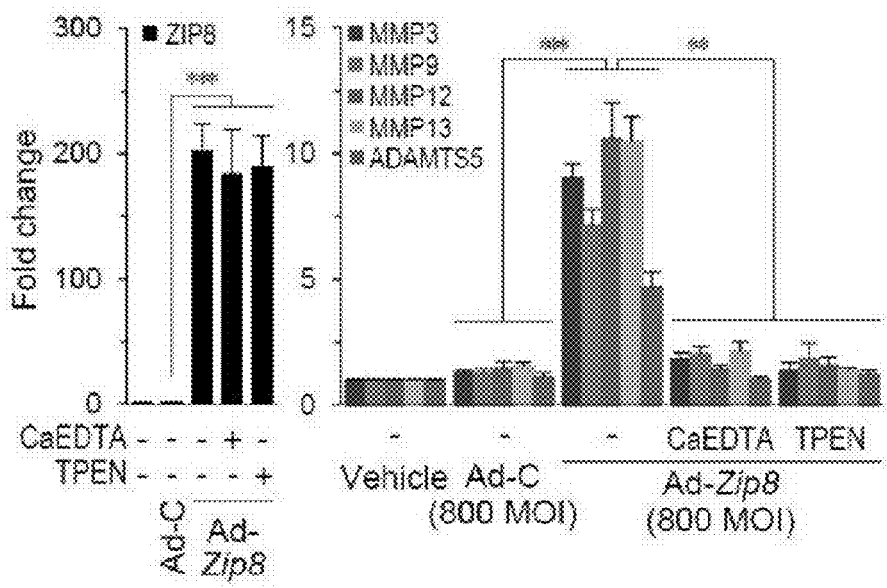
Figure 2B:
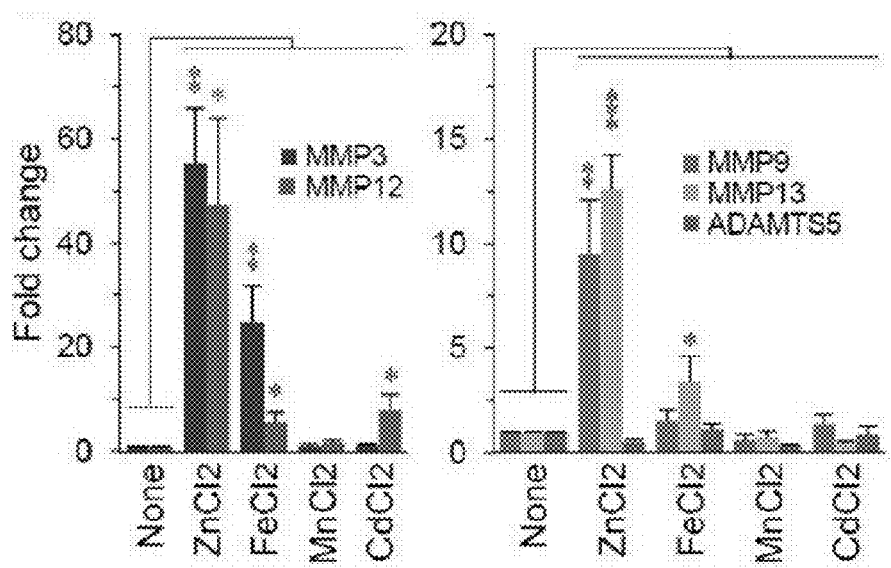

FIGS. 2a and 2b show that mRNA levels were quantified by qRT-PCR in chondrocytes infected with Ad-C or Ad-Zip8, with or without CaEDTA or TPEN (n≥6) (FIG. 2a) or treated with 100 μM of $ZnCl_2$, $FeCl_2$ or $MnCl_2$ and 1 μM of $CdCl_2$ (n=6) (FIG. 2b).

Figure 2C:
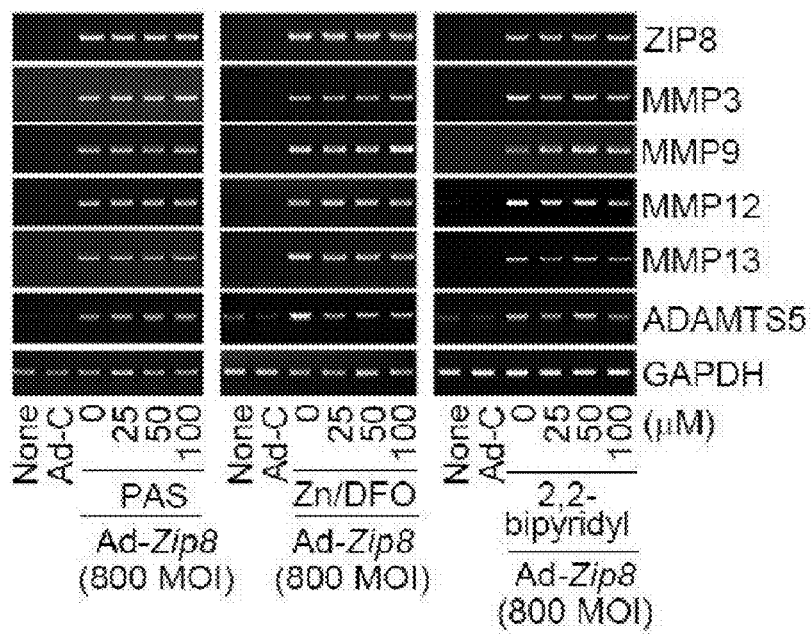

FIG. 2c represents that the indicated mRNAs were detected in chondrocytes infected with Ad-C or Ad-Zip8 in the absence or presence of the indicated concentrations of iron chelators, Zn/DFO, 2,2-bipyridyl, or $Mn^{2+}$ chelator para-aminosalicylic acid (PAS) (n=4).

Figure 2D:
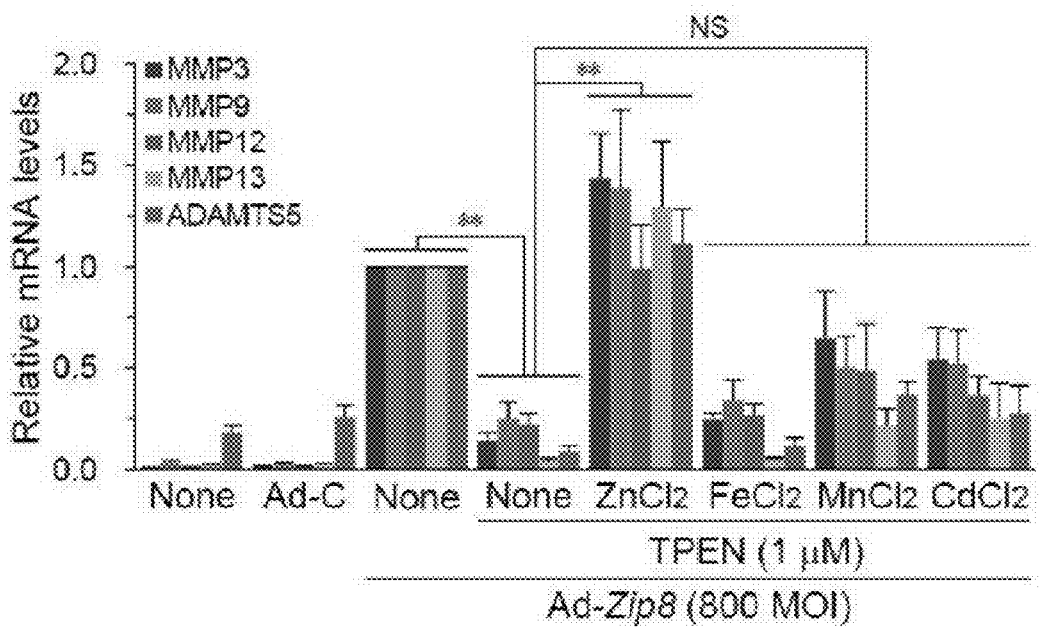

FIG. 2d shows mRNA levels of matrix-degrading enzymes in chondrocytes infected with Ad-C or Ad-Zip8 with or without TPEN (1 μM) or TPEN pre-incubated with 1 μM of the indicated metal ion (n=5).

Figure 2E:
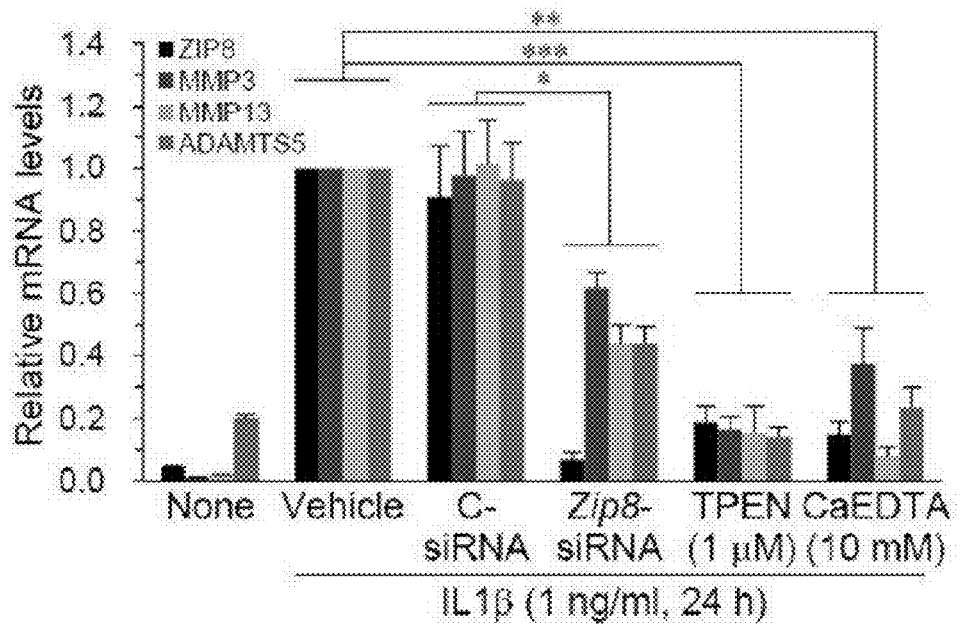

FIG. 2e shows qRT-PCR analysis (n≥6) of mRNA levels of ZIP8 and matrix-degrading enzymes in chondrocytes treated with IL1β, with or without control or Zip8 siRNA, TPEN, or CaEDTA.

Figure 2F:
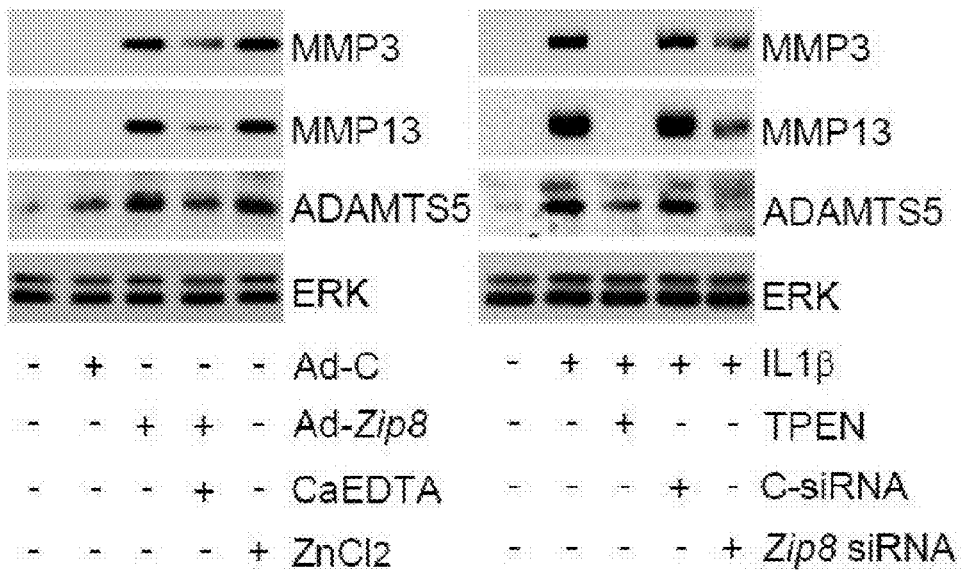

FIG. 2f represents expression of matrix-degrading enzymes, determined by Western blotting.

Values are presented as means±SEM (*P<0.05, P<0.01, *P<0.001).

Figure 3A:
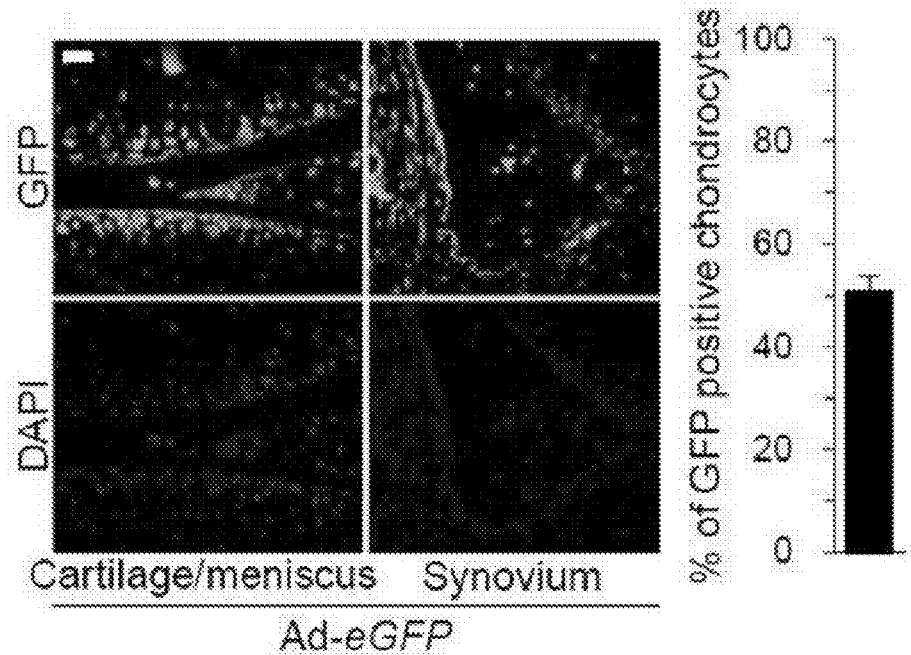
Figure 3B:
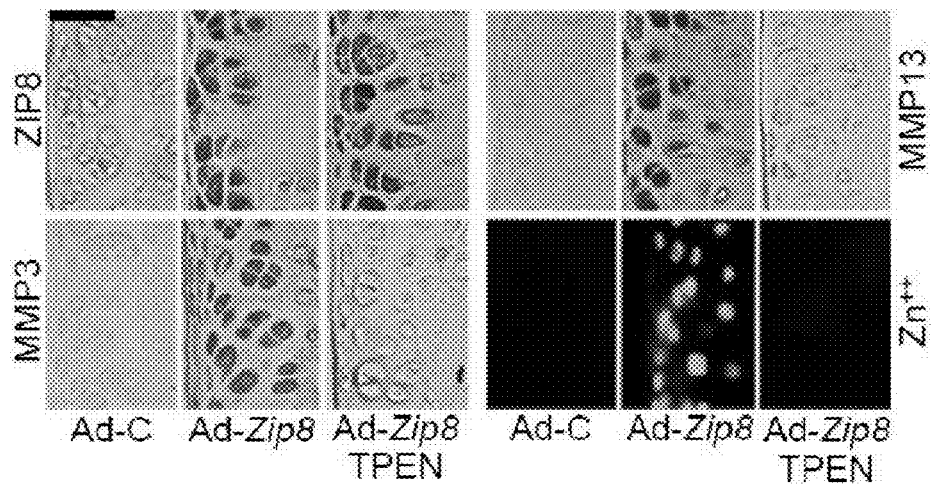
Figure 3C:
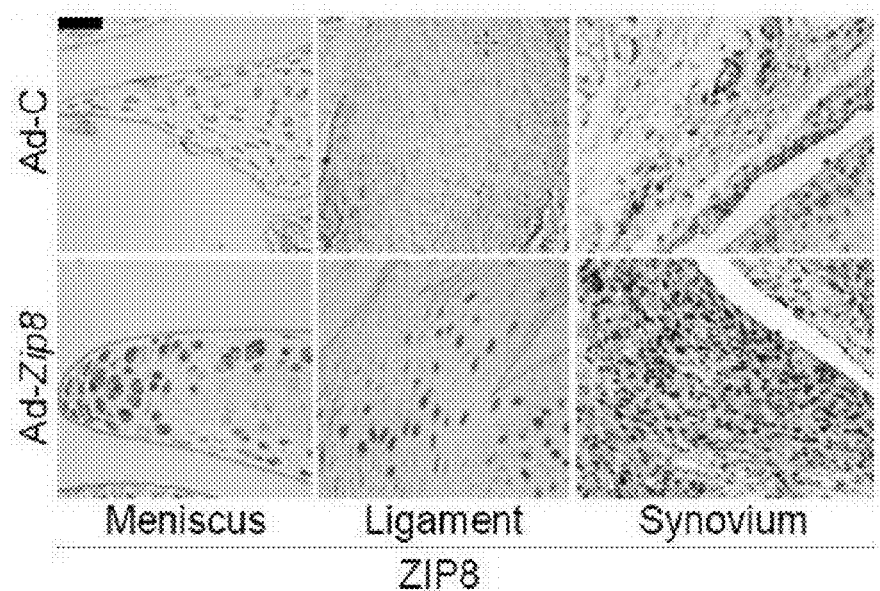
Figure 3D:
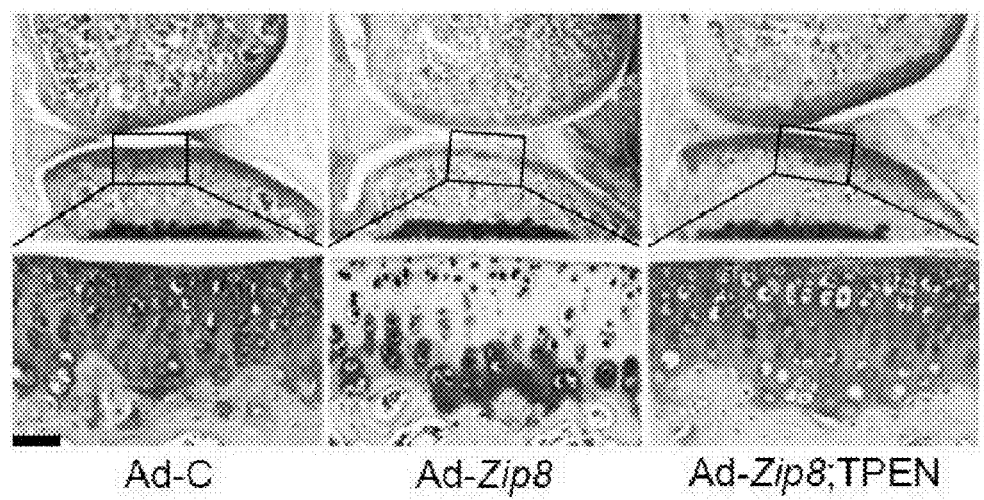
Figure 3E:
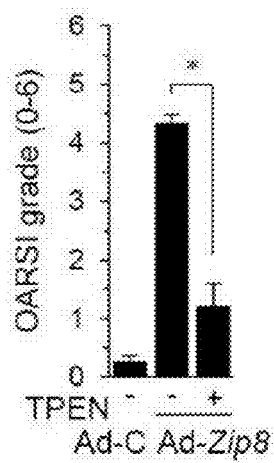
Figure 3F:
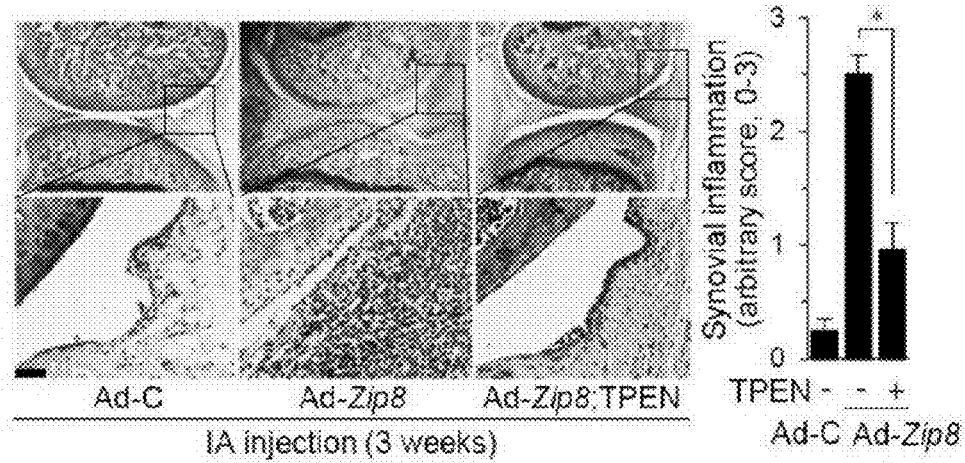
Figure 3G:
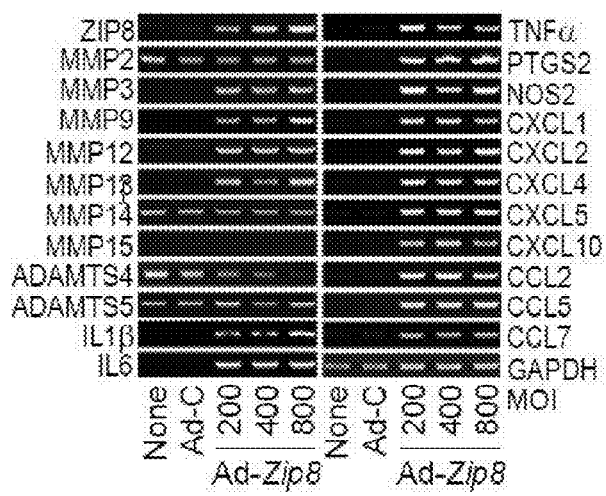
Figure 3H:
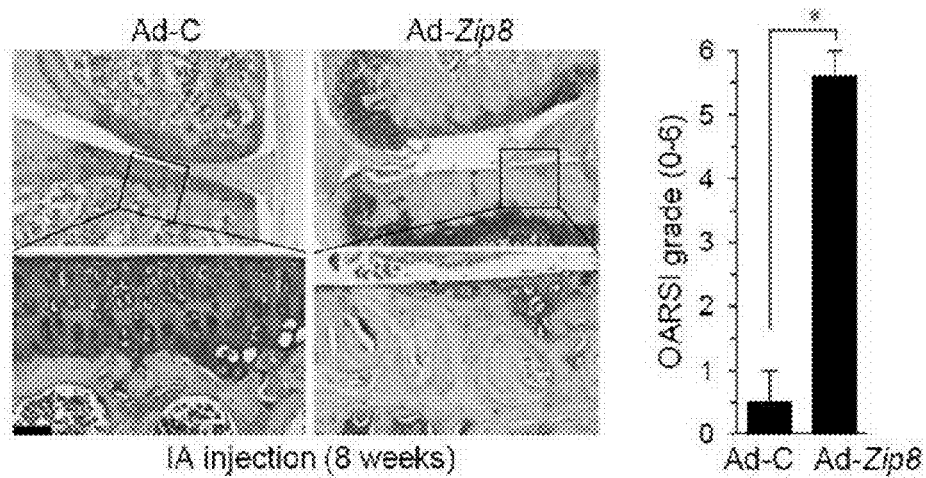
Figure 3I:
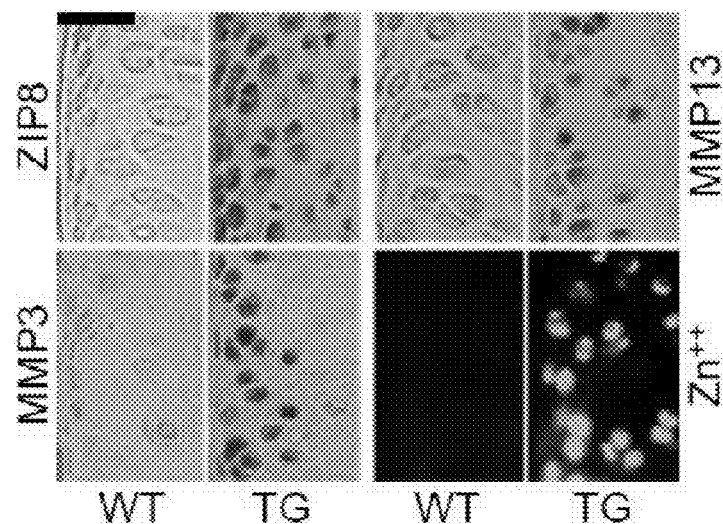
Figure 3J:
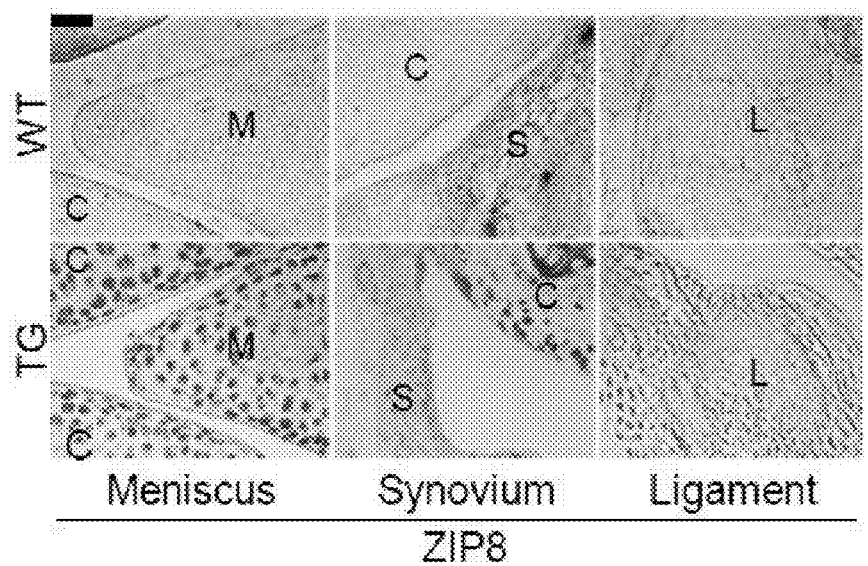
Figure 3K:
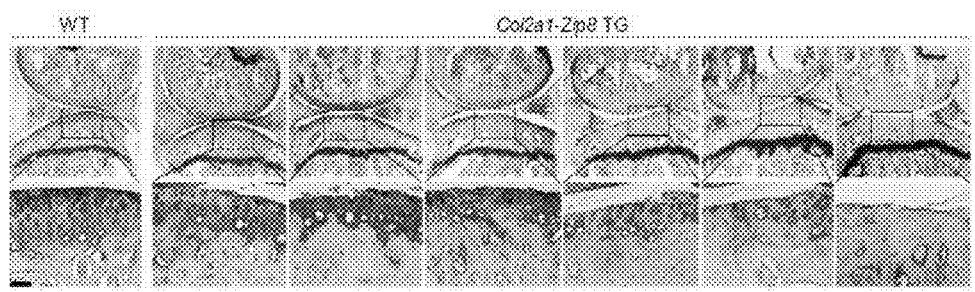
Figure 3L:
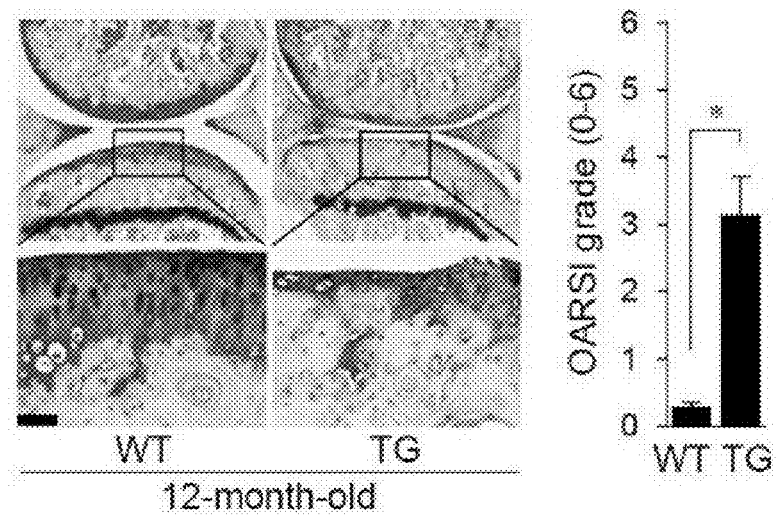
Figure 3M:
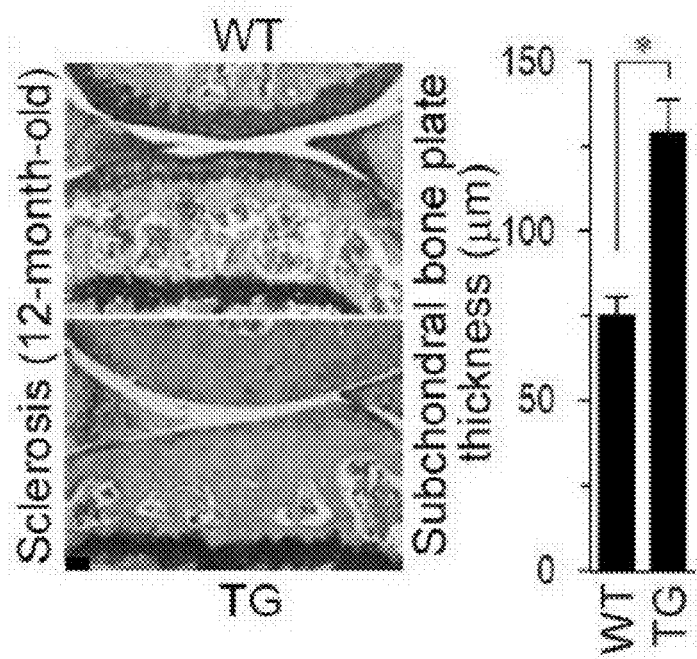
Figure 3N:
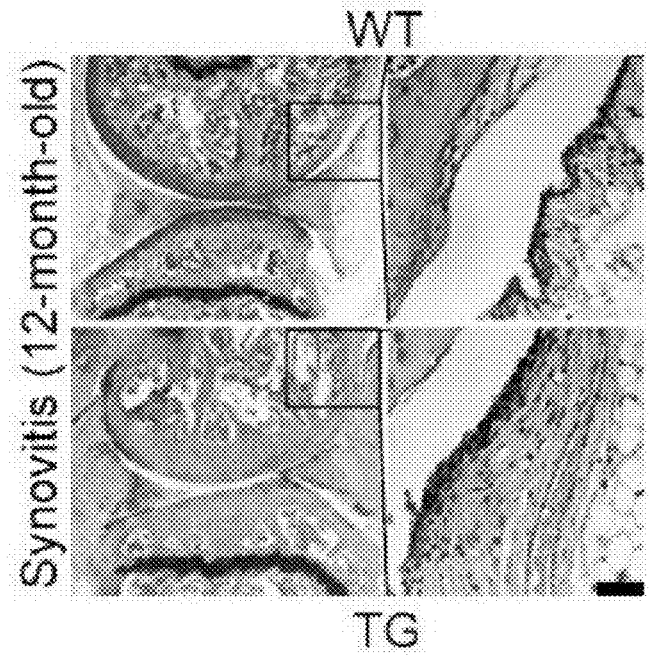
Figure 3O:
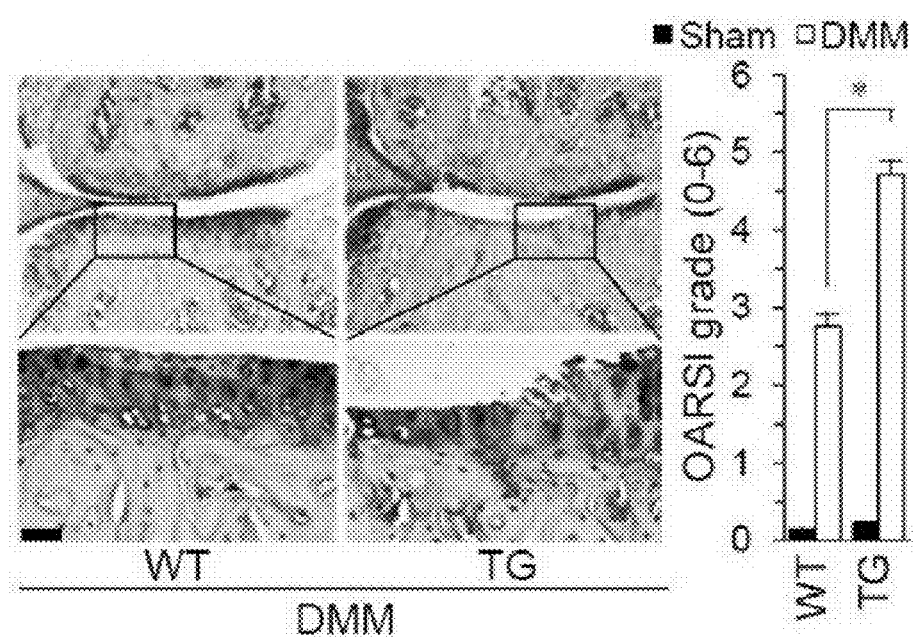
Figure 3P:
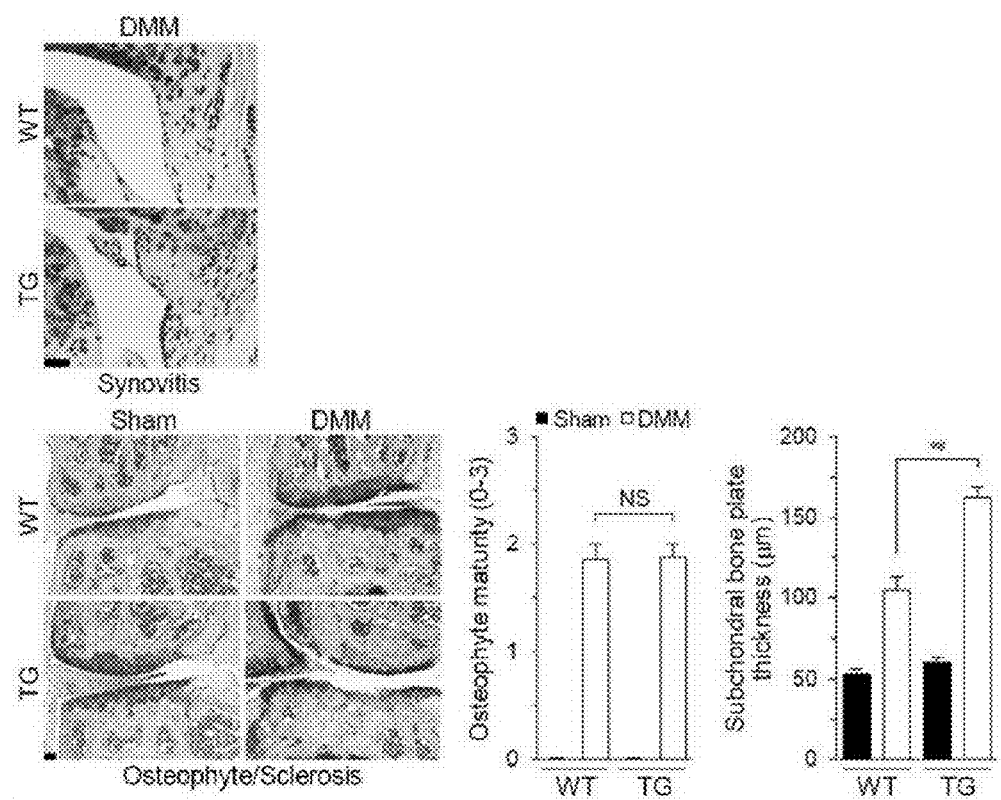

FIGS. 3a to 3p represent that ZIP8 overexpression in cartilage tissue causes OA pathogenesis in mice.

FIG. 3a shows that mice were IA-injected with Ad-eGFP (1×10⁹ PFU, once per week for 3 weeks) and sacrificed 21 days after the first injection. GFP was visualized by fluorescence microscopy of the joint sections (left). The percentages of GFP-positive chondrocytes were quantified (n=5) (right).

FIG. 3b shows that after mice were IA-injected with Ad-C or Ad-Zip8 with or without TPEN, ZIP8, MMP3, and MMP13 in cartilage were detected by immunostaining, and $Zn^{2+}$ was imaged using a fluorophore.

FIG. 3c represents that mice were IA-injected with Ad-C or Ad-Zip8 ($1\times10^9$ PFU, once per week for 3 weeks) and sacrificed 21 days after the first injection. ZIP8 protein in the meniscus, ligament, and synovium was detected by immunostaining.

FIGS. 3d and 3e represent that cartilage destruction was detected by safranin-O staining (FIG. 3d) and quantified by OARSI grade (n≥13) (FIG. 3e). FIG. 3f shows that mice were IA-injected with Ad-Zip8 ($1\times10^9$ PFU, once per week for 3 weeks) alone or coinjected with TPEN (0.1 mg/kg body weight). Mice were sacrificed 21 days after the first injection. Synovitis was determined by safranin-O/hematoxylin staining and quantified (n≥13).

FIG. 3g shows that primary cultures of mouse fibroblast-like synoviocytes were infected with Ad-C (800 MOI), Ad-Zip8 (at the indicated MOI) for 2 hours or were left untreated, and then were incubated for an additional 24 hours. The indicated mRNAs were detected by RT-PCR (n=4).

FIG. 3h represents that mice were IA-injected with Ad-Zip8($1\times10^9$ PFU, once per week for 3 weeks) and sacrificed 8 weeks after the first injection. Cartilage destruction, subchondral bone sclerosis, and osteophyte maturity were determined by safranin-O staining and quantified (n=10).

FIG. 3i shows that cartilage sections from 12-week-old WT and Zip8 TG mice were immunostained for ZIP8, MMP3, and MMP13. $Zn^{2+}$ was imaged using a fluorophore.

FIG. 3j shows that ZIP8 protein in the meniscus, ligament, and synovium of Col2a1-Zip8 TG mice and WT littermates was detected by immunostaining.

FIG. 3k shows that spontaneous cartilage destruction was determined by safranin-O staining in 12-month-old Col2a1-Zip8 TG mice and WT littermates. TG mice exhibited varying degrees of cartilage destruction from OARSI grade 1 to 6. None of the 12-month-old WT littermates (n=16) exhibited significant OA-associated phenotypes.

FIG. 3l represents spontaneous cartilage destruction in aged (12-month-old) WT and Zip8 TG mice (n=16).

FIGS. 3m and 3n represent subchondral bone sclerosis (FIG. 3m) and synovitis (FIG. 3n) in 12-month-old WT and Zip8 TG mice (n=16).

FIG. 3o shows cartilage destruction in 18- to 20-week-old DMM-operated WT and Zip8 TG mice (n=12)

FIG. 3p shows synovitis and subchondral bone sclerosis/osteophyte maturity in sham- and DMM-operated Col2a1-Zip8 TG mice and WT littermates (18- to 20-week-old) (n=12) were determined and quantified.

Scale bar: 50 μm. Values are presented as means±SEM (*P<0.05, P<0.01, *P<0.001).

FIGS. 4a to 4f represent that genetic deletion of Zip8 in mice inhibits OA pathogenesis.

Figure 4A:
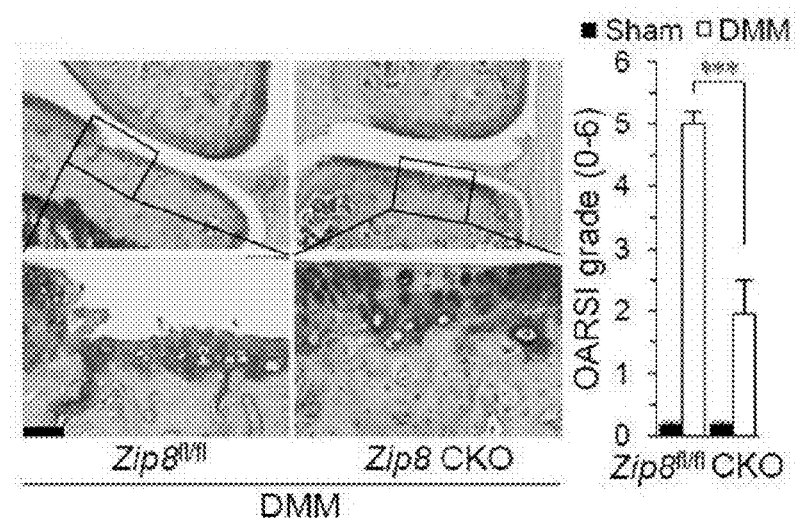

FIG. 4a represents that cartilage sections from sham- and DMM-operated $Zip8^{fl/fl}$ and chondrocyte-specific CKO mice were stained with safranin-O. Cartilage destruction was quantified by OARSI grade (n=10).

Figure 4B:
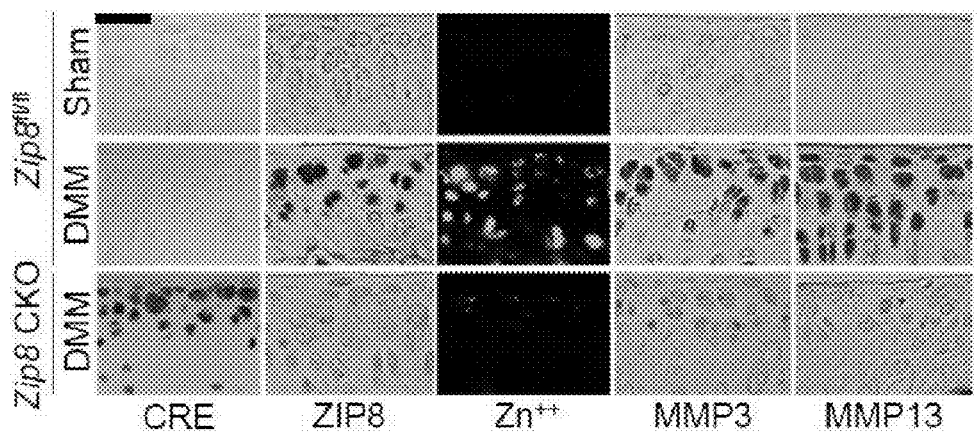

FIG. 4b shows that CRE, ZIP8, MMP3, and MMP13 were detected by immunostaining, and $Zn^{2+}$ was imaged in cartilage sections from $Zip8^{fl/fl}$ and Zip8-CKO mice after DMM surgery or sham operation.

Figure 4C:
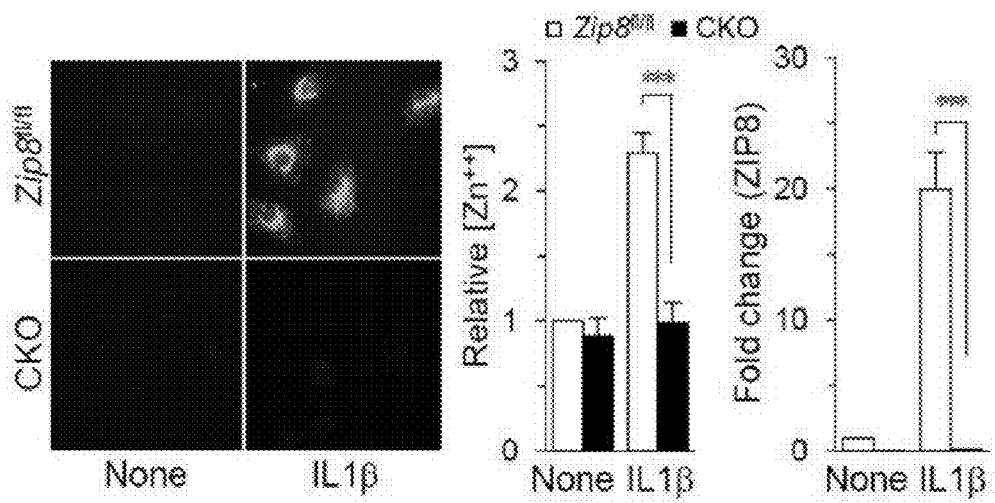
Figure 4D:
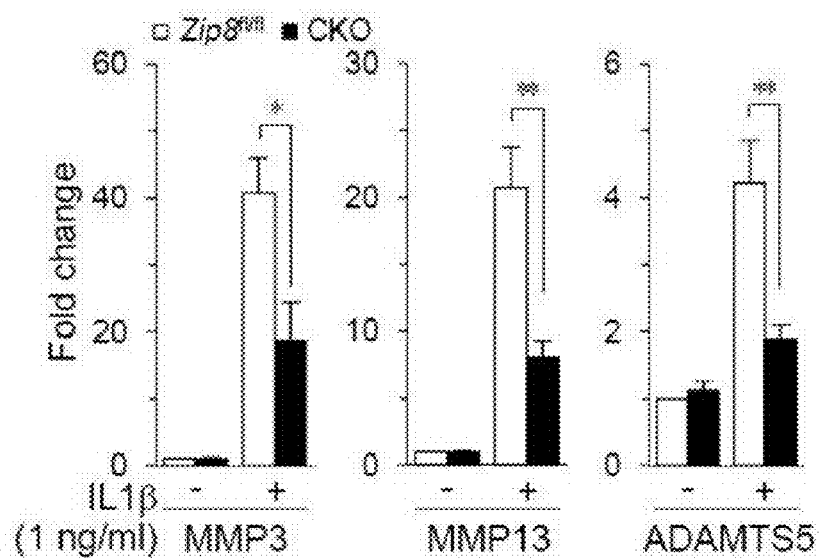

FIGS. 4c and 4d show that primary cultured chondrocytes isolated from $Zip8^{fl/fl}$ and Zip8-CKO mice were treated with IL1β. $Zn^{2+}$ was imaged and quantified using a fluorophore. mRNA levels of ZIP8 (FIG. 4c) and matrix-degrading enzymes (FIG. 4d) were determined by qRT-PCR (n≥4).

Figure 4E:
Figure 4F:
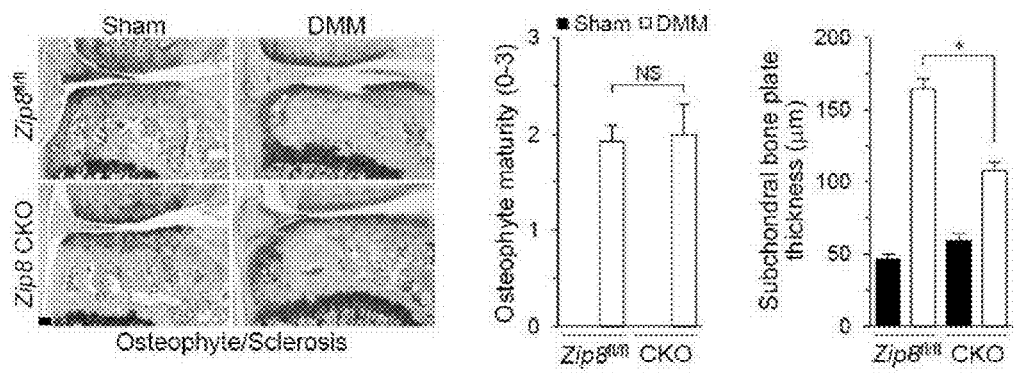

FIGS. 4e and 4f show synovitis (FIG. 4e) and subchondral bone sclerosis/osteophyte formation (FIG. 4f) in sham- and DMM-operated $Zip8^{fl/fl}$ and Zip8-CKO mice (n=10).

Scale bar: 50 μm. Values are presented as means±SEM (*P<0.01, P<0.005, *P<0.001)

Figure 5A:
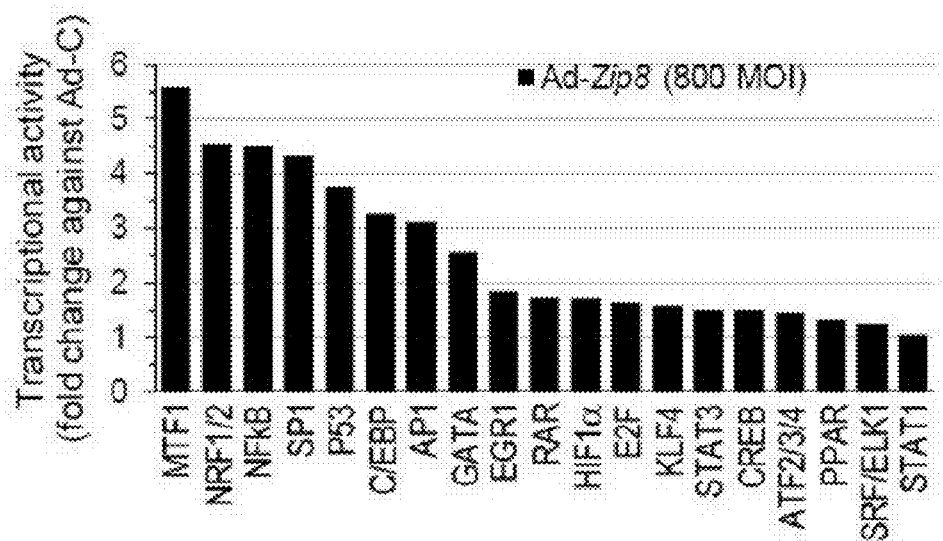
Figure 5B:
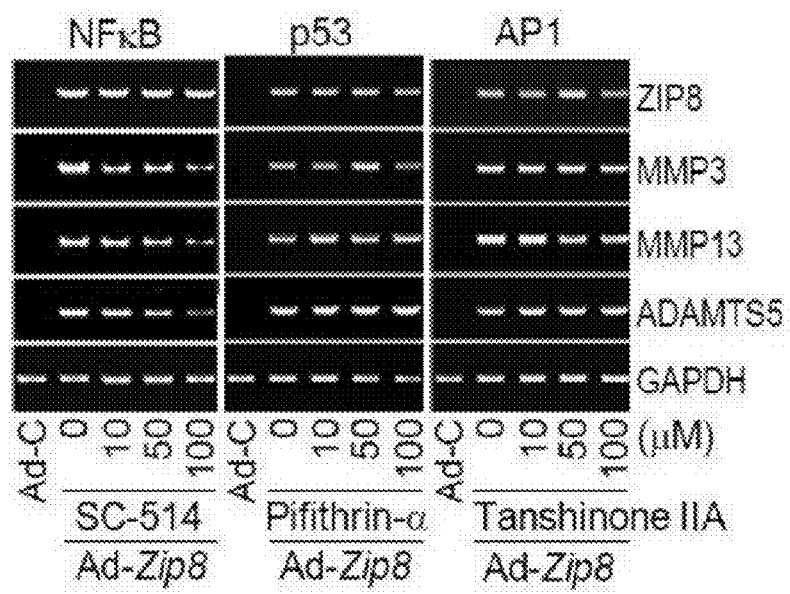
Figure 5C:
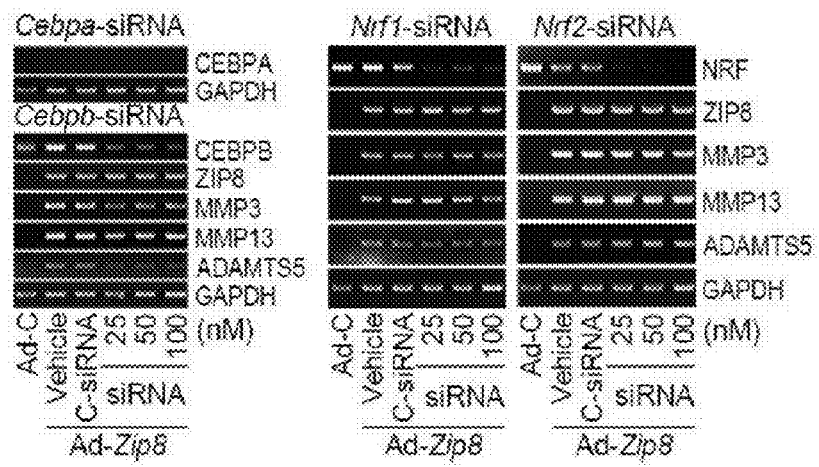
Figure 5D:
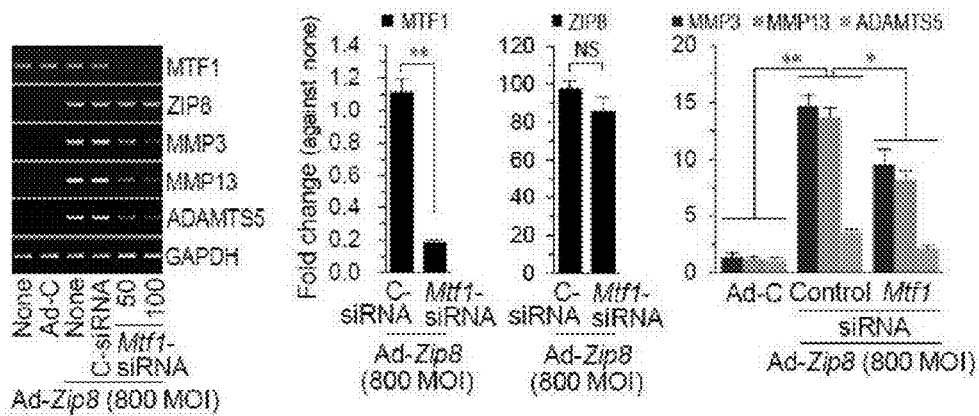
Figure 5E:
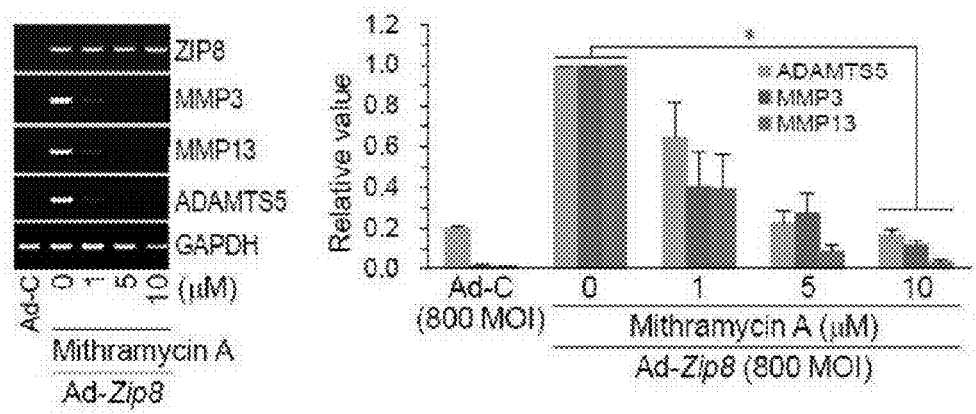
Figure 5F:
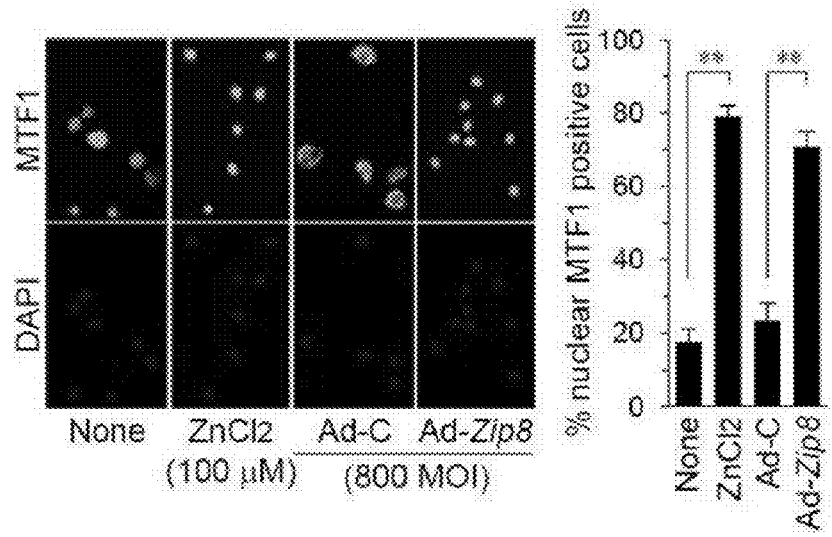
Figure 5G:
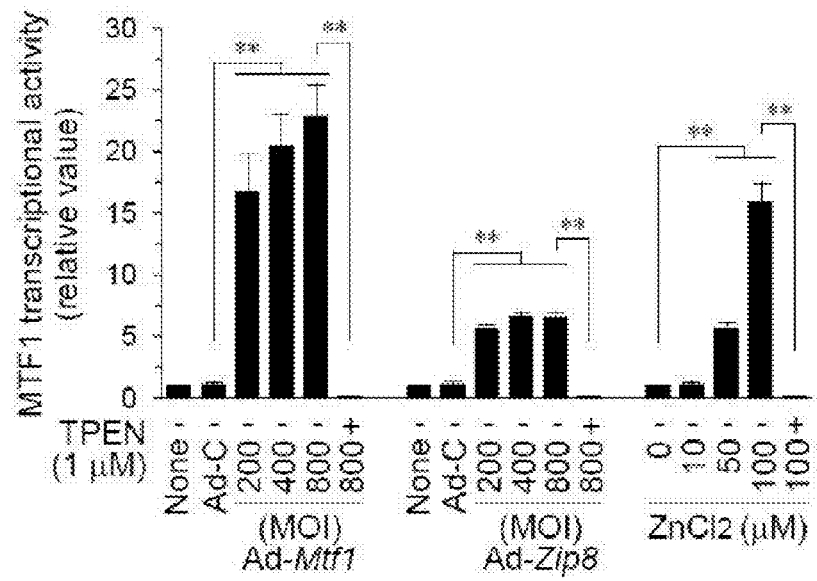
Figure 5H:
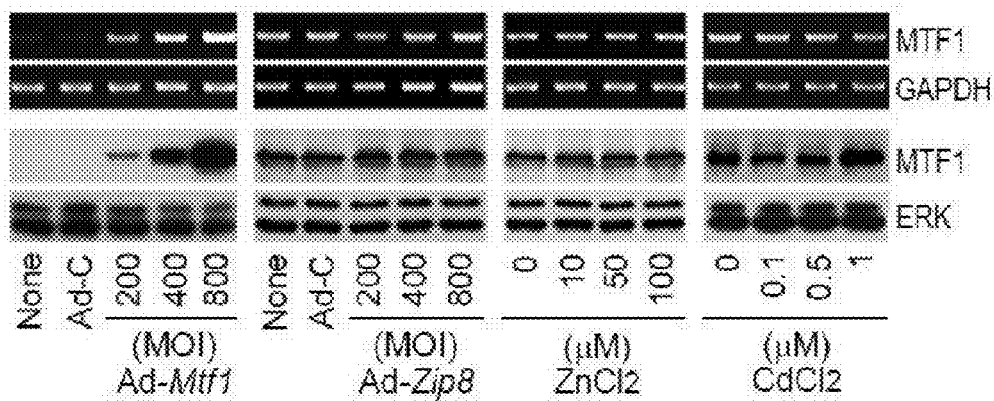
Figure 5I:
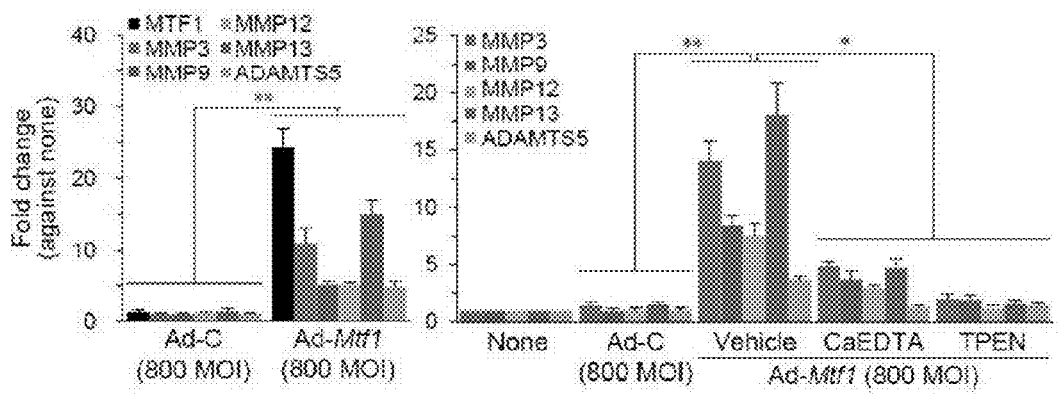
Figure 5J:
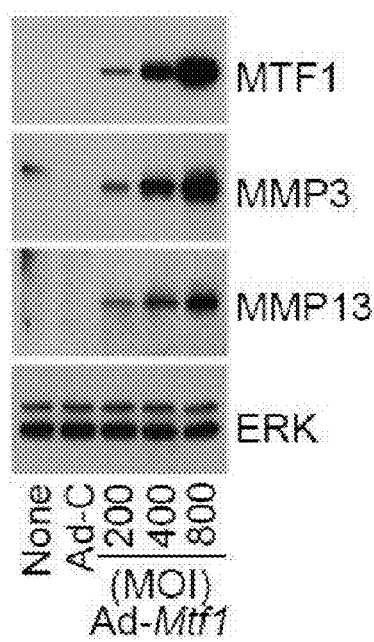
Figure 5K:
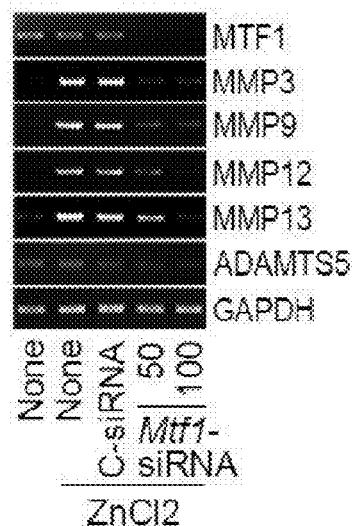
Figure 5L:
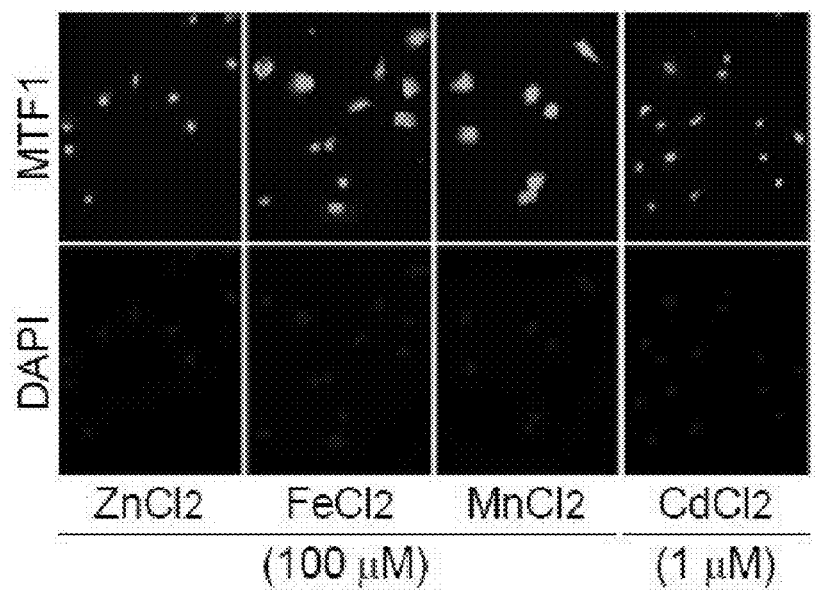
Figure 5M:
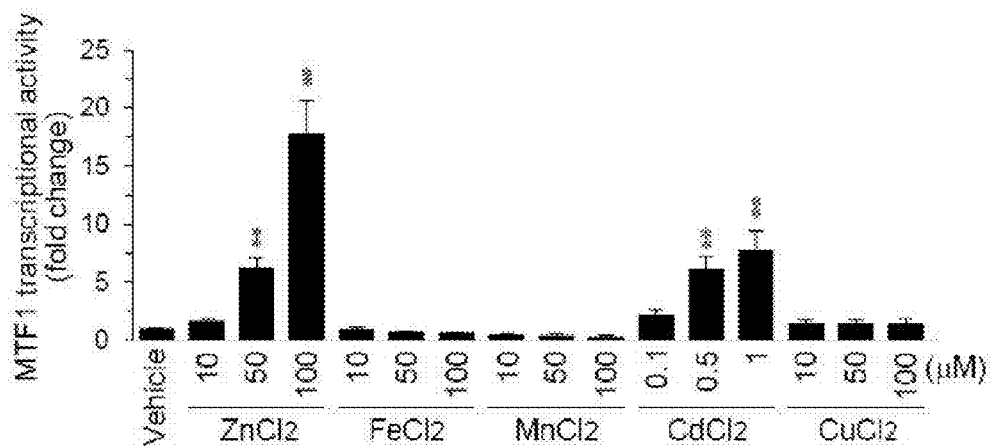
Figure 5N:
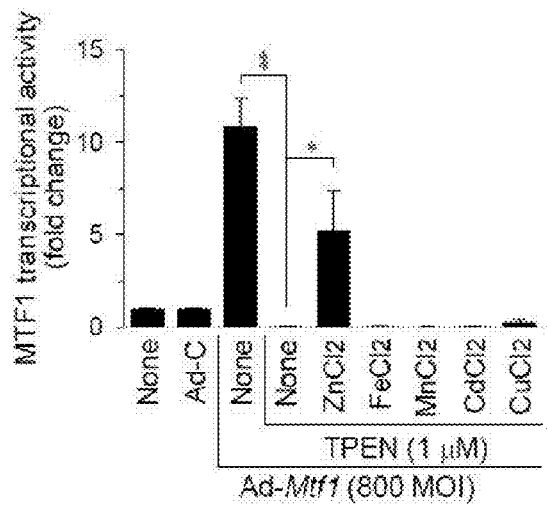

FIGS. 5a to 5n show that ZIP8-mediated $Zn^{2+}$ influx upregulates matrix-degrading enzymes through activation of MTF1.

FIG. 5a represents that primary cultured articular chondrocytes were infected with Ad-C or Ad-Zip8 at an MOI of 800 for 2 hours and incubated for an additional 24 hours. Transcriptional activities of the indicated transcription factors were determined using a transcription factor array kit (Cignal 45-Pathway Reporter Array).

FIG. 5b represents that chondrocytes were infected with Ad-C or Ad-Zip8 at an MOI of 800 for 2 hours and incubated for 24 hours in the absence or presence of the indicated concentrations of SC-514 to inhibit NFκB, pifithrin-α to inhibit p53, or tanshinone IIA to inhibit AP1.

FIG. 5c shows that chondrocytes, pretreated with 100 nM control siRNA (C-siRNA) or the indicated concentrations of siRNA targeting Nrf1, Nrf2, Cebpa or Cebpb, were infected with Ad-C or Ad-Zip8 at an MOI of 800 for 2 hours and incubated for 24 hours. The mRNA levels of indicated gene were detected by RT-PCR.

FIG. 5d shows mRNA levels determined in chondrocytes infected with Ad-C or Ad-Zip8 or treated with $ZnCl_2$ in the absence or presence of control- or Mtf1-siRNA.

FIG. 5e shows that chondrocytes were infected with Ad-C or Ad-Zip8 at an MOI of 800 for 2 hours and incubated for 24 hours in the absence or presence of the indicated concentrations of mithramycin A to inhibit SP1. The indicated mRNAs were detected by RT-PCR and quantified by qRT-PCR (n≥6).

FIG. 5f represents immunostaining for MTF1 and quantification of cells with nuclear-localized MTF1.

FIG. 5g represents MTF1 transcriptional activity quantified by reporter gene assay in chondrocytes treated with $ZnCl_2$, or infected with Ad-C, Ad-Zip8, or Ad-Mtf1 with or without TPEN (n=9).

FIG. 5h shows that chondrocytes were left untreated (None), or were infected with Ad-C at an MOI of 800 or with Ad-Mtf1 or Ad-Zip8 at the indicated MOI for 2 hours and incubated for additional 24 hours. Alternatively, chondrocytes were treated with the indicated concentrations of $ZnCl_2$ or $CdCl_2$ for 24 hours. MTF1 mRNA and protein levels were determined by RT-PCR and Western blotting, respectively.

FIG. 5i shows mRNA levels in chondrocytes infected with Ad-C or Ad-Mtf1(n≥5) in the absence or presence of CaEDTA or TPEN.

FIG. 5j represents protein levels of MTF1 and matrix-degrading enzymes.

FIG. 5k represents mRNA levels determined in chondrocytes infected with Ad-C or Ad-Zip8 or treated with $ZnCl_2$ in the absence or presence of control- or Mtf1-siRNA.

FIG. 5l represents that chondrocytes were treated with the indicated metal ions for 24 hours. Nuclear localization of MTF1 protein was detected by immunofluorescence microscopy.

FIG. 5m shows that chondrocytes were treated with the indicated concentrations of metal ions for 24 hours, and MTF1 transcriptional activity was determined (n=4).

FIG. 5n shows that chondrocytes infected with 800 MOI of Ad-C or Ad-Zip8 were left untreated or treated with TPEN (1 μM) or TPEN pre-incubated with the indicated metal ion (1 μM). MTF1 transcriptional activity was determined by reporter gene assay (n=4).

Values are presented as means±SEM (*P<0.01, **P<0.001).

Figure 6A:
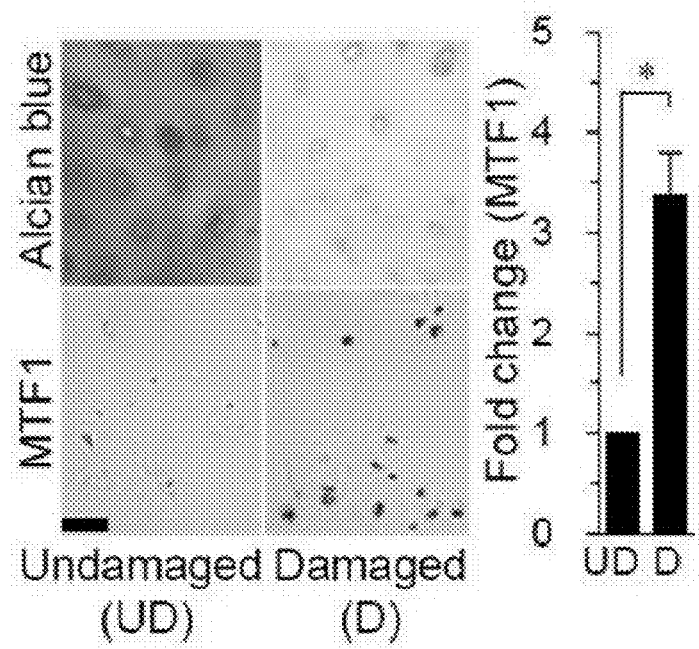
Figure 6B:
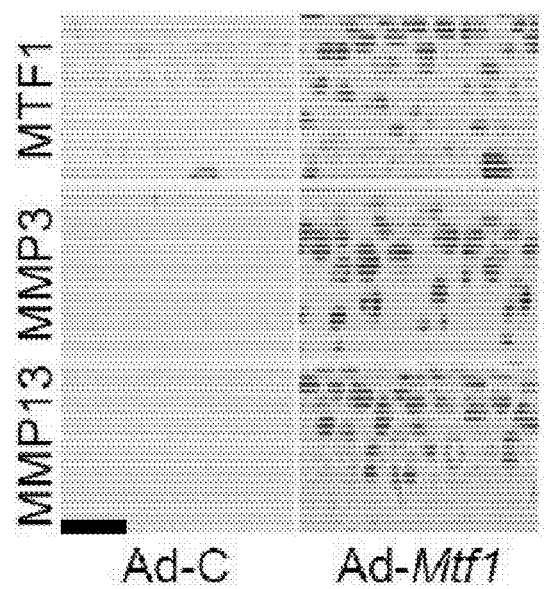
Figure 6C:
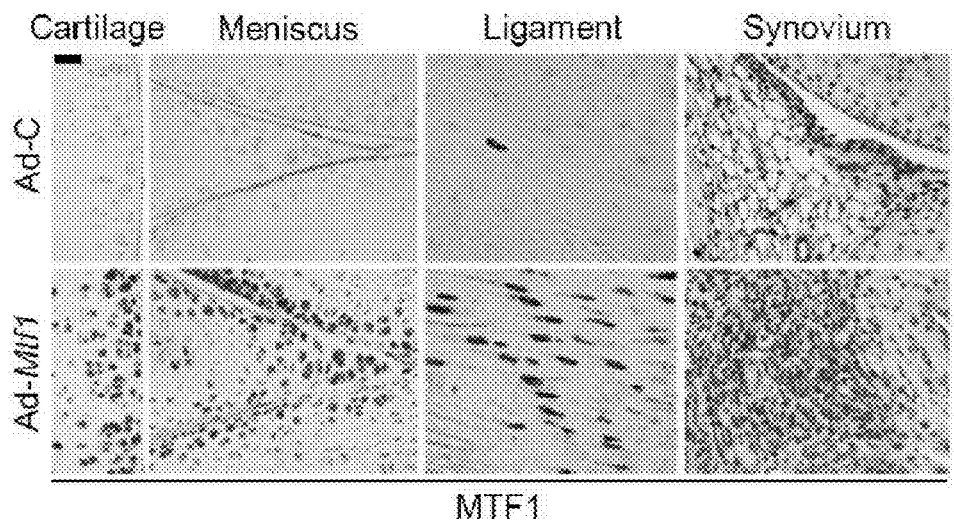
Figure 6D:
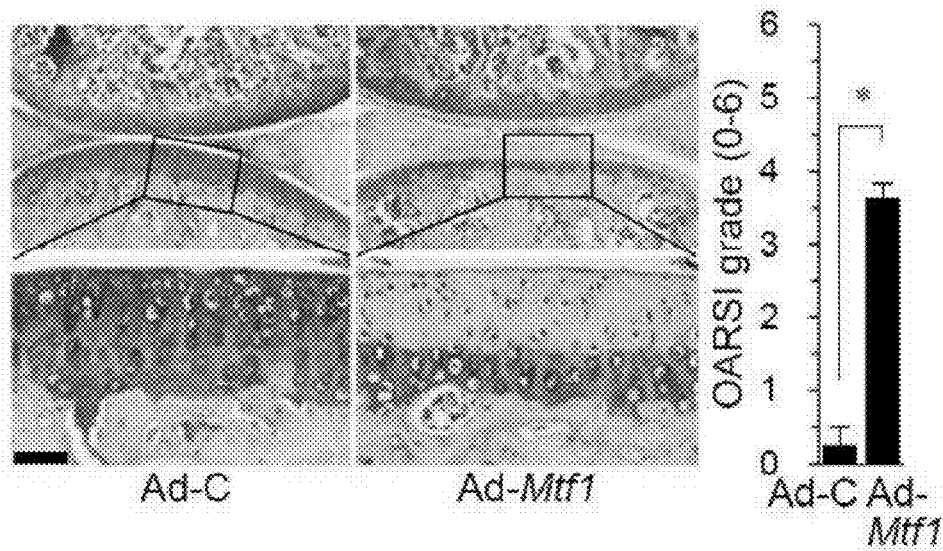
Figure 6E:
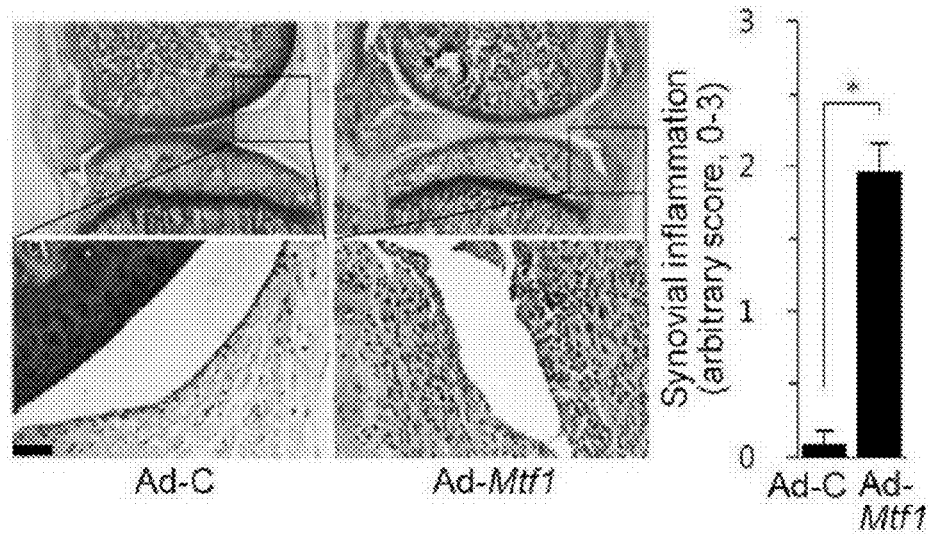
Figure 6F:
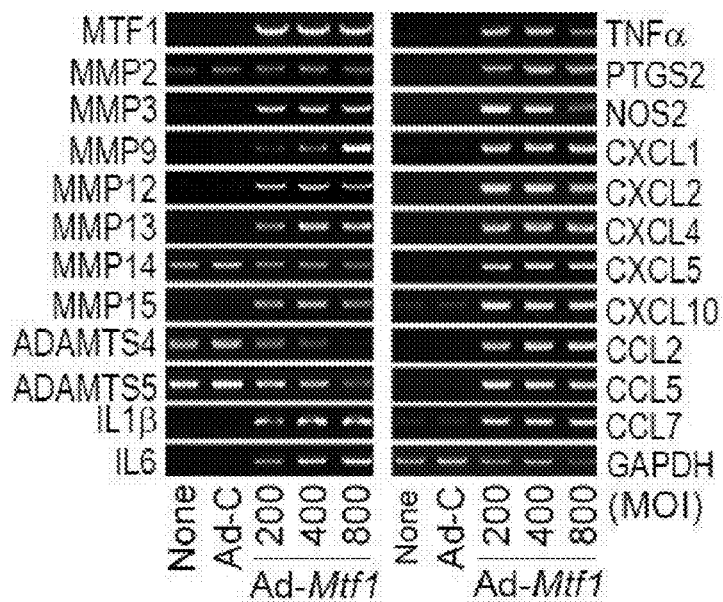
Figure 6G:
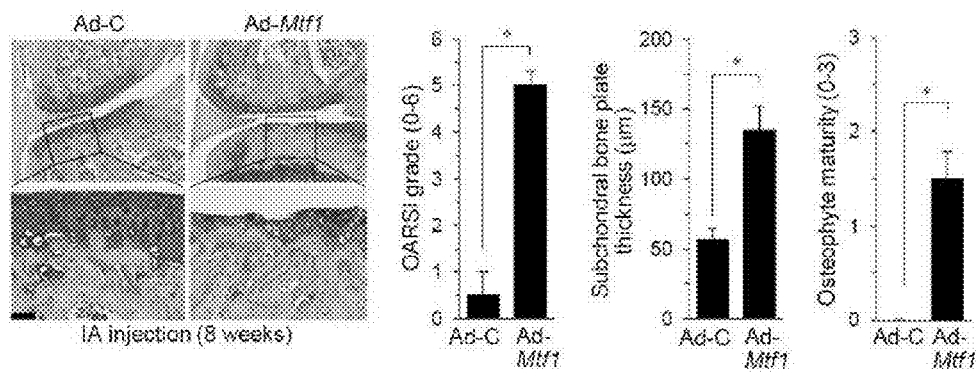
Figure 6H:
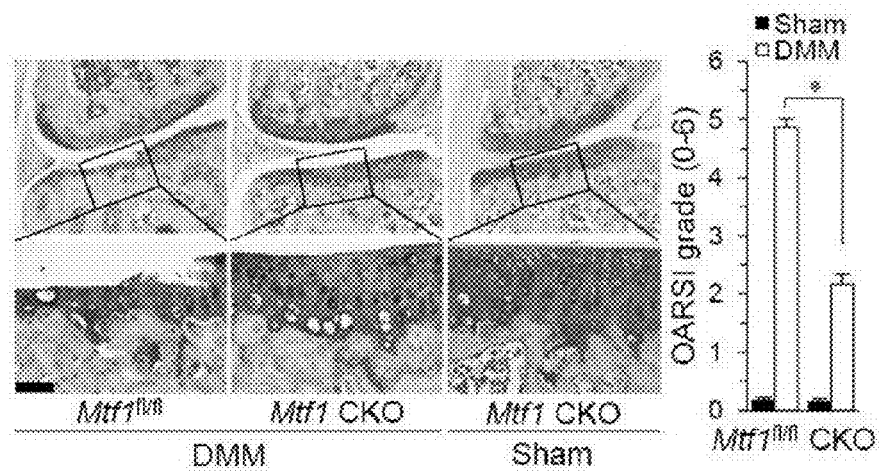
Figure 6I:
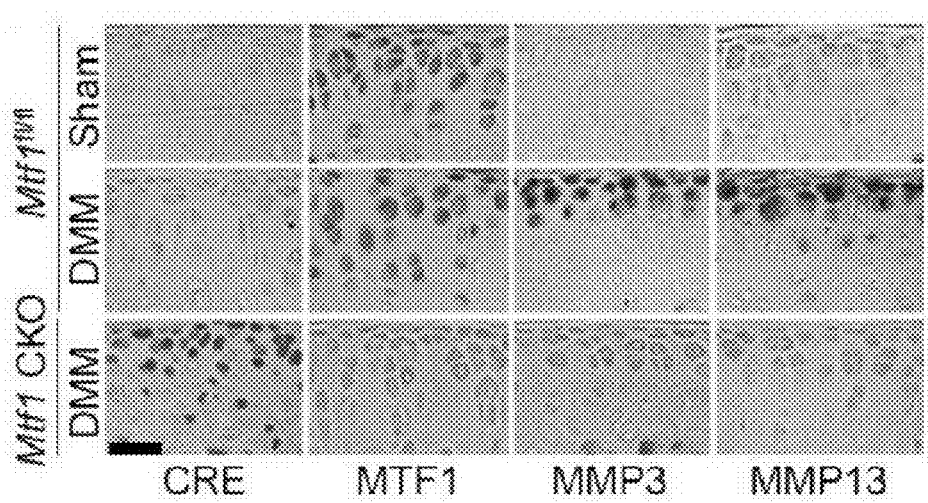
Figure 6J:
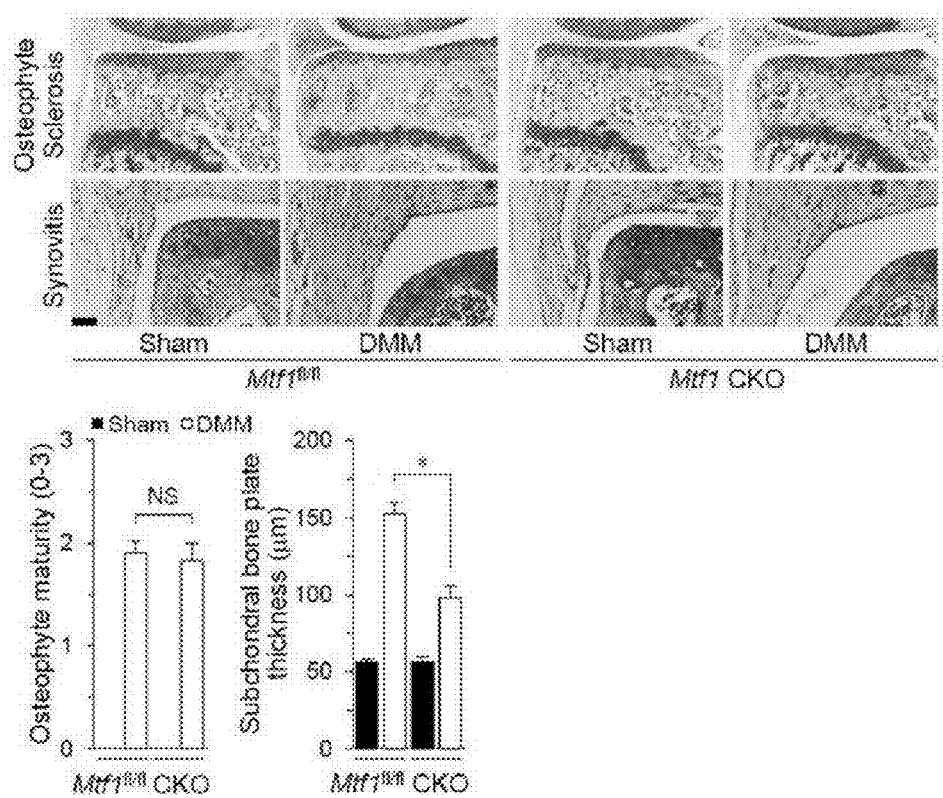
Figure 6K:
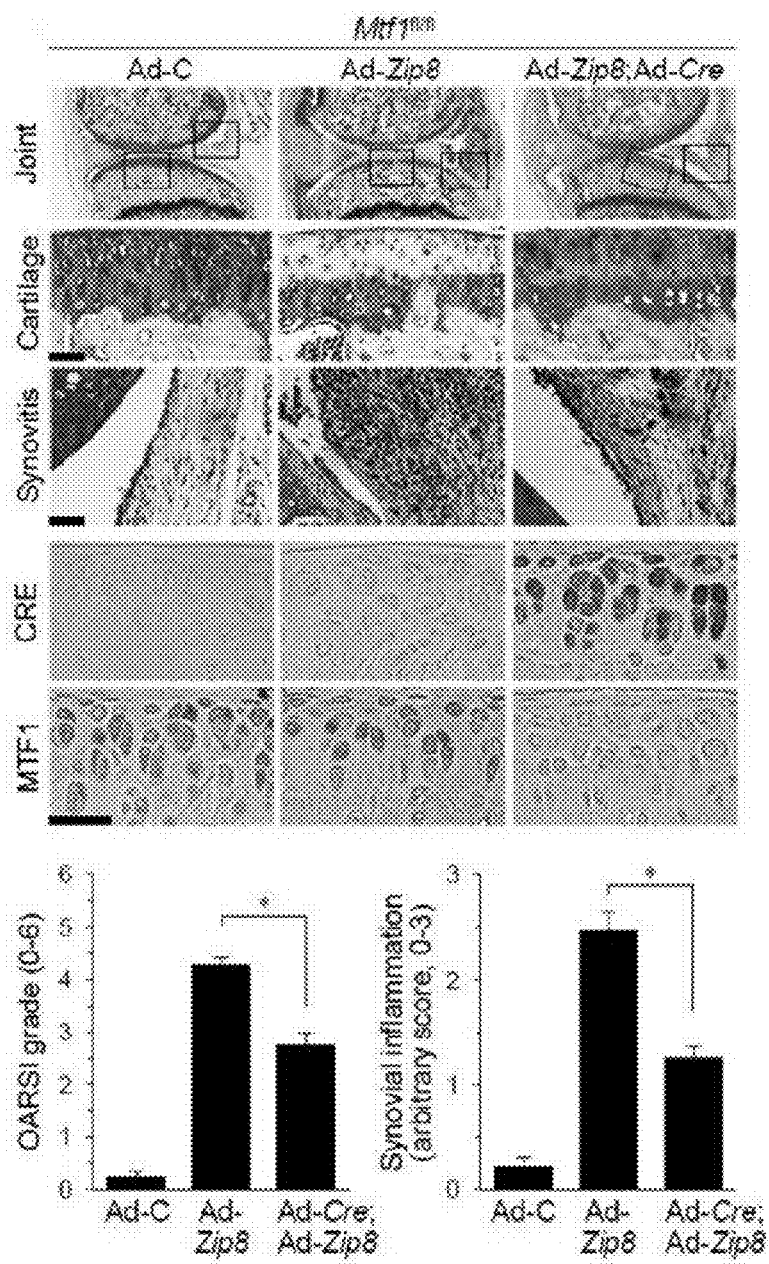
Figure 6L:
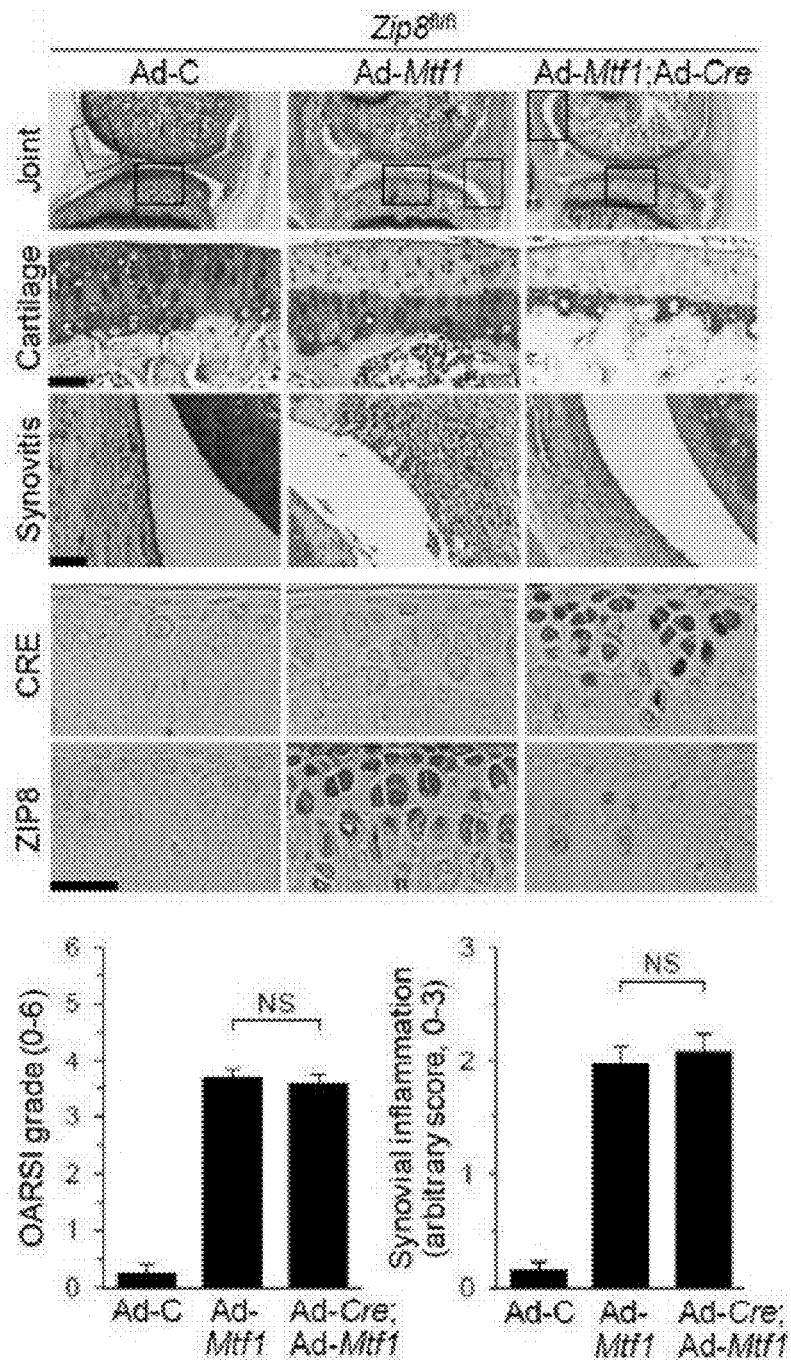
Figure 6M:
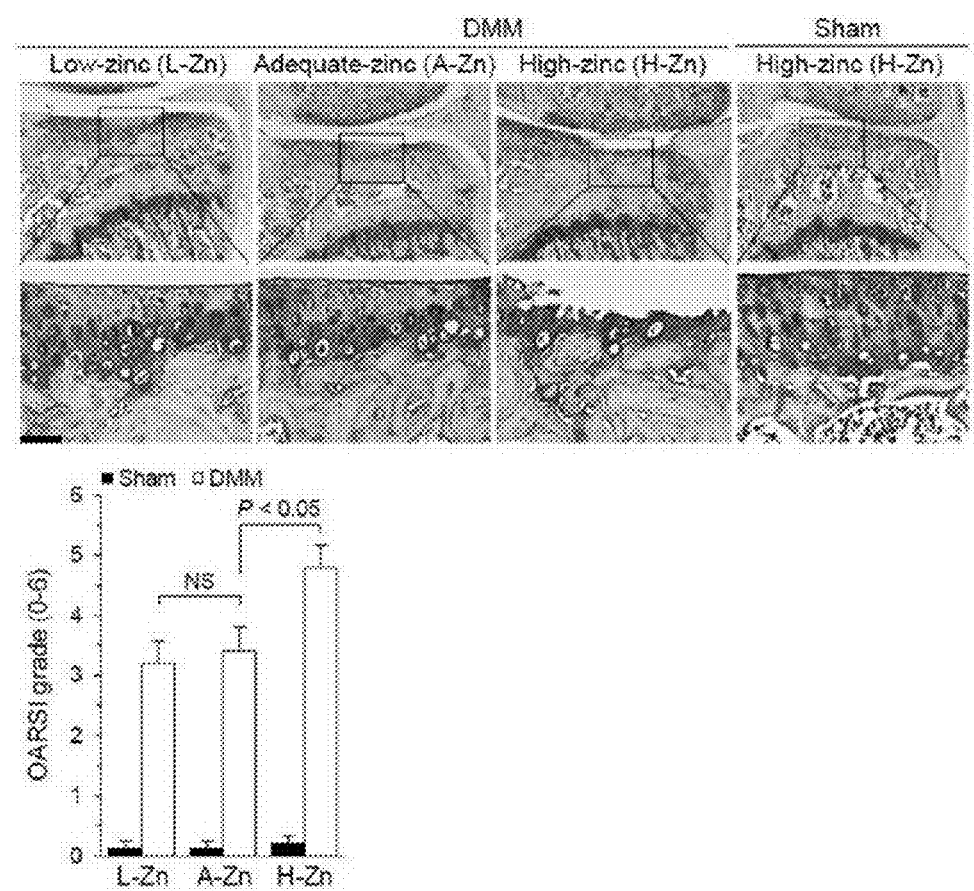
Figure 6N:
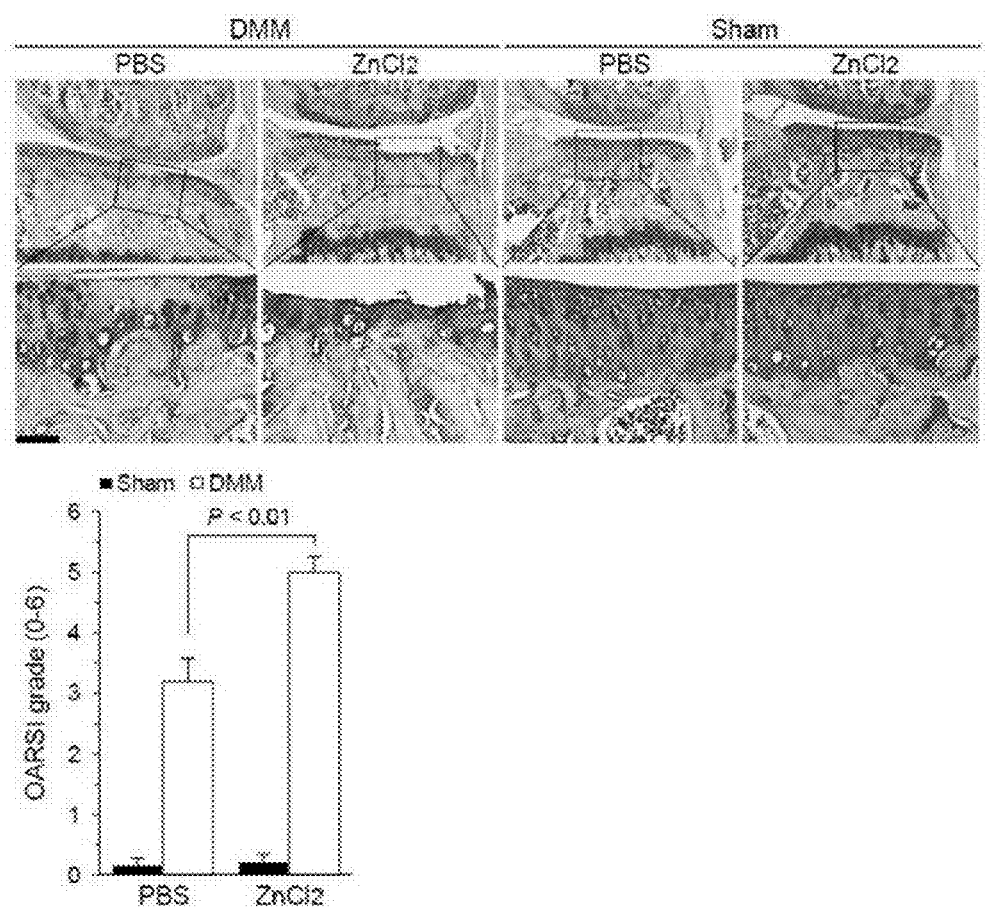

FIGS. 6a to 6n represent that MTF1 is a catabolic regulator of OA pathogenesis in mice.

FIG. 6a represents MTF1 protein and transcript levels in human OA cartilage determined by immunostaining and qRT-PCR, respectively (n=10).

FIGS. 6b and 6d represent that mice were IA-injected with Ad-C or Ad-Mtf1. MTF1, MMP3, and MMP13 immunostaining in cartilage sections (FIG. 6b). Safranin-O staining and scoring of cartilage destruction (n≥14) (FIG. 6d).

FIGS. 6c and 6e show that mice were IA-injected with Ad-C or Ad-Mtf1 ($1\times10^9$ PFU, once per week for 3 weeks) and sacrificed 21 days after the first injection. ZIP8 protein in meniscus, ligament, and synovium was determined by immunostaining and MTF1 protein in cartilage, meniscus, ligament, and synovium was determined by immunostaining (FIG. 6c). Representative images of synovitis in the knee joints of Ad-C- or Ad-Mtf1-injected mice (n≥14) (FIG. 6e).

FIG. 6f represents that primary cultures of mouse fibroblast-like synoviocytes were infected with Ad-C at an MOI of 800 or the indicated MOI of Ad-Mtf1 for 2 hours and incubated for 24 hours. The indicated mRNAs were detected by RT-PCR (n=4).

FIG. 6g represents that mice were IA-injected with Ad-C or Ad-Mtf1 ($1\times10^9$ PFU, once per week for 3 weeks) and sacrificed 8 weeks after the first injection. Cartilage destruction, subchondral bone sclerosis, and osteophyte formation were determined in knee joints by safranin-O/hematoxylin staining (n=10).

FIGS. 6h and 6i represent that cartilage sections from sham- and DMM-operated and Mtf1-CKO mice were stained with safranin-O and cartilage destruction was scored (n=10) (FIG. 6h) and immunostained for CRE, MTF1, MMP3, and MMP13 (FIG. 6i).

FIG. 6j represents that subchondral bone sclerosis/osteophyte formation and synovitis in sham- and DMM-operated Mtf1$^{fl/fl}$ and Mtf1-CKO (n=10).

FIG. 6k shows that Mtf1$^{fl/fl}$ mice were IA-injected with Ad-C or Ad-Cre ($1\times10^9$ PFU). After 1 week, Ad-C injected mice were IA-injected with Ad-C or Ad-Zip8($1\times10^9$ PFU, once per week for 3 weeks) and Ad-Cre-injected mice were co-injected with Ad-Zip8 ($1\times10^9$ PFU) or Ad-Cre ($1\times10^9$ PFU) once per week for three additional weeks. Mice were sacrificed 28 days after the first injection. Cartilage destruction and synovitis were determined by safranin-O/hematoxylin staining and quantified (n=10). CRE and MTF1 proteins were detected by immunostaining.

FIG. 6l shows that Zip8$^{fl/fl}$ mice were IA-injected with Ad-C or Ad-Cre. Ad-C-injected mice underwent three additional IA injections with Ad-C or Ad-Mtf1 ($1\times10^9$ PFU, once a week). Ad-Cre-injected mice were co-injected with Ad-Mtf1 ($1\times10^9$ PFU) or Ad-Cre ($1\times10^9$ PFU) for three additional weeks. Mice were sacrificed 28 days after the first injection. Cartilage destruction and synovitis were determined by safranin-O/hematoxylin staining and quantified (n=10). CRE and ZIP8 proteins were detected by immunostaining.

FIG. 6m represents that knee joint sections were prepared from sham- and DMM-operated mice that were fed low-$Zn^{2+}$ (<0.5 mg zinc/kg), adequate-$Zn^{2+}$ (30 mg zinc/kg), or high-$Zn^{2+}$ (300 mg zinc/kg) diets. Cartilage destruction was determined by safranin-O/hematoxylin staining and quantified (n=10).

FIG. 6n represents that sham- and DMM-operated mice were intraperitoneally injected with PBS or ZnCl2 (5 mg/kg body weight) twice a week until they are sacrificed 6 weeks after surgery. Knee joint sections were stained with safranin-O/hematoxylin and cartilage destruction was determined (n=10).

Scale bar: 50 μm. Values are presented as means±SEM (*P<0.001).

FIGS. 7a to 7e represent that double knockout of Mt1 and Mt2 enhances OA pathogenesis in mice.

Figure 7A:
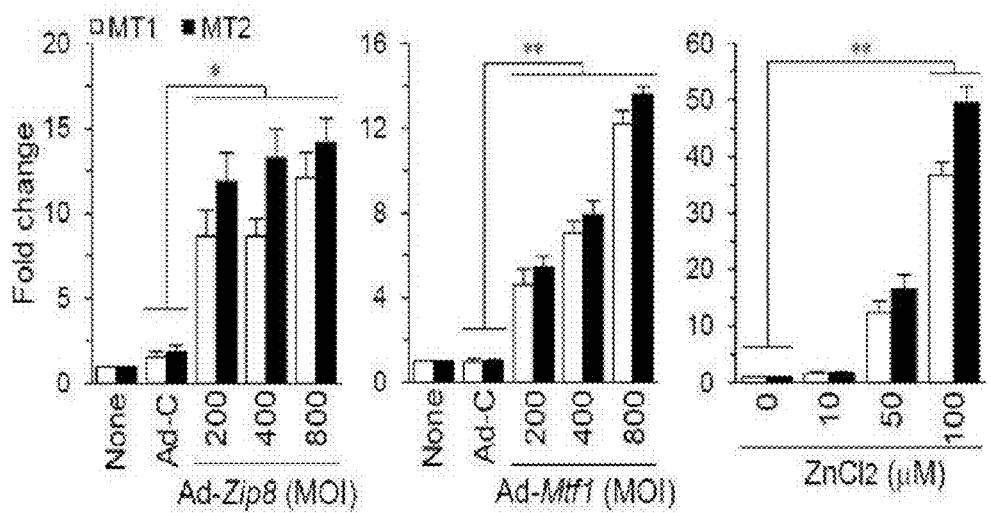

FIG. 7a shows mRNA levels of MT1 and MT2 in chondrocytes infected with Ad-Zip8 or Ad-Mtf1 or treated with ZnCl2 (n≥6).

Figure 7B:
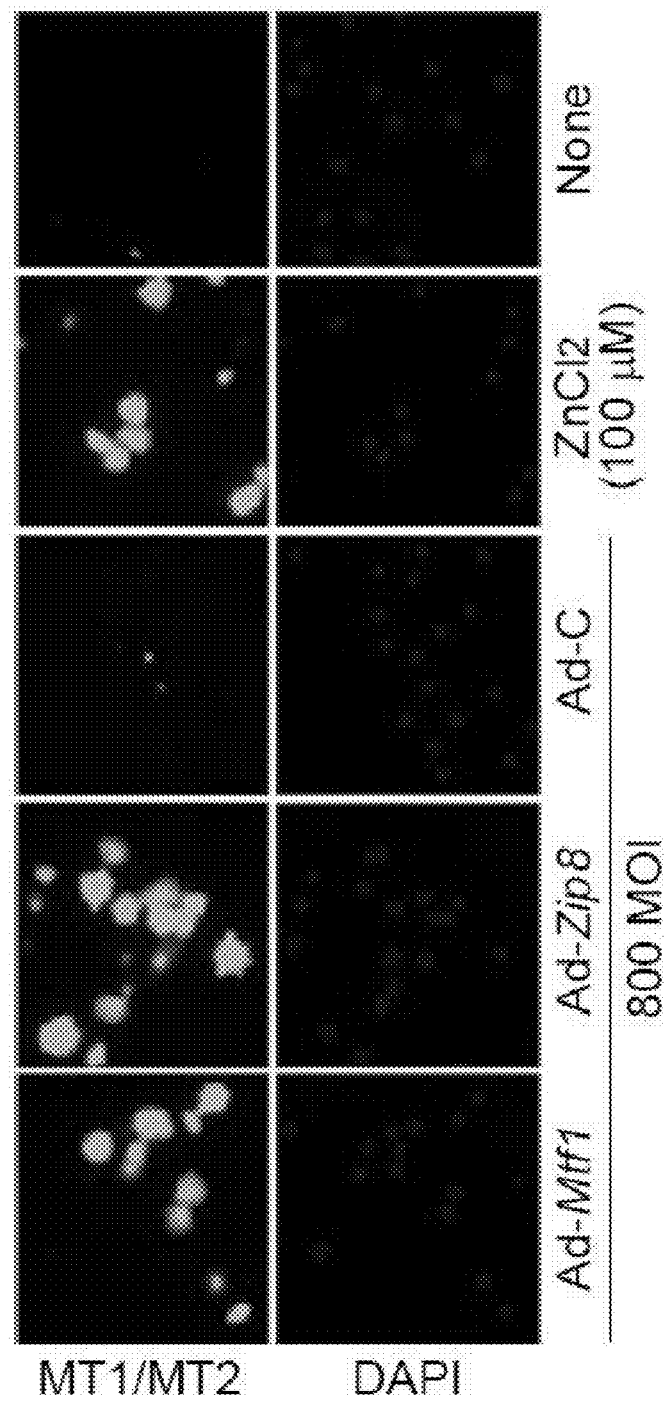

FIG. 7b shows detection of MT1/MT2 proteins in chondrocytes treated with $ZnCl_2$ or infected with Ad-Zip8, Ad-Mtf1, or Ad-Mt2.

Figure 7C:
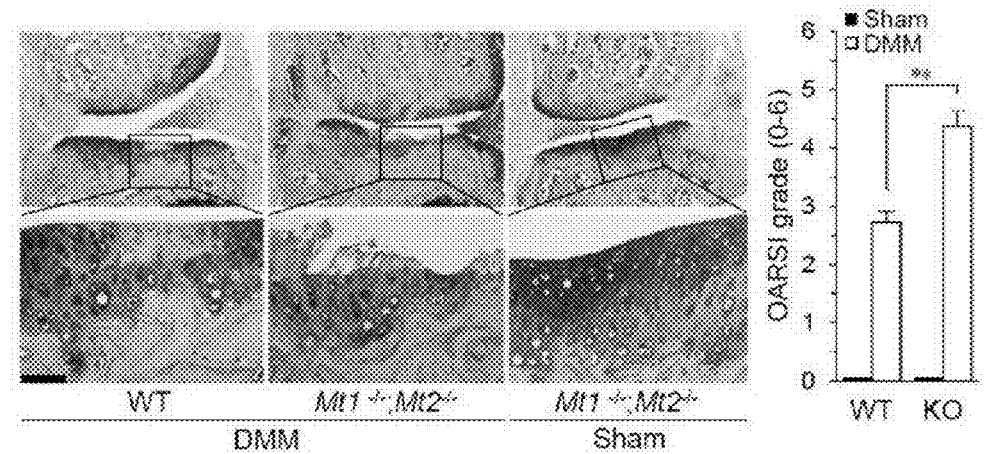
Figure 7D:
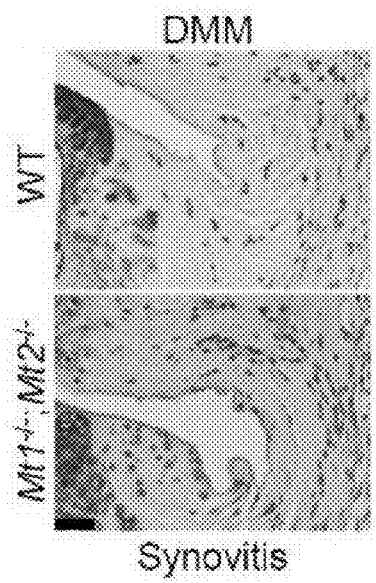
Figure 7E:
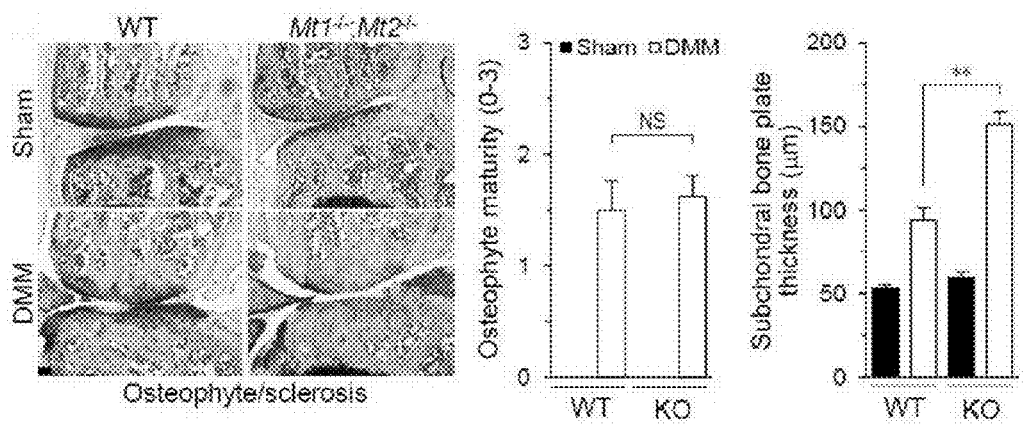

FIGS. 7c-7e represent cartilage destruction (FIG. 7c), synovitis (FIG. 7d), osteophyte formation, and subchondral bone sclerosis (FIG. 7e) in sham- and DMM-operated WT and Mt1$^{-/-}$; Mt2$^{-/-}$ double-KO mice (n=13).

Scale bar: 50 μm. Values are presented as means±SEM (*P<0.005, **P<0.001).

BEST MODE FOR CARRYING OUT THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLE

Experimental Procedures

Human OA Cartilage Tissue

International Cartilage Repair Society (ICRS) grade 4 human OA cartilage was sourced from individuals (age, 51 to 72 years) undergoing arthroplasty. The Institutional Review Board of the Wonkwang University Hospital approved the use of these materials, and all individuals provided full written informed consent before the operative procedure.

Mice and Experimental OA

Male mice (C57BL/6, Col2a1-Zip8 TG, Zip8$^{+/-}$, Zip8$^{fl/fl}$; Zip8$^{fl/fl}$; Col2a1-Cre, Mtf1$^{+/-}$, Mtf1$^{fl/fl}$, Mtf1$^{fl/fl}$; Col2a1-Cre, Mt1$^{-/-}$; Mt2$^{-/-}$) were used for experimental OA studies. Chondrocyte-specific Zip8 TG (Col2a1-Zip8) mice were generated using the Col2a1 promoter and enhancer. Zip8$^{+/-}$ mice were obtained from The European Mouse Mutant Archive. The Mtf1 mouse strain used for this research project was created from an ES cell clone generated by the Wellcome Trust Sanger Institute and developed into mice by the KOMP Repository and the Mouse Biology Program at the University of California, Davis. Zip8$^{+/-}$ and Mtf1$^{+/-}$ mice were backcrossed with Actb-Flp1 TG mice (The Jackson Laboratory) to generate Zip8fl/fl and Mtf1fl/fl mice, respectively. These mice were then backcrossed with Col2a1-Cre TG mice (The Jackson Laboratory) to generate chondrocyte-specific CKO mice (Zip8$^{fl/fl}$; Col2a1-Cre and Mtf1$^{fl/fl}$; Col2a1-Cre). Mt1$^{-/-}$, Mt2$^{-/-}$ double-KO mice were obtained from The Jackson Laboratory. The inbred strain 129S1/SvImJ was used as a control for Mt1$^{-/-}$; Mt2$^{-/-}$ double-KO mice. All mice used in this study showed normal skeletal development (data not shown). Animals were maintained under pathogen-free conditions. All experiments were approved by the Gwangju Institute of Science and Technology Animal Care and Use Committee. Experimental OA was induced by DMM surgery using 10- to 12-week-old male mice; sham-operated mice were used as controls (Glasson et al., 2007). Knee joints were processed for histological analysis 8 weeks after surgery. However, in studies involving Col2a1-Zip8 TG mice and Mt1$^{-/-}$; Mt2$^{-/-}$ double-KO mice, the duration after surgery was adjusted to 6 weeks. Experimental OA was also induced by IA injection (once weekly for 3 weeks) of Ad-Zip8 or Ad-Mtf1 (1×10$^9$ plaque forming units [PFUs] in a total volume of 10 μl) into 10- to 12-week-old male mice; IA injection of empty adenovirus (Ad-C) was used as a control. Mice were sacrificed 3 or 8 weeks after the first IA injection for histological and biochemical analyses. Where indicated, the mice were co-injected (IA) with 0.1 mg/kg body weight of TPEN.

Histology and Immunohistochemistry

Human OA cartilage was frozen, sectioned at 10-μm thickness, and fixed in paraformaldehyde. Sulfate proteoglycan was detected with alcian blue staining. Human ZIP8 was detected by immunostaining. Cartilage destruction in mice was examined using safranin-O staining. Briefly, knee joints were fixed in 4% paraformaldehyde, decalcified in 0.5 M EDTA, and embedded in paraffin. The paraffin blocks were sectioned at a thickness of 5 μm. Serial sections were obtained from the entire joint at 40-μm intervals. Sections were deparaffinized in xylene, hydrated with graded ethanol, and stained with safranin-O. Cartilage destruction was scored by two blinded observers using the OARSI grading system (Glasson et al., 2010). Synovitis was determined by safranin-O and hematoxylin staining, and synovial inflammation (grade 0-3) was scored as described previously (Yang et al., 2010). Osteophyte development was identified by safranin-O staining, and osteophyte maturity was quantified as described previously (Oh et al., 2012). Subchondral bone sclerosis was determined by measuring the thickness of the subchondral bone plate (Zhen et al., 2013). Antibodies used for immunostaining of cartilage sections are as follows: ZIP8 and MTF1 in human cartilage tissue sections were detected by antibodies obtained from Proteintech (20459-1-AP) and Novus (NBP1-86380), respectively. The following antibodies were used for immunostaining of mouse joint tissue sections: anti-CRE from Covance (MMS-106P), anti-MMP3 from Epitomics (1908-1), anti-MMP13 from Epitomics (1923-1), anti-MTF1 from Novus (NBP1-86380), anti-MT1/MT2 from Novus (NBP1-97493), and anti-ZIP8 from Santa Cruz Biotechnology (SC-133415). For Western blotting, antibodies were purchased from Thermo Scientific for ADAMTS5 (PA5-14350), BD Biosciences for ERK1 (610408), Epitomics for MMP3 (1908-1) and MMP13 (1923-1), Novus for MTF1 (NBP1-86380), and Santa Cruz Biotechnology for ZIP8 (SC-133415).

Primary Culture of Articular Chondrocytes

Chondrocytes were isolated from femoral condyles and tibial plateaus of mice, as described previously (Yang et al., 2010, Ryu et al., 2012, Oh et al., 2012). Chondrocytes were maintained as a monolayer in Dulbecco's Modified Eagle's Medium (DMEM) supplemented with 10% fetal bovine serum (FBS) and antibiotics, and cells at culture day 2 were treated as indicated in each experiment.

Adenoviruses, Infection of Chondrocytes and IA Injection

Adenoviruses expressing mouse Zip8 (Ad-Zip8) and Mtf1 (Ad-Mtf1) were purchased from Vector Biolabs. Mouse articular chondrocytes were cultured for 2 days, infected with empty virus (Ad-C), Ad-Zip8, or Ad-Mtf1 for 2 hours at the indicated multiplicity of infection (MOI), and cultured for 24 hours, followed by further analyses.

$Zn^{2+}$ Imaging and Quantitation

Intracellular $Zn^{2+}$ was detected using the $Zn^{2+}$-selective fluorophore, FluoZin-3 AM (Invitrogen). Primary cultured articular chondrocytes and frozen sections of cartilage tissue were treated with 1 and 5 μM FluoZin-3 AM, respectively, in the presence of 0.02% and 0.1% Pluronic F-127(Invitrogen) for 30 minutes at 37° C. Cells were then washed with $Ca^{2+}$- and $Mg^{2+}$-free phosphate-buffered saline (PBS) and incubated for an additional 30 minutes at 37° C. Intracellular $Zn^{2+}$ images were acquired with a fluorescence microscope, and population-wide fluorescence intensity was measured using a Spectramax Gemini microplate fluorescence reader (Molecular Devices) with excitation at 488 nm, cut-off at 515 nm, and emission at 530 nm.

MTF1 Activity Reporter Gene Assay and Immunostaining

The MTF1 reporter gene assay kit was obtained from SABiosciences. Chondrocytes were transfected for 6 hours with a metal response element (MRE) reporter construct and a constitutive Renilla luciferase construct using Lipofectamine 2000 (Invitrogen). Transfected cells were infected with Ad-Mtf1 or Ad-Zip8 for 2 hours or treated with metal ions. Cells were harvested 24 hours after treatment, and firefly luciferase and Renilla luciferase activities were measured using a Dual Luciferase Assay System (Promega). For immunostaining, cells were fixed in ice-cold 4% paraformaldehyde (pH 7.4), permeabilized with 0.2% Triton X-100 in PBS, and serially blocked with Image-iT FX Signal Enhancer (Invitrogen) and PBS containing 10% goat serum/ 0.1% bovine serum albumen. MTF1 was detected by immunofluorescence microscopy. Images were acquired using a fluorescence microscope, and at least 200 cells were examined in multiple fields per condition to quantify the percentage of nuclear MTF1-positive cells.

Reverse Transcription-Polymerase Chain Reaction (RT-PCR), Quantitative RT-PCR(qRT-PCR), siRNA and Therapeutic Antibodies Against ZIP8

Total RNA was extracted from primary cultured chondrocytes using the TRI reagent (Molecular Research Center Inc.). For the isolation of RNA from knee joints, cartilage tissues were scraped with a blade to remove cartilage, and RNA was isolated using the TRI reagent and Purelink RNA mini kit (Ambion). The RNA was reverse transcribed, and the resulting cDNA was amplified by PCR. PCR primers and experimental conditions are summarized in Table 1.

TABLE 1

PCR primers and conditions

| Gene | Strand | Primer sequences | Size (bp) | AT (° C.) | Origin |
| --- | --- | --- | --- | --- | --- |
| Adamts4 | S | 5-CATCCGAAACCCTGTCAACTTG-3 | 281 | 58 | Mouse |
|  | AS | 5-GCCCATCATCTTCCACAATAGC-3 |  |  |  |

TABLE 1-continued

PCR primers and conditions

| Gene | Strand | Primer sequences | Size (bp) | AT (° C.) | Origin |
|---|---|---|---|---|---|
| Adamts5 | S | 5-GCCATTGTAATAACCCTGCACC-3 | 292 | 58 | Mouse |
|  | AS | 5-TCAGTCCCATCCGTAACCTTTG-3 |  |  |  |
| Cre | S | 5-CAATGCTGTTTCACTGGTTATGCG-3 | 364 | 58 | Enterobacetria Phage P1 |
|  | AS | 5-AGCTACACCAGAGACGGAAATCCATC-3 |  |  |  |
| GAPDH | S | 5-CGTCTTCACCACCATGGAGA-3 | 300 | 62 | Human |
|  | AS | 5-CGGCCATCACGCCACAGTTT-3 |  |  |  |
| Gapdh | S | 5-TCACTGCCACCCAGAAGAC-3 | 450 | 58 | Mouse |
|  | AS | 5-TGTAGGCCATGAGGTCCAC-3 |  |  |  |
| Mmp2 | S | 5-CCAACTACGATGATGAC-3 | 233 | 60 | Mouse |
|  | AS | 5-ACCAGTGTCAGTATCAG-3 |  |  |  |
| Mmp3 | S | 5-TCCTGATGTTGGTGGCTTCAG-3 | 102 | 58 | Mouse |
|  | AS | 5-TGTCTTGGCAAATCCGGTGTA-3 |  |  |  |
| Mmp9 | S | 5-ACCACATCGAACTTCGA-3 | 212 | 58 | Mouse |
|  | AS | 5-CGACCATACAGATACTG-3 |  |  |  |
| Mmp12 | S | 5-CCCAGAGGTCAAGATGGATG-3 | 482 | 60 | Mouse |
|  | AS | 5-GGCTCCATAGAGGGACTGAA-3 |  |  |  |
| Mmp13 | S | 5-TGATGGACCTTCTGGTCTTCTGG-3 | 473 | 58 | Mouse |
|  | AS | 5-CATCCACATGGTTGGGAAGTTCT-3 |  |  |  |
| Mmp14 | S | 5-GTGCCCTAGGCCTACATCCG-3 | 580 | 62 | Mouse |
|  | AS | 5-TTGGGTATCCATCCATCACT-3 |  |  |  |
| Mmp15 | S | 5-GAGAGATGTTTGTGTTCAAGGG-3 | 260 | 62 | Mouse |
|  | AS | 5-TGTGTCAATGCGGTCATAGGG-3 |  |  |  |
| Mt1 | S | 5-CAACTGCTCCTGCTCCACCG-3 | 132 | 58 | Mouse |
|  | AS | 5-CCCTGGGCACATTTGGAGCAG-3 |  |  |  |
| Mt2 | S | 5-AGCCCTGGGAGCACTTCGCAC-3 | 138 | 58 | Mouse |
|  | AS | 5-ACCCCAACTGCTCCTGTGCCTC-3 |  |  |  |
| MTF1 | S | 5-TCTGGAACTGTTTATGATAGG-3 | 446 | 58 | Human |
|  | AS | 5-CTGAGGCTGTAAGAGGTAAGG-3 |  |  |  |
| Mtf1 | S | 5-GTTTTAATGGTGATGCAGAGTCCGTC-3 | 461 | 62 | Mouse |
|  | AS | 5-GGGATTATTAGTTAGGACAGAGTTGGC-3 |  |  |  |
| Mtf1 | S | 5-CCAGTGCACCTTTGAGGGATG-3 | 189 | 62 | Mouse (KO) |
|  | AS | 5-TCACACTCAAATGGCTTCTCCTT-3 |  |  |  |
| Zip1 | S | 5-AGTAGGGCTGGAAGTGAAGC-3 | 484 | 62 | Mouse |
|  | AS | 5-GAAGACCAGGACACAAGCAC-3 |  |  |  |
| Zip2 | S | 5-ATGACTGCTGAAGCTCTGGA-3 | 436 | 58 | Mouse |
|  | AS | 5-TGAACACCACAAGCCCCTTA-3 |  |  |  |
| Zip3 | S | 5-TGGTGGGTTTCTTCCTCACT-3 | 566 | 62 | Mouse |
|  | AS | 5-GGTGACAAACAGGAAGGTGC-3 |  |  |  |
| Zip4 | S | 5-AAGATGGGCCTTGTAGCCAT-3 | 427 | 64 | Mouse |
|  | AS | 5-ACTGCTAGAGCCACGTAGAG-3 |  |  |  |
| Zip5 | S | 5-ATTGACAGCCGTGTTTGCAT-3 | 523 | 58 | Mouse |
|  | AS | 5-GAGGGGCTAGAGATGGTGAG-3 |  |  |  |
| Zip6 | S | 5-GTCACACGGTTGCTGGTAAA-3 | 361 | 62 | Mouse |
|  | AS | 5-AAGCTCTTTCTGGGCTCACT-3 |  |  |  |
| Zip7 | S | 5-CTTCGTGCTGTTCCTCATCC-3 | 576 | 58 | Mouse |
|  | AS | 5-CCACGAAAGGAAGCACCAAT-3 |  |  |  |
| ZIP8 | S | 5-ACGATTGCCTGGATGATAACGCTC-3 | 450 | 64 | Human |
|  | AS | 5-GGTAATGAGTAGAATGGCTGTGAATCC-3 |  |  |  |
| Zip8 | S | 5-GAACAATTGCCTGGATGATCACGC-3 | 430 | 62 | Mouse |
|  | AS | 5-AAGCCGGTTAACATCCCTGCATTC-3 |  |  |  |

TABLE 1-continued

PCR primers and conditions

| Gene | Strand | Primer sequences | Size (bp) | AT (° C.) | Origin |
|---|---|---|---|---|---|
| Zip8 | S | 5-CTAAGAAAGCACAACGCAAAGCC-3 | 167 | 62 | Mouse |
|  | AS | 5-CCAATAGCGAGTCCCACGAAATAAG-3 |  |  | (KO) |
| Zip9 | S | 5-GTGTGTCCCTTGTATTGGGC-3 | 473 | 62 | Mouse |
|  | AS | 5-CACTTCAGGGAGGACATGGA-3 |  |  |  |
| Zip10 | S | 5-AGACCAGAGTGAAGACGACC-3 | 360 | 62 | Mouse |
|  | AS | 5-AGTGCAACAAGGAACGTGAG-3 |  |  |  |
| Zip11 | S | 5-CCTTCTTCACCTGGGCAATG-3 | 401 | 62 | Mouse |
|  | AS | 5-AAGCCCAGTGCTACCTATCC-3 |  |  |  |
| Zip12 | S | 5-TCATCGCTCTGTCACTCCAA-3 | 515 | 58 | Mouse |
|  | AS | 5-CATGGAGCCCAAGGTTAGGA-3 |  |  |  |
| Zip13 | S | 5-AACTGGGGCTATGGGTCATC-3 | 535 | 62 | Mouse |
|  | AS | 5-GGTAACACATTCACCAGGGC-3 |  |  |  |
| Zip14 | S | 5-ATTGTCAACTCCATGTCTGTGCAGG-3 | 464 | 64 | Mouse |
|  | AS | 5-CTGTCGTTCTTCTCATCCTCCTGG-3 |  |  |  |
| Znt1 | S | 5-TGATCGTGGTCGTGAATGCCTTG-3 | 486 | 61 | Mouse |
|  | AS | 5-CGAATTCAGGCTGGATGGTGGTAG-3 |  |  |  |
| Znt2 | S | 5-ATTCATGTGATTGGGGACCTTCTGC-3 | 403 | 64 | Mouse |
|  | AS | 5-TCTCAATCTGGATGGTCATGGTGTG-3 |  |  |  |
| Znt3 | S | 5-CTTCCTCCGCCTGCTTCATAGTG-3 | 498 | 58 | Mouse |
|  | AS | 5-TAAGTAAGCGTCAGGGCCCACAG-3 |  |  |  |
| Znt4 | S | 5-AAGCATGGTATCTAGTGGACACAAC-3 | 487 | 61 | Mouse |
|  | AS | 5-CACTTCTTGTCTGTAACTCTGGAGC-3 |  |  |  |
| Znt5 | S | 5-TCTCTCATCATGCCTTTCACCACAG-3 | 509 | 61 | Mouse |
|  | AS | 5-ACGCCATAGAACAACTCCACAAAGG-3 |  |  |  |
| Znt6 | S | 5-TGCTAGAAGTCCGAAATGAACAC-3 | 394 | 58 | Mouse |
|  | AS | 5-CTATATGGCCTTGTCTGTGTGTTC-3 |  |  |  |
| Znt7 | S | 5-TCATGATGGCAGAGGCAATTACAC-3 | 409 | 61 | Mouse |
|  | AS | 5-TCAGAAGGAGTCGAGAGAGCATTG-3 |  |  |  |
| Znt8 | S | 5-GATGTACAAGCTAATGCCAGTG-3 | 429 | 61 | Mouse |
|  | AS | 5-CTGAATGGTAAGAGAGTGAAGATC-3 |  |  |  |
| Znt9 | S | 5-GTTATTCTATTGGAGGACACTGCAG-3 | 414 | 61 | Mouse |
|  | AS | 5-GGCTTCTAATTGTTCAGGAGTCTTC-3 |  |  |  |
| Znt10 | S | 5-CCGAGAATGAACCAGAAGAGACGACG-3 | 435 | 64 | Mouse |
|  | AS | 5-TGCTGGCATCCTGGTATTCCGTG-3 |  |  |  |

AT, annealing temperature;
S, sense;
AS, antisense.

Transcript levels were quantified by qRT-PCR. siRNAs targeting Zip8 and Mtf1 were obtained from Dharmacon and transfected using Lipofectamine 2000. Non-targeting (scrambled) siRNA was used as a negative control. Chondrocytes were transfected by incubating for 6 hours with siRNA and Lipofectamine 2000 (Invitrogen), and infected with adenoviruses as described above. Therapeutic antibodies for obstruction of ZIP8 function were purchased from Santa Cruz Biotechnology and MyBioSource Company, and treated in chondrocytes for 24 hours.

Western Blotting

Total cell lysates were prepared in lysis buffer (150 mM NaCl, 1% NP-40, 50 mM Tris, 5 mM NaF) and used to detect cellular proteins (ZIP8, MTF1, and ERK). Secreted proteins (MMP3, MMP13, and ADAMTS5) were detected after trichloroacetic acid (TCA) precipitation from 900 µl of serum-free conditioned medium. All lysis buffers contained a cocktail of protease inhibitors and phosphatase inhibitors (Roche). Source of antibodies are as follows: ZIP8 and MTF1 in human cartilage tissue sections were detected by antibodies obtained from Proteintech (20459-1-AP) and Novus (NBP1-86380), respectively. The following antibodies were used for immunostaining of mouse joint tissue sections: anti-CRE from Covance (MMS-106P), anti-MMP3 from Epitomics (1908-1), anti-MMP13 from Epitomics (1923-1), anti-MTF1 from Novus (NBP1-86380), anti-MT1/MT2 from Novus (NBP1-97493), and anti-ZIP8 from Santa Cruz Biotechnology (SC-133415). For Western blotting, antibodies were purchased from Thermo Scientific for ADAMTS5 (PA5-14350), BD Biosciences for ERK1

(610408), Epitomics for MMP3 (1908-1) and MMP13 (1923-1), Novus for MTF1 (NBP1-86380), and Santa Cruz Biotechnology for ZIP8 (SC-133415).

Statistical Analysis

Data quantified based on an ordinal grading system, such as OARSI grade, were analyzed using non-parametric statistical methods. For qRT-PCR data expressed as relative fold changes, Student's t-test and analysis of variance (ANOVA) with post hoc tests were used for pair-wise comparisons and multi-comparisons, respectively, after confirming a normal distribution using the Shapiro-Wilk test. Significance was accepted at the 0.05 level of probability (P<0.05).

Results

Figure 1A:
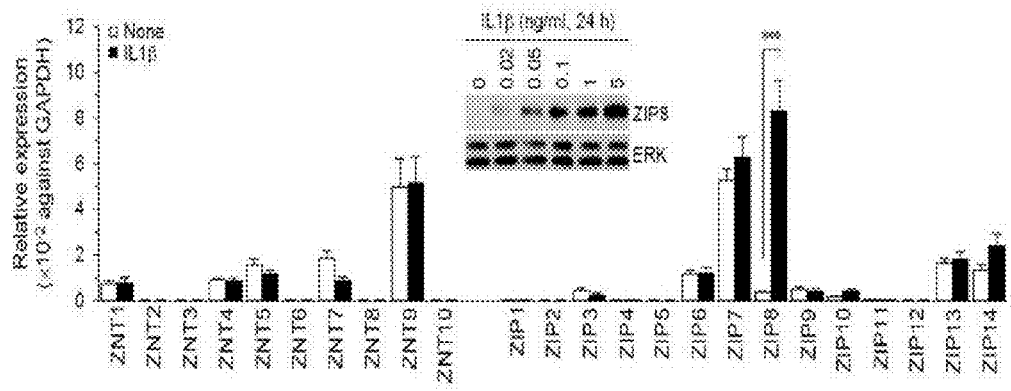
FIG. 1a to 1f represent that the $Zn^{2+}$ Influx Mediator ZIP8 is upregulated in Chondrocytes under Pathological Conditions and in OA Cartilage.
Figure 1B:
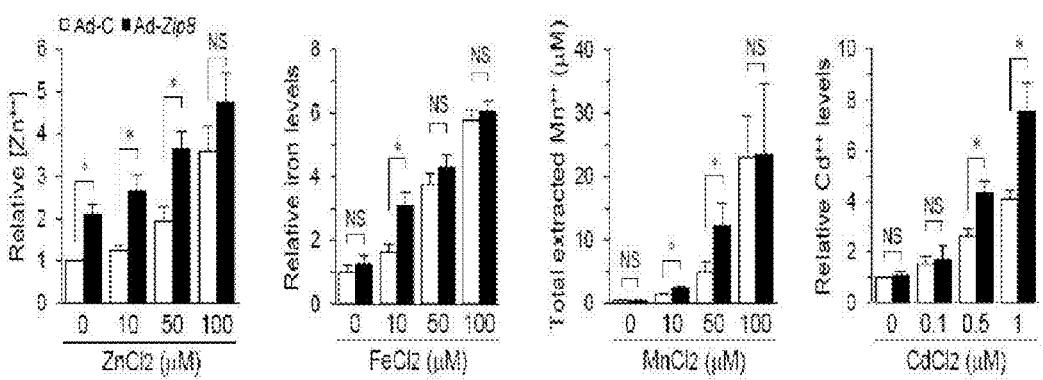
Figure 1C:
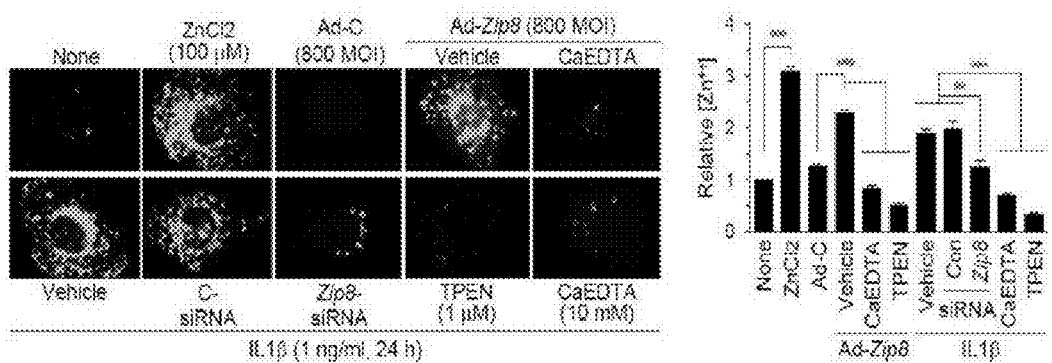
Figure 1D:
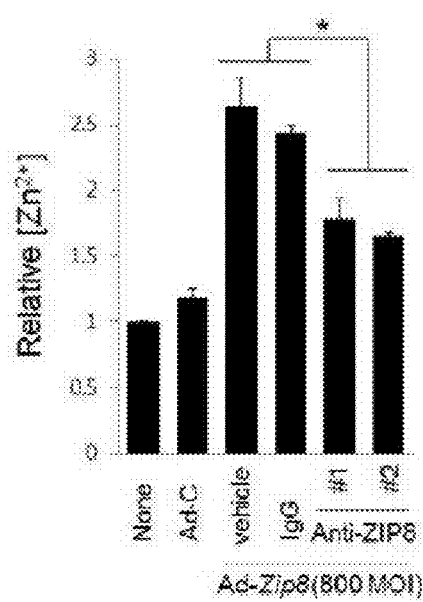

The $Zn^{2+}$ Influx Mediator ZIP8 is Upregulated in Chondrocytes Under Pathological Conditions and in OA Cartilage To elucidate the role of $Zn^{2+}$ homeostasis and associated regulatory genes in OA pathogenesis, we initially examined expression levels of metal ion transporters—the Slc30a family (ZNT) of exporters and Slc39a family (ZIP) of importers—in primary cultures of mouse articular chondrocytes. Among the examined transporters, ZNT9 and ZIP7 mRNAs were expressed at relatively high levels in chondrocytes, whereas many of the remaining transporters were barely detectable (FIG. 1a). However, following treatment with interleukin (IL)1β, a proinflammatory cytokine that promotes catabolism in arthritic cartilage (Kapoor et al., 2010), ZIP8 expression levels were markedly increased, making it the most dominantly expressed transporter among the ZNT and ZIP family members (FIG. 1a). This led us to investigate the role of ZIP8 in OA pathogenesis. ZIP8 is known to transport $Zn^{2+}$, non-transferrin bound $Fe^{2+}$, $Mn^{2+}$, and $Cd^{2+}$ (Dalton et al., 2005; Wang et al., 2012). We therefore examined whether ZIP8 transports these metal ions in mouse articular chondrocytes. Overexpression of ZIP8 in chondrocytes caused significant $Zn^{2+}$ influx (FIGS. 1b and 1c), whereas cellular levels of $Fe^{2+}$, $Mn^{2+}$, and $Cd^{2+}$ were not affected by ZIP8 overexpression alone (FIG. 1b). However, in a certain range of each metal ion supplementation, ZIP8 effectively drove influx of these metal ions (FIG. 1b), suggesting that the transport efficiency of each metal ion by ZIP8 is determined by the cellular microenvironmental context, with Zn2+ evidently being the most efficiently transported by ZIP8 under our experiment conditions. Thus, we further characterized the regulation of $Zn^{2+}$ influx by ZIP8. The ZIP8-mediated increase in $Zn^{2+}$ influx was abolished by the cell-impermeable metal ion chelator, calcium-saturated EDTA (CaEDTA), or the cell-permeable chelator, TPEN [N,N,N',N'-tetrakis (2-pyridylmethyl)ethylenediamine] (FIG. 1c). IL1β, which increased both transcript and protein levels of ZIP8, caused an influx of $Zn^{2+}$ in chondrocytes that was blocked by downregulating Zip8 with small interfering RNA (siRNA) or the metal ion chelators CaEDTA or TPEN (FIG. 1c). Also, cellular $Zn^{2+}$ levels were quantified in chondrocytes infected with Ad-Zip8, with therapeutic ZIP8 antibodies. The results showed that the increase of $Zn^{2+}$ influx by ZIP8 was suppressed (FIG. 1d).

Figure 1E:
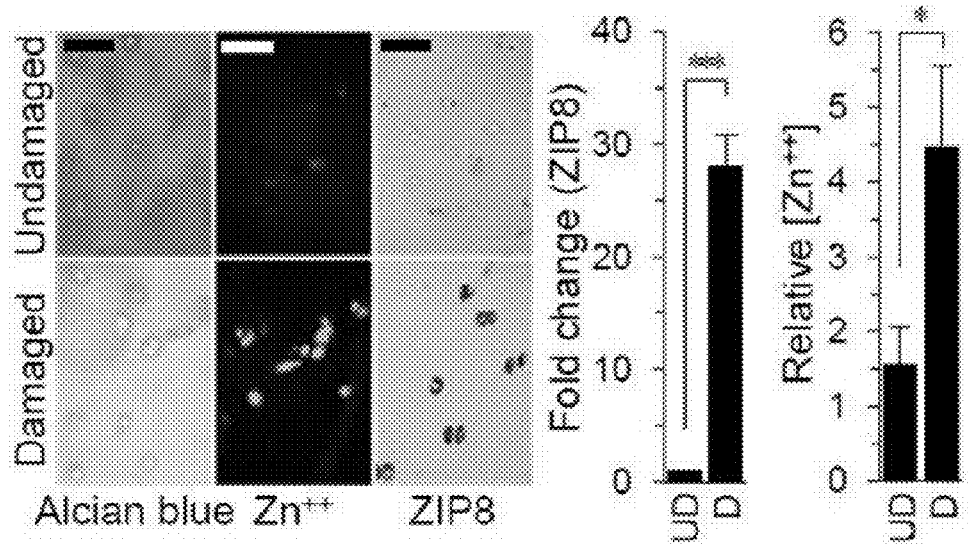
Figure 1F:
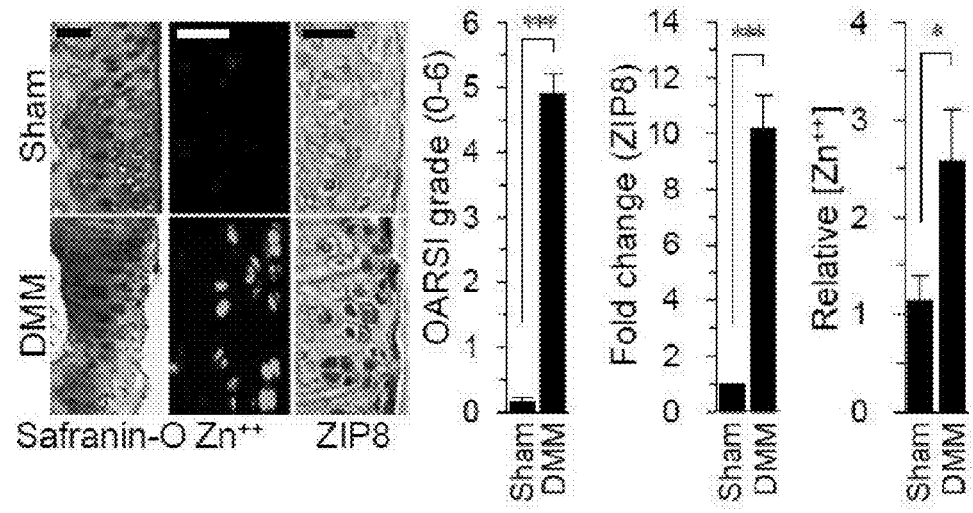

The upregulation of ZIP8 and $Zn^{2+}$ influx in chondrocytes under pathological conditions (i.e., exposure to IL1β) suggests the possible association of ZIP8-mediated $Zn^{2+}$ influx with OA pathogenesis. This was evaluated by examining expression of ZIP8 and $Zn^{2+}$ levels in OA cartilage of human and mouse models. Damage of OA-affected human cartilage was established based on alcian blue staining (FIG. 1e). $Zn^{2+}$ and ZIP8 protein and mRNA levels were markedly elevated in OA-affected human cartilage, but were barely detectable in undamaged regions of arthritic cartilage (FIG. 1d). We also used destabilization of the medial meniscus (DMM) surgery as a mouse model of OA and compared it with normal cartilage in a shamoperated joint (Glasson et al., 2007). Similar to human OA cartilage, mouse OA cartilage showed a marked increase in $Zn^{2+}$ and ZIP8 protein and mRNA levels (FIG. 1f).

ZIP8-Mediated $Zn^{2+}$ Influx Induces Upregulation of Matrix-Degrading Enzymes in Chondrocytes The increased expression of ZIP8 and elevated $Zn^{2+}$ levels in OA cartilage suggests their possible involvement in OA pathogenesis. A hallmark of OA chondrocytes is their increased production of $Zn^{2+}$-bound matrix-degrading enzymes such as MMPs and ADAMTSs. We therefore asked whether cellular $Zn^{2+}$ influx driven by ZIP8 is sufficient to cause expression of matrix-degrading enzymes. Among the examined enzymes, MMP3, MMP9, MMP12, MMP13, and ADAMTS5 were significantly upregulated by infection of chondrocytes with an adenoviral Zip8 expression construct (Ad-Zip8); this effect was blocked by metal ion chelation with CaEDTA or TPEN (FIG. 2A). Consistent with this, treatment of chondrocytes with ZnCl2 up-regulated MMP3, MMP9, MMP12 and MMP13, whereas treatment with $CdCl_2$ or $MnCl_2$ did not cause a marked expression of matrix-degrading enzymes (FIG. 2B). $FeCl_2$ treatment caused moderate expression of matrix-degrading enzymes. However, chelation of ferric or ferrous with Zn/DFO or 2,2-bipyridyl, respectively, did not affect Ad-Zip8-induced expression of matrix-degrading enzymes (FIG. 2C), consistent with the fact that ZIP8 did not cause $Fe^{2+}$ influx without exogenous $FeCl_2$ supplementation. Furthermore, pre-incubation of TPEN with $ZnCl_2$ effectively abolished the inhibitory effects of TPEN on the ZIP8-mediated expression of matrix-degrading enzymes, whereas $FeCl_2$, $CdCl_2$, and $MnCl_2$ showed no significant effects on TPEN inhibition of the ZIP8-mediated upregulation of matrix-degrading enzymes (FIG. 2D). These results collectively suggest that $Zn^{2+}$, among the metal ions transported by ZIP8, plays a major role in ZIP8 regulation of the expression of matrix-degrading enzymes. Among the ZIP8-regulated matrix-degrading enzymes, MMP3, MMP13, and ADAMTS5 are crucial effectors of OA cartilage destruction (Blom et al., 2007; Glasson et al., 2005; Little et al., 2009). Indeed, upregulation of these enzymes by IL1β was abolished by knockdown of Zip8 with specific siRNA or by metal ion chelation with CaEDTA or TPEN (FIGS. 2E and F). Collectively, these results suggest ZIP8-mediated $Zn^{2+}$ influx exerts a catabolic function in chondrocytes by virtue of its role in upregulating matrix-degrading enzymes.

ZIP8 Overexpression in Cartilage Tissue Causes OA Pathogenesis in Mice

The role of ZIP8-mediated $Zn^{2+}$ influx in OA pathogenesis was directly examined by intraarticular (IA) injection of Ad-Zip8 into mouse knee joints. We have previously shown that the adenoviral system effectively delivers genes into mouse joint tissues (Yang et al., 2010, Ryu et al., 2011 and 2012; Oh et al., 2012), and further confirmed gene delivery via this system by injecting Ad-eGFP (FIG. 3a). Ad-Zip8 injection caused ZIP8 overexpression in cartilage, meniscus, ligament, and synovium (FIGS. 3b and 3c). Three weeks after Ad-Zip8 injection, chondrocytes of cartilage tissue exhibited markedly increased levels of $Zn^{2+}$, MMP3, and MMP13 (FIG. 3b) with concomitant cartilage destruction (FIGS. 3d and 3e). IA injection of Ad-Zip8 also caused synovitis (FIG. 3f). Consistent with this, overexpression of ZIP8 in primary cultured mouse fibroblast-like synoviocytes caused upregulation of various catabolic factors, including matrix-degrading enzymes, cytokines, and chemokines (FIG. 3g). Additionally, Ad-Zip8-induced MMP expression, cartilage destruction, and synovitis were significantly blocked by co-injection of TPEN. Other OA manifestations, such as osteophyte development and subchondral bone sclerosis, were not observed at 3 weeks after Ad-Zip8 injection. However, 8 weeks after IA injection, joint tissues exhibited osteophyte development and subchondral bone sclerosis with more severe cartilage destruction (FIG. 3h). Collectively, these results demonstrate that ZIP8-mediated $Zn^{2+}$ influx acts as a catabolic regulator of OA pathogenesis.

The in vivo role of ZIP8-mediated $Zn^{2+}$ influx in OA pathogenesis was further validated using chondrocyte-specific Zip8-overexpressing transgenic (TG) mice (Col2a1-Zip8), in which Zip8 expression is driven by the promoter and enhancer region of mouse Col2a1 (Yang et al., 2010, Oh et al., 2012). Col2a1-Zip8 TG mice expressed markedly enhanced levels of ZIP8 in cartilage and meniscus, but not in the synovium or ligaments, of joint tissues (FIGS. 3i and 3j). Zip8 TG mice also showed increased levels of $Zn^{2+}$, MMP3, and MMP13 in cartilage tissue (FIG. 3i). Consistent with this, aged (12-month-old) Zip8 TG mice exhibited spontaneous cartilage destruction (FIG. 3l), with OARSI grades ranging from 1 to 6 (FIG. 3k), and subchondral bone sclerosis (FIG. 3m) compared with age-matched wild-type (WT) mice; synovitis was not observed in Zip8 TG mice (FIG. 3n). Additionally, DMM surgery in young (10- to 12-weeks-old) Zip8 TG mice showed significantly enhanced OA cartilage destruction (FIG. 3o) and subchondral bone sclerosis, whereas synovitis and osteophyte development were not affected (FIG. 3p). These features of Zip8 TG mice clearly support the notion that ZIP overexpression in cartilage tissue is sufficient to cause OA pathogenesis.

Zip8 Knockout in Mice Inhibits Experimental OA Pathogenesis

We next confirmed the catabolic role of ZIP8 in OA pathogenesis using Zip8-knockout (KO) mice. Because homozygous deletion of Zip8 in mice ($Zip8^{-/-}$) is embryonic lethal (Galvez Peralta et al., 2012), we evaluated the effect of Zip8 knockout on OA pathogenesis using chondrocyte-specific conditional KO (CKO) mice ($Zip8^{fl/fl}$; Col2a1-Cre). Zip8-CKO mice showed a significant reduction in OA cartilage destruction following DMM surgery (FIG. 4a), with concomitant inhibition of ZIP8 expression, $Zn^{2+}$ influx, and expression of MMP3 and MMP13 in cartilage tissue (FIG. 4b). Consistent with this, IL1β-induced $Zn^{2+}$ influx and expression of MMP3, MMP13, and ADAMTS5 were reduced in primary cultured chondrocytes isolated from Zip8-CKO mice (FIGS. 4c and 4d). In addition to cartilage destruction, DMM-operated Zip8-CKO mice exhibited significant inhibition of subchondral bone sclerosis, whereas synovitis and osteophyte formation were not affected (FIGS. 4e and 4f). The results collectively suggest that genetic deletion of Zip8 inhibits experimental OA pathogenesis in mice. Similar to Zip8 CKO mice, $Zip8^{+/-}$ mice also exhibited reduced OA cartilage destruction and subchondral bone sclerosis following DMM surgery (data not shown).

ZIP8-Mediated $Zn^{2+}$ Influx Upregulates Matrix-Degrading Enzymes by Enhancing MTF1 Transcriptional Activity Next, we elucidated the regulatory mechanisms by which ZIP8-mediated $Zn^{2+}$ influx mediates catabolic factor expression and OA pathogenesis. To do this, we first identified transcription factors activated by ZIP8-mediated $Zn^{2+}$ influx in chondrocytes using a transcription factor array kit. Among the 37 transcription factors examined, MTF1, NRF1 and NRF2, NF-κB, SP1, p53, C/EBP, and AP1 showed more than a 3-fold increase in transcriptional activity following Ad-Zip8 infection (FIG. 5a). Pharmacological inhibition of p53, AP1 or NF-κB, or siRNA mediated knockdown of Nrf or Cebpb had no significant effect on Ad-Zip8-induced upregulation of matrix-degrading enzymes (FIGS. 5b and 5c). However, knockdown of Mtf1 with siRNA or inhibition of SP1 with mithramycin-A significantly attenuated ZIP8-induced upregulation of matrix-degrading enzymes (FIGS. 5d and 5e). Based on these observations and the fact that MTF1 is a master transcriptional regulator of cellular adaptation under conditions of exposure to heavy metals (Laity and Andrews, 2007; Gunther et al., 2012), we selected MTF1 for functional characterization in ZIP8-induced OA pathogenesis. Ad-Zip8 infection promoted the nuclear localization of MTF1 (FIG. 5f) and significantly increased its transcriptional activity (FIG. 5g), without modulating its expression (FIG. 5h). Notably, Ad-Mtf1 infection significantly upregulated expression of matrix-degrading enzymes (MMP3, MMP9, MMP12, MMP13, and ADAMTS5), an effect that was abolished by CaEDTA or TPEN (FIGS. 5i and 5j). Additionally, ZIP8 or $Zn^{2+}$-induced upregulation of matrix-degrading enzymes was significantly reduced by siRNA-mediated knockdown of Mtf1 (FIGS. 5d and 5k). Among the ZIP8-regulated metal ions, $Zn^{2+}$ was the most effective in regulating nuclear localization and transcriptional activation of MTF1, and $Fe^{2+}$ and $Mn^{2+}$ had no effect on MTF1 activity (FIGS. 5l and 5m). Although $Cd^{2+}$ caused a moderate activation of MTF1 (FIG. 5m), it had no significant effect on the expression of matrix-degrading enzymes, except for a modest induction of MMP12 expression (FIG. 2b). This suggests that, unlike the effects of $Zn^{2+}$-dependent activation of MTF1, $Cd^{2+}$-induced MTF1 activation does not cause expression of matrix-degrading enzymes. This discrepancy may reflect the fact that MTF1 regulates target gene expression in a metal-specific manner (Gunther et al., 2012). Additionally, pre-incubation of TPEN with $ZnCl_2$, but not $FeCl_2$, $CdCl_2$ or $MnCl_2$, abolished the inhibitory effects of TPEN on MTF1 transcriptional activity (FIG. 5n). These results collectively suggest that ZIP8-mediated $Zn^{2+}$ influx promotes MTF1 transcriptional activity, which in turn upregulates expression of matrix-degrading enzymes in chondrocytes.

MTF1 Mediates ZIP8-Induced OA Pathogenesis in Mice

We next examined the in vivo role of MTF1 in OA pathogenesis. In human cartilage tissues, both MTF1 mRNA and protein were detected at high levels in OA-affected cartilage tissue compared with undamaged regions of arthritic cartilage (FIG. 6a). The in vivo function of MTF1 was evaluated by IA injection of Ad-Mtf1 in mice, which caused MTF1 overexpression in the joint tissues (FIGS. 6b and 6c). Expression levels of MTF1, MMP3, and MMP13 in the chondrocytes of cartilage tissue were markedly enhanced at 3 weeks after Ad-Mtf1 injection (FIG. 6b) with concomitant cartilage destruction (FIG. 6d). IA injection of Ad-Mtf1 also caused synovial inflammation (FIG. 6e), and overexpression of MTF1 in fibroblast-like synoviocytes caused upregulation of various catabolic factors, including matrix-degrading enzymes, cytokines, and chemokines (FIG. 6f). Similar to the effects of Ad-Zip8 injection, Ad-Mtf1 injection in mice caused osteophyte formation and subchondral bone sclerosis at 8 weeks after IA injection, with more severe cartilage destruction (FIG. 6g).

We also confirmed MTF1 function in OA pathogenesis using Mtf1-KO mice. Chondrocyte-specific CKO mice ($Mtf1^{fl/fl}$; Col2a1-Cre) exhibited significantly reduced OA cartilage destruction following DMM surgery (FIG. 6h), with concomitant reduction of the expression MTF1, MMP3, and MMP13 (FIG. 6i). DMM-operated Mtf1-CKO mice also exhibited inhibition of subchondral bone sclerosis without significant effects on synovitis or osteophyte formation (FIG. 6j). Additionally, DMM-operated Mtf1$^{+/-}$ •mice (homozygous deletion of Mtf1 is embryonic lethal; Wang et al., 2004) also exhibited reduced cartilage destruction, subchondral bone sclerosis, and expression of MMP3 and MMP13 (data not shown). To further elucidate MTF1 as the mediator of ZIP8 functions, we IA co-injected Mtf1$^{fl/fl}$ mice with Ad-Zip8 and Ad-Cre to locally delete Mtf1 in joint tissues. This local deletion of Mtf1 significantly inhibited Ad-Zip8-induced cartilage destruction and synovitis (FIG. 6k). In contrast, local deletion of Zip8 by Ad-Cre injection in Zip8$^{fl/fl}$ mice did not affect Ad-Mtf1-induced cartilage destruction or synovitis (FIG. 6l). This clearly supports the notion that MTF1 is a downstream mediator of ZIP8 in OA pathogenesis and ZIP8-activated MTF1 acts as a catabolic regulator of OA cartilage destruction by upregulating matrix-degrading enzymes in chondrocytes.

Finally, we explored the effects of dietary $Zn^{2+}$ supplementation on surgically induced OA. Low-$Zn^{2+}$ diet did not affect DMM-induced OA cartilage destruction, presumably due to trace amount of $Zn^{2+}$ (<0.5 mg zinc/kg). However, mice fed a high-Zn2+ diet exhibited enhanced cartilage destruction following DMM surgery (FIG. 6m). Consistent with this, intraperitoneal administration of $ZnCl_2$ augmented DMM-induced cartilage destruction (FIG. 6n). Taken together, these observations indicate that $Zn^{2+}$ levels are positively correlated with OA pathogenesis, consistent with our findings that ZIP8-mediated $Zn^{2+}$ influx and MTF1 activation favor OA development.

Knockout of MT Genes Enhances OA Cartilage Destruction in Mice

MTs, which are well-known targets of MTF1, regulate $Zn^{2+}$ homeostasis by virtue of their function as $Zn^{2+}$-storage proteins and they protect cells from oxidative stress by acting as antioxidants (Laity and Andrews, 2007; Colvin et al., 2010; Fukada et al., 2011). We therefore elucidated possible functions of MTs in OA pathogenesis. Expression of Mt1 and Mt2, which encode the closely related MT1 and MT2 proteins, was significantly increased in primary cultured chondrocytes infected with Ad-Zip8 or Ad-Mtf1 or treated with $ZnCl_2$ (FIGS. 7a and 7b). The in vivo significance of MT1/MT2 in OA pathogenesis was evaluated using Mt1$^{-/-}$; Mt2$^{-/-}$ double-KO mice. Compared with WT mice, DMM-operated Mt1$^{-/-}$; Mt2$^{-/-}$ double-KO mice exhibited significantly enhanced OA cartilage destruction (FIG. 7c) and subchondral bone sclerosis without significant effects on synovitis and osteophyte formation (FIGS. 7d and 7e).

These results collectively suggest that MTF1 activation caused by ZIP8-mediated $Zn^{2+}$ influx activates a catabolic cascade by upregulating matrix-degrading enzymes, whereas upregulation of MT1 and MT2 proteins by MTF1 forms a negative feedback loop that alleviates zinc cascade induced OA pathogenesis.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Devireddy, L. R., Gazin, C., Zhu, X., and Green, M. R. (2005). A cell-surface receptor for lipocalin 24p3 selectively mediates apoptosis and iron uptake. Cell. 123, 1293-1305.

Gosset, M., Berenbaum F., Thirion S., and Jacques, C. (2008). Primary culture and phenotyping of murine chondrocytes, Nat. Protoc. 3, 1253-1260.

Honda, T., Segi-Nishida, E., Miyachi, Y., Narumiya, S. (2006). Prostacyclin-IP signaling and prostaglandin E2-EP2/EP4 signaling both mediate joint inflammation in mouse collageninduced arthritis. J. Exp. Med. 203, 325-335.

Kwakye, G. F., Li, D., and Bowman, A. B. (2011). Novel high-throughput assay to assess cellular manganese levels in a striatal cell line model of Huntingtons disease confirms a deficit in manganese accumulation. NeuroToxicol. 32, 630-639.

Prokunina-Olsson, L., Muchmore, B., Tang, W., Pfeiffer, R. M., Park, H., Dickensheets, H., Hergott, D., Porter-Gill, P., Mumy, A., Kohaas, I. et al. (2013). A variant upstream of IFNL3 (IL28B) creating a new interferon gene IFNL4 is associated with impaired clearance of hepatitis C virus. Nat. Genet. 45, 164-171.

Riemer, J., Hoepken, H. H., Czerwinska, H., Robinson, S. R., and Dringen, R. (2004). Colorimetric ferrozine-based assay for the quantitation of iron in cultured cells. Anal Biochem. 331, 370-375.

Romeo, A. M., Christen, L., Niles, E. G., and Kosman, D. J. (2001). Intracellular chelation of iron by bipyridyl inhibits DNA virus replication: ribonucleotide reductase maturation as a probe of intracellular iron pools. J. Biol. Chem. 276, 24301-24308.

Samuni, Y., Coffin, D., DeLuca, A. M., DeGraff, W. G., Venson, D. J., Ambudkar, I., Chevion, M., and Mitchell, J. B. (1999). The use of Zn-desferrioxamine for radioprotection in mice, tissue culture, and isolated DNA. Cancer Res. 59, 405-409.

Yamasaki, S., Sakata-Sogawa, K., Hasegawa, A., Suzuki, T., Kabu, K., Sato, E., Kurosaki, T., Yamashita, S., Tokuna, M., Nishida, K., et al. (2007). Zinc is a novel intracellular second messenger. J. Cell Biol. 177, 637-645.

What is claimed is:

1. A method for treating a joint disease, comprising: administering to a subject in need thereof an inhibitor of the expression of the metal-regulatory transcription factor-1 (MTF1) gene of SEQ ID NO:3 or the activity of the MTF1 protein of SEQ ID NO:4,
wherein the joint disease is osteoarthritis, and
wherein the inhibitor of the expression of the MTF1 gene is selected from the group consisting of siRNA (small interference RNA), shRNA (short hairpin RNA), miRNA (microRNA), and an antisense oligonucleotide, and
wherein the inhibitor of the activity of the MTF1 protein is an antibody.

2. The method according to claim 1, wherein the inhibitor as an active ingredient decreases the expression of matrix-degrading enzyme in mRNA level or protein level.

3. The method according to claim 2, wherein the matrix-degrading enzyme is MMP-3 (matrix metalloproteinase 3), MMP-9, MMP-12, MMP-13, or ADAMTS-5 (a disintegrin and metalloproteinase with thrombospondin motifs 5).

4. The method according to claim 1, further comprising administering to the subject an inhibitor of the expression of the ZIP8 gene of SEQ ID NO:1 or the activity of the ZIP8 protein of SEQ ID NO:2,
wherein the inhibitor of the expression of the ZIP8 gene is selected from the group consisting of siRNA (small interference RNA), shRNA (short hairpin RNA), miRNA (microRNA), and an antisense oligonucleotide, and
wherein the inhibitor of the activity of the ZIP8 protein is an antibody.

5. The method according to claim 4, wherein the inhibitor as an active ingredient decreases the expression of matrix-degrading enzyme in mRNA level or protein level.

6. The method according to claim 5, wherein the matrix-degrading enzyme is MMP-3 (matrix metalloproteinase 3), MMP-9, MMP-12, MMP-13, or ADAMTS-5 (a disintegrin and metalloproteinase with thrombospondin motifs 5).

* * * * *